United States Patent
Wohl et al.

(10) Patent No.: US 9,002,485 B2
(45) Date of Patent: Apr. 7, 2015

(54) METHOD, APPARATUS, AND COMPUTER PROGRAM PRODUCT FOR PERFORMANCE ANALYTICS DETERMINING PLAY MODELS AND OUTPUTTING EVENTS BASED ON REAL-TIME DATA FOR PROXIMITY AND MOVEMENT OF OBJECTS

(71) Applicant: ZIH Corp., Lincolnshire, IL (US)

(72) Inventors: Michael A. Wohl, Rogersville, TN (US); James J. O'Hagan, Lincolnshire, IL (US); Anthony R. Brown, Lincolnshire, IL (US); Wolfgang Strobel, Lincoln, RI (US); Dean Lodwig, Agoura Hills, CA (US)

(73) Assignee: ZIH Corp., Lincolnshire, IL (US)

( * ) Notice: Subject to any disclaimer, the term of this patent is extended or adjusted under 35 U.S.C. 154(b) by 20 days.

(21) Appl. No.: 13/942,316

(22) Filed: Jul. 15, 2013

(65) Prior Publication Data

US 2014/0364974 A1    Dec. 11, 2014

Related U.S. Application Data

(60) Provisional application No. 61/831,990, filed on Jun. 6, 2013.

(51) Int. Cl.
    *G06K 7/10*          (2006.01)
    *A63B 71/06*        (2006.01)

(52) U.S. Cl.
    CPC ........ *A63B 71/0622* (2013.01); *G06K 7/10366* (2013.01)

(58) Field of Classification Search
    CPC ........................ A63B 24/0021; A63B 71/0622
    USPC ............................................................ 700/91
    See application file for complete search history.

(56) References Cited

U.S. PATENT DOCUMENTS

| | | |
|---|---|---|
| 5,901,172 A | 5/1999 | Fontana et al. |
| 6,882,315 B2 | 4/2005 | Richley et al. |

(Continued)

FOREIGN PATENT DOCUMENTS

WO     WO-9805977 A1     2/1998

OTHER PUBLICATIONS

International Search Report and Written Opinion from International Application No. PCT/US2014/041062 dated Oct. 1, 2014.

(Continued)

*Primary Examiner* — Corbett B Coburn
(74) *Attorney, Agent, or Firm* — Alston & Bird LLP

(57) ABSTRACT

Systems, methods, apparatuses, and computer readable media are disclosed for providing analytics using real time data on movement and proximity of tagged objects for determining play models and outputting events. In one embodiment, a method is provided for determining play data that at least includes correlating at least one tag to a participant; receiving blink data transmitted by the at least one tag; and determining tag location data based on the blink data. The method further includes receiving participant role data; comparing the tag location data to participant dynamics/kinetics models based at least in part on the participant role data; determining participant location data based on the comparing the tag location data to the participant dynamics/kinetics models. The method further includes receiving field data; comparing the participant location data to formation models based at least in part on the participant role data and the field data; and determining formation data based on the comparing the participant location data to the formation models. The method further includes comparing the formation data and participant location data to play models; and determining play data based on the comparing the formation data and participant location data to the play models.

20 Claims, 12 Drawing Sheets

(56) References Cited

U.S. PATENT DOCUMENTS

| | | | |
|---|---|---|---|
| 7,667,604 | B2 | 2/2010 | Ebert et al. |
| 7,671,802 | B2 | 3/2010 | Walsh et al. |
| 7,710,322 | B1 | 5/2010 | Ameti et al. |
| 7,755,541 | B2 | 7/2010 | Wisherd et al. |
| 7,969,348 | B2 | 6/2011 | Baker et al. |
| 8,457,392 | B2 | 6/2013 | Cavallaro et al. |
| 2002/0116147 | A1 | 8/2002 | Vock et al. |
| 2003/0163287 | A1 | 8/2003 | Vock et al. |
| 2008/0140233 | A1 | 6/2008 | Seacat |
| 2008/0281443 | A1 | 11/2008 | Rodgers |
| 2009/0231198 | A1 | 9/2009 | Walsh et al. |
| 2010/0283630 | A1 | 11/2010 | Alonso |
| 2011/0084806 | A1 | 4/2011 | Perkins et al. |
| 2012/0065483 | A1 | 3/2012 | Chung et al. |
| 2012/0112904 | A1 | 5/2012 | Nagy et al. |
| 2012/0126973 | A1* | 5/2012 | DeAngelis et al. ...... 340/539.13 |
| 2012/0218301 | A1 | 8/2012 | Miller |
| 2012/0225676 | A1 | 9/2012 | Boyd et al. |
| 2012/0256745 | A1 | 10/2012 | Plett et al. |
| 2013/0066448 | A1 | 3/2013 | Alonso |

OTHER PUBLICATIONS

International Search Report and Written Opinion from International Application No. PCT/US2014/040947 dated Oct. 9, 2014.

Swedberg, C., "N.J. Company Seeks to Market Passive Sensor RFID Tags," *RFID Journal*, Jun. 20, 2013.

Fontana, R.J., Richley, E., Barney, J., "Commercialization of an Ultra Wideband Precision Asset Location System," *2003 IEEE Conference on Ultra Wideband Systems and Technologies*, Nov. 16-19, 2003.

Gueziec, A., "Tracking Pitches for Broadcast Television," *Computer*, Aug. 7, 2002.

International Search Report and Written Opinion from International Application No. PCT/US2014/040881 dated Nov. 4, 2014.

Cattlelog Pro *Emerge's Premiere Individual Animal Management and Data Collection Tool* (dated 2004) 2 pages.

Marchant, J., *Secure Animal Identification and Source Verification*, Optibrand Ltd., LLC (dated 2002), 28 pages.

*A guide to using NLIS approved ear tags and rumen boluses*, National Livestock Identification Scheme (dated May 2003), 4 pages.

NAIS Cattle ID Pilot Projects Not Needed, Since Proven Advanced Technology Already Exists, http://www/prweb.com/releases/2005/12/prweb325888.htm, [online] [retrieved Jul. 25, 2013]. Retrieved from the Internet: <URL: http://03sharepoint/sites/busimprove/cowtag/2%20Solution%20Requirements/FW%20NAI . . . > (dated 2005) 2 pages.

RFID in the Australian Meat and Livestock Industry, Data Capture Suppliers Guide 2003-2004, (dated 2003-2004) 3 pages.

* cited by examiner

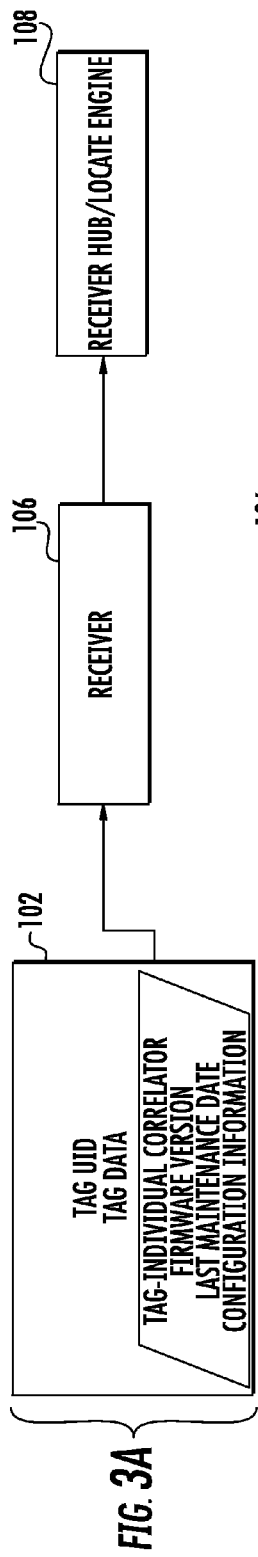
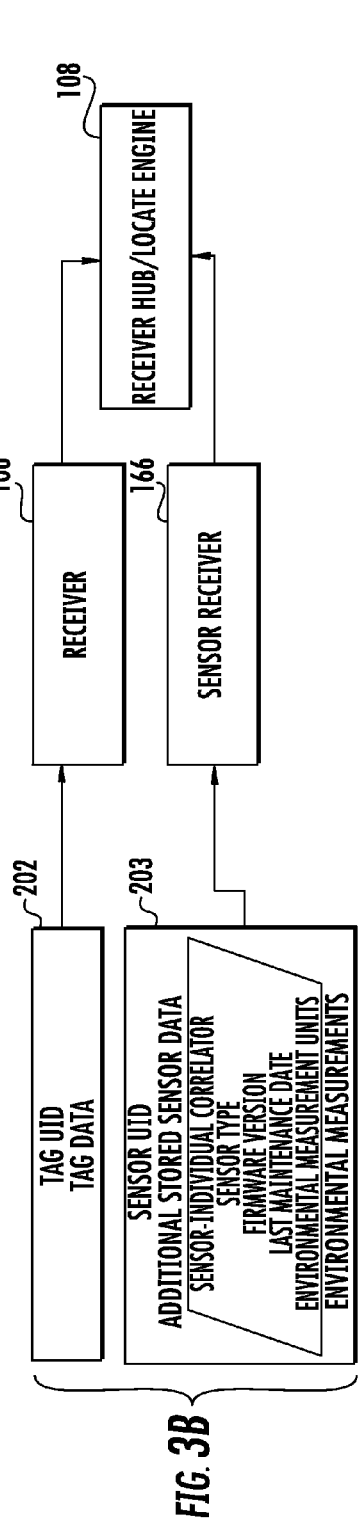
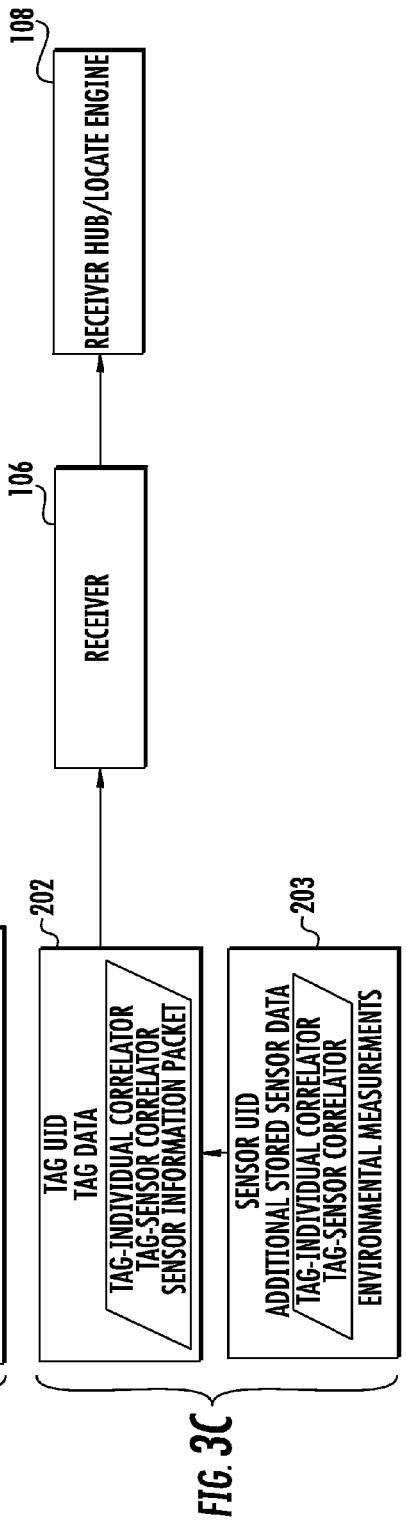
FIG. 3A
FIG. 3B
FIG. 3C

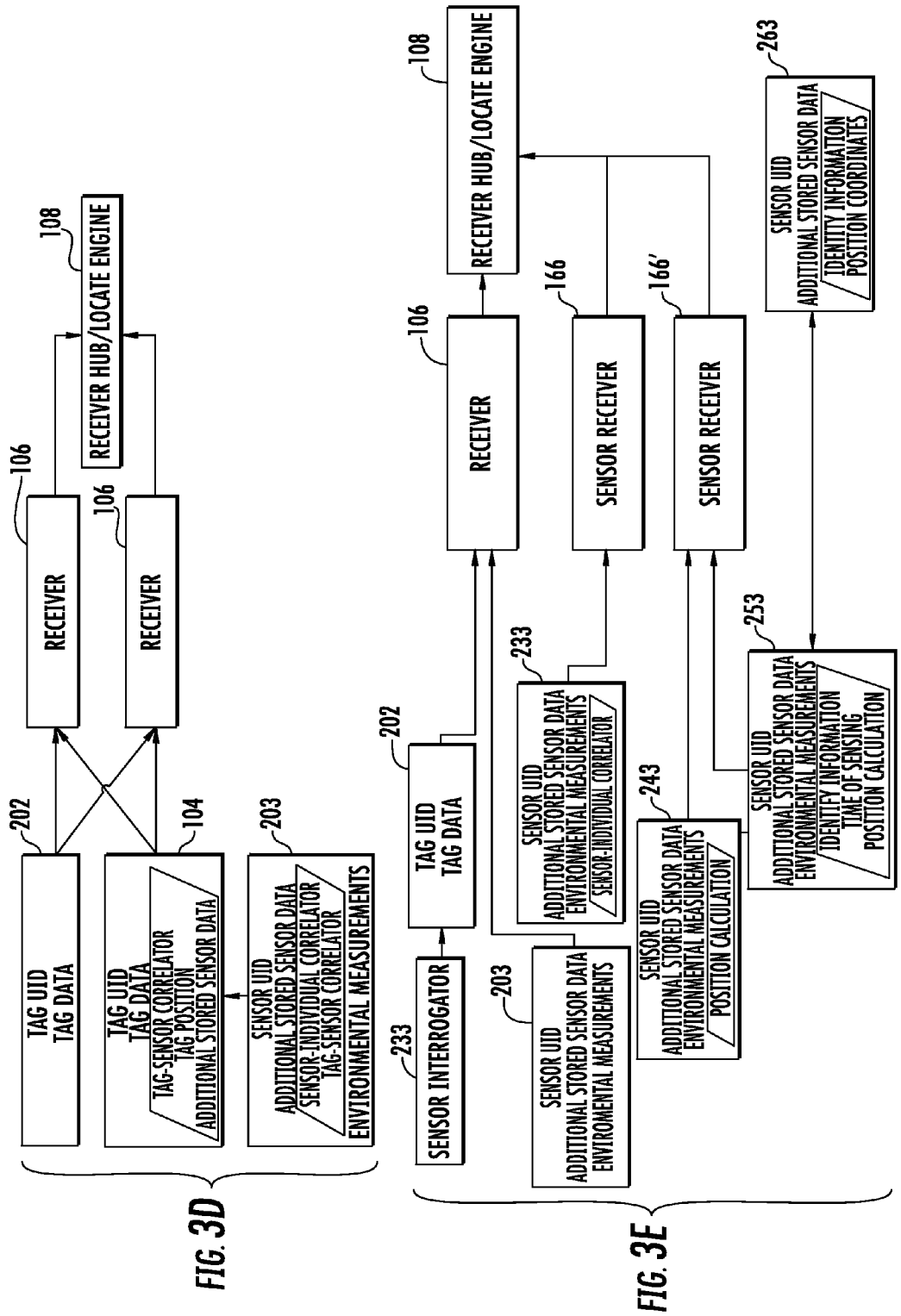

METHOD, APPARATUS, AND COMPUTER PROGRAM PRODUCT FOR PERFORMANCE ANALYTICS DETERMINING PLAY MODELS AND OUTPUTTING EVENTS BASED ON REAL-TIME DATA FOR PROXIMITY AND MOVEMENT OF OBJECTS

CROSS-REFERENCE TO RELATED APPLICATION

This application claims priority from and the benefit of the filing date of U.S. Provisional Patent Application No. 61/831,990 filed Jun. 6, 2013, the contents of which is incorporated by reference in its entirety herein.

FIELD

Embodiments discussed herein are related to radio frequency locating and, more particularly, to systems, methods, apparatuses, computer readable media and other means for providing performance analytics.

BACKGROUND

Producing analysis of performance for sports events and/or teams is generally a resource intensive process often involving experienced individuals manually reviewing games or recordings of games to compile events and statistics for a game and the participants. Such analysis may be error prone as it requires reviewing a large number of participants moving among complex formations at each moment of a game.

A number of deficiencies and problems associated with providing performance analytics are identified herein. Through applied effort, ingenuity, and innovation, exemplary solutions to many of these identified problems are embodied by the present invention, which is described in detail below.

BRIEF SUMMARY

Systems, methods, apparatuses, and computer readable media are disclosed for providing real-time collection and analysis of participant (e.g., player) performance, events, and statistics during a sporting event or other group activity using a locating system, such as a radio frequency locating system, as herein described.

Embodiments of the present invention may provide for automatic recognition of formations, plays, and events during a sporting event through the processing of real time (or near real time) data regarding location, change in location, change in acceleration, orientation, sensor data, or the like, for participants that comprise a team or are otherwise associated with a sporting event or other group activity and how such data fits models that define the formations, plays, and events. Once such formations, plays, and events have been defined or identified they may be used to operate, control, or drive analytics or control systems such as, without limitation, visualization systems, game operations systems, camera control systems, team analytics systems, league analytics systems, statistics systems, and XML feed/IM feed systems.

In one embodiment, a method for monitoring a participant is provided, the method comprising correlating at least one tag to the participant, receiving blink data transmitted by the at least one tag, determining tag location data based on the blink data, comparing the tag location data to participant dynamics/kinetics models based at least in part on the tag location data, and determining participant location data based on the comparing the tag location data to the participant dynamics/kinetics models.

In some embodiments, the tag comprises an ultra-wide-band (UWB) transmitter. In some embodiments, determining tag location data comprises determining a first tag derived data component and a second tag derived data component, and wherein the determining participant location data comprises determining participant location data by assigning a first weight to the first tag derived data component and a second weight to the second tag derived data component.

In some embodiments, the determining participant location data comprises assigning the first weight to the first tag derived data component and the second weight to the second tag derived data component at a first time period, and further comprises assigning a third weight to the first tag derived data component and assigning a fourth weight to the second tag derived data component at a second time period. In some embodiments, the method may further comprise receiving field data, receiving participant role data, comparing the participant location data to formation models based at least in part on the participant role data and the field data, and determining formation data based on the comparing the participant location data to the formation models.

In some embodiments, the participant location data comprises a first participant component and a second participant component, and wherein the determining formation data comprises determining formation data by assigning a first weight to the first participant component and a second weight to the second participant component. In some embodiments, the determining participant location data comprises assigning the first weight to the first participant component and the second weight to the second participant component at a first time period, and further comprises assigning a third weight to the first participant component at a second time period and assigning a fourth weight to the second participant component at the second time period.

In some embodiments, the participant dynamics/kinetics models comprise location history data for the participant. In some embodiments, the method may further comprise updating the participant role data based on the participant location data. In some embodiments, the method may further comprise updating the dynamics/kinetics models based on the participant location data. In some embodiments, the method may further comprise updating the formation models based on the formation data. In some embodiments, the UWB transmitter is configured to transmit blink data comprising a plurality of time of arrival (TOA) timing pulses. In some embodiments, the UWB transmitter is configured to transmit blink data comprising information packets sized to approximately 112 bits.

In another embodiment, an apparatus for monitoring a participant is provided, the apparatus comprising at least one processor and at least one memory including computer program instructions, the at least one memory and the computer program instructions configured to, in cooperation with the at least one processor, cause the apparatus to correlate at least one tag to the participant, receive blink data transmitted by the at least one tag, determine tag location data based on the blink data, receive participant role data, compare the tag location data to participant dynamics/kinetics models based at least in part on the participant role data, and determine participant location data based on the comparing the tag location data to the participant dynamics/kinetics models.

In some embodiments, the tag comprises an ultra-wide-band (UWB) transmitter. In some embodiments, determining tag location data comprises determining a first tag derived data component and a second tag derived data component, and wherein the determining participant location data comprises determining participant location data by assigning a first weight to the first tag derived data component and a second weight to the second tag derived data component.

In some embodiments, determining participant location data comprises assigning the first weight to the first tag derived data component and the second weight to the second tag derived data component at a first time period, and further comprises assigning a third weight to the first tag derived data component and assigning a fourth weight to the second tag derived data component at a second time period. In some embodiments, the at least one memory and the computer program instructions may be further configured to, in cooperation with the at least one processor, cause the apparatus to receive field data, compare the participant location data to formation models based at least in part on the participant role data and the field data, and determine formation data based on the comparing the participant location data to the formation models.

In some embodiments, the participant location data comprises a first participant component and a second participant component, and wherein the determining formation data comprises determining formation data by assigning a first weight to the first participant component and a second weight to the second participant component. In some embodiments, the determining participant location data comprises assigning the first weight to the first participant component and the second weight to the second participant component at a first time period, and further comprises assigning a third weight to the first participant component at a second time period and assigning a fourth weight to the second participant component at the second time period. In some embodiments, the participant dynamics/kinetics models comprise location history data for the participant.

In some embodiments, the at least one memory and the computer program instructions are further configured to, in cooperation with the at least one processor, cause the apparatus to update the participant role data based on the participant location data. In some embodiments, the at least one memory and the computer program instructions are further configured to, in cooperation with the at least one processor, cause the apparatus to update the dynamics/kinetics models based on the participant location data. In some embodiments, the at least one memory and the computer program instructions are further configured to, in cooperation with the at least one processor, cause the apparatus to update the formation models based on the formation data. In some embodiments, the blink data comprises a plurality of time of arrival (TOA) timing pulses. In some embodiments, the blink data comprises information packets sized to approximately 112 bits.

In another embodiment, a computer program product for monitoring a participant may be provided, the computer program product may comprise a non-transitory computer readable storage medium and computer program instructions stored therein, the computer program instructions comprising program instructions at least configured to correlate at least one tag to the participant, receive blink data transmitted by the at least one tag, determine tag location data based on the blink data, receive participant role data, compare the tag location data to participant dynamics/kinetics models based at least in part on the participant role data, and determine participant location data based on the comparing the tag location data to the participant dynamics/kinetics models. In some embodiments, the tag comprises an ultra-wideband (UWB) transmitter.

In some embodiments, determining tag location data comprises determining a first tag derived data component and a second tag derived data component, and wherein the determining participant location data comprises determining participant location data by assigning a first weight to the first tag derived data component and a second weight to the second tag derived data component. In some embodiments, determining participant location data comprises assigning the first weight to the first tag derived data component and the second weight to the second tag derived data component at a first time period, and further comprises assigning a third weight to the first tag derived data component and assigning a fourth weight to the second tag derived data component at a second time period.

In some embodiments, the computer program instructions may be further configured to receive field data, compare the participant location data to formation models based at least in part on the participant role data and the field data, and determine formation data based on the comparing the participant location data to the formation models. In some embodiments, the participant location data comprises a first participant component and a second participant component, and wherein the determining formation data comprises determining formation data by assigning a first weight to the first participant component and a second weight to the second participant component.

In some embodiments, the determining participant location data comprises assigning the first weight to the first participant component and the second weight to the second participant component at a first time period, and further comprises assigning a third weight to the first participant component at a second time period and assigning a fourth weight to the second participant component at the second time period. In some embodiments, the participant dynamics/kinetics models comprise location history data for the participant. In some embodiments, the computer program instructions may be further configured to update the participant role data based on the participant location data. In some embodiments, the computer program instructions may be further configured to update the dynamics/kinetics models based on the participant location data. In some embodiments, the computer program instructions may be further configured to update the formation models based on the formation data. In some embodiments, the blink data comprises a plurality of time of arrival (TOA) timing pulses. In some embodiments, the blink data comprises information packets sized to approximately 112 bits.

In one embodiment, a method is provided for monitoring a participant that at least includes correlating at least one tag to the participant, receiving blink data transmitted by the at least one tag, determining tag location data based on the blink data, correlating a sensor to the participant, and receiving sensor derived data. The method further includes receiving participant role data, comparing the tag location data to participant dynamics/kinetics models based at least in part on the participant role data, and determining the participant location data based on comparing the tag location data and the sensor derived data to the participant dynamics/kinetics models.

In some embodiments, the sensor may comprise one or more of an accelerometer, a magnetometer, and a time-of-flight sensor. In some embodiments, determining participant location data comprises determining participant location data by assigning a first weight to the tag location data and a second weight to the sensor derived data.

In some embodiments, determining participant location data comprises assigning a first weight to the tag location data and a second weight to the sensor derived data at a first time period, and assigning a third weight to the tag location data at a second time period and a fourth weight to the sensor derived data at the second time period.

In some embodiments, determining the tag location data comprises determining a first tag derived data component and a second tag derived data component, wherein the sensor derived data comprises a first sensor derived data component and a second sensor derived data component, wherein the determining participant location data comprises determining participant location data by assigning a first weight to the first tag derived data component, a second weight to the second tag derived data component, a third weight to the first sensor derived data component, and a fourth weight to the second sensor derived data component.

In some embodiments, determining participant location data comprises assigning at a first time period the first weight to the first tag derived data component, the second weight to the second tag derived data component, the third weight to the first sensor derived data component, and the fourth weight to the second sensor derived data component, and at a second time period assigning a fifth weight to the first tag derived data component, a sixth weight to the second tag derived data component, a seventh weight to the first sensor derived data component, and an eighth weight to the second sensor derived data component.

In some embodiments, the method may further comprise receiving field data, comparing the participant location data to formation models based at least in part on the participant role data and the field data, and determining formation data based on the comparing the participant location data to the formation models.

In some embodiments, the participant location data may comprise a first participant component and a second participant component, and determining formation data may comprise determining formation data by assigning a first weight to the first participant component and a second weight to the second participant component.

In some embodiments, determining participant location data comprises assigning the first weight to the first participant component and the second weight to the second participant component at a first time period, and further comprises assigning a third weight to the first participant component at a second time period and assigning a fourth weight to the second participant component at the second time period.

In some embodiments, the method may further comprise comparing the formation data and participant location data to play models, and determining play data based on the comparing the formation data and participant location data to the play models.

In some embodiments, the formation data comprises a first formation component and a second formation component, and determining play data may comprise determining play data by assigning a first weight to the first formation component and a second weight to the second formation component.

In some embodiments, determining play data comprises assigning the first weight to the first formation component and the second weight to the second formation component at a first time period, and further comprises assigning a third weight to the first formation component at a second time period and assigning a fourth weight to the second formation component at the second time period.

In some embodiments, the method may further comprise determining that the participant is a player, and receiving the tag location data to a player dynamics engine, wherein the participant role data is player role data received to the player dynamics engine, wherein the participant dynamics/kinetics models are player dynamics/kinetics models, and wherein the player dynamics engine compares the tag location data to the player dynamics/kinetics models based at least in part on the player role data.

In some embodiments, the method may further comprise determining that the participant is an official, and receiving the tag location data to an official dynamics engine, wherein the participant role data is official role data received to the official dynamics engine, wherein the participant dynamics/kinetics models are official dynamics/kinetics models, and wherein the official dynamics engine compares the tag location data to the official dynamics/kinetics models based at least in part on the official role data.

In some embodiments, the method may further comprise determining that the participant is a ball, and receiving the tag location data to a ball engine, wherein the participant role data is ball role data received to the ball engine, wherein the participant dynamics/kinetics models are ball dynamics/kinetics models, and wherein the ball engine compares the tag location data to the ball dynamics/kinetics models based at least in part on the ball role data.

In some embodiments, the method may further comprise determining that the participant is a field marker, and receiving the tag data to a field marker engine, wherein the participant role data is field marker role data received to the field marker engine, wherein the participant dynamics/kinetics models are field marker dynamics/kinetics models, and wherein the field marker engine compares the tag location data to the field marker dynamics/kinetics models based at least in part on the field marker role data.

In some embodiments, the sensor derived data comprises time-of-flight sensor data and the method may further comprise correlating the time-of-flight sensor data to the participant. In some embodiments, the sensor derived data comprises time-of-flight sensor data and the method may further comprise assigning a first weight to the tag location data and a second weight to the time-of-flight sensor data.

In another embodiment, an apparatus is provided comprising at least one processor and at least one memory including computer program instructions, the at least one memory and the computer program instructions configured to, in cooperation with the at least one processor, cause the apparatus to correlate at least one tag to the participant, receive blink data transmitted by the at least one tag, determine tag location data based on the blink data, correlate a sensor to the participant, receive sensor derived data, receive participant role data, compare the tag location data to participant dynamics/kinetics models based at least in part on the participant role data, and determine the participant location data based on comparing the tag location data and the sensor derived data to the participant dynamics/kinetics models.

In some embodiments, the sensor comprises one or more of an accelerometer, a magnetometer, and a time-of-flight sensor. In some embodiments, determining participant location data comprises determining participant location data by assigning a first weight to the tag location data and a second weight to the sensor derived data.

In some embodiments, determining participant location data comprises assigning a first weight to the tag location data and a second weight to the sensor derived data at a first time period, and assigning a third weight to the tag location data at a second time period and a fourth weight to the sensor derived data at the second time period.

In some embodiments, determining the tag location data comprises determining a first tag derived data component and a second tag derived data component, wherein the sensor derived data comprises a first sensor derived data component and a second sensor derived data component, wherein the determining participant location data comprises determining participant location data by assigning a first weight to the first tag derived data component, a second weight to the second tag derived data component, a third weight to the first sensor derived data component, and a fourth weight to the second sensor derived data component.

In some embodiments, determining participant location data comprises assigning at a first time period the first weight to the first tag derived data component, the second weight to the second tag derived data component, the third weight to the first sensor derived data component, and the fourth weight to the second sensor derived data component, and at a second time period assigning a fifth weight to the first tag derived data component, a sixth weight to the second tag derived data component, a seventh weight to the first sensor derived data component, and an eighth weight to the second sensor derived data component.

In some embodiments, the apparatus may further comprise the at least one memory and the computer program instructions configured to, in cooperation with the at least one processor, cause the apparatus to receive field data, compare the participant location data to formation models based at least in part on the participant role data and the field data, and determine formation data based on the comparing the participant location data to the formation models.

In some embodiments, the participant location data comprises a first participant component and a second participant component, and wherein the determining formation data comprises determining formation data by assigning a first weight to the first participant component and a second weight to the second participant component.

In some embodiments, determining participant location data comprises assigning the first weight to the first participant component and the second weight to the second participant component at a first time period, and further comprises assigning a third weight to the first participant component at a second time period and assigning a fourth weight to the second participant component at the second time period.

In some embodiments, the apparatus may further comprise the at least one memory and the computer program instructions configured to, in cooperation with the at least one processor, cause the apparatus to compare the formation data and participant location data to play models, and determine play data based on the comparing the formation data and participant location data to the play models.

In some embodiments, the formation data comprises a first formation component and a second formation component, and wherein the determining play data comprises determining play data by assigning a first weight to the first formation component and a second weight to the second formation component.

In some embodiments, determining play data comprises assigning the first weight to the first formation component and the second weight to the second formation component at a first time period, and further comprises assigning a third weight to the first formation component at a second time period and assigning a fourth weight to the second formation component at the second time period.

In some embodiments, the apparatus may further comprise the at least one memory and the computer program instructions configured to, in cooperation with the at least one processor, cause the apparatus to determine that the participant is a player, and receive the tag location data to a player dynamics engine, wherein the participant role data is player role data received to the player dynamics engine, wherein the participant dynamics/kinetics models are player dynamics/kinetics models, and wherein the player dynamics engine compares the tag location data to the player dynamics/kinetics models based at least in part on the player role data.

In some embodiments, the apparatus may further comprise the at least one memory and the computer program instructions configured to, in cooperation with the at least one processor, cause the apparatus to determine that the participant is an official, and receive the tag location data to an official dynamics engine, wherein the participant role data is official role data received to the official dynamics engine, wherein the participant dynamics/kinetics models are official dynamics/kinetics models, and wherein the official dynamics engine compares the tag location data to the official dynamics/kinetics models based at least in part on the official role data.

In some embodiments, the apparatus may further comprise the at least one memory and the computer program instructions configured to, in cooperation with the at least one processor, cause the apparatus to determine that the participant is a ball, and receive the tag location data to a ball engine, wherein the participant role data is ball role data received to the ball engine, wherein the participant dynamics/kinetics models are ball dynamics/kinetics models, and wherein the ball engine compares the tag location data to the ball dynamics/kinetics models based at least in part on the ball role data.

In some embodiments, the apparatus may further comprise the at least one memory and the computer program instructions configured to, in cooperation with the at least one processor, cause the apparatus to determine that the participant is a field marker, and receive the tag data to a field marker engine, wherein the participant role data is field marker role data received to the field marker engine, wherein the participant dynamics/kinetics models are field marker dynamics/kinetics models, and wherein the field marker engine compares the tag location data to the field marker dynamics/kinetics models based at least in part on the field marker role data.

In some embodiments, the sensor derived data may comprise time-of-flight sensor data and the apparatus may further comprise the at least one memory and the computer program instructions configured to, in cooperation with the at least one processor, cause the apparatus to correlate the time-of-flight sensor data to the participant. In some embodiments, the sensor derived data may comprise time-of-flight sensor data and the apparatus may further comprise the at least one memory and the computer program instructions configured to, in cooperation with the at least one processor, cause the apparatus to assign a first weight to the tag location data and a second weight to the time-of-flight sensor data.

In another embodiment, a computer program product is provided for monitoring a participant, the computer program product comprising a non-transitory computer readable storage medium and computer program instructions stored therein, the computer program instructions comprising program instructions at least configured to correlate at least one tag to the participant, receive blink data transmitted by the at least one tag, determine tag location data based on the blink data, correlate a sensor to the participant, receive sensor derived data, receive participant role data, compare the tag location data to participant dynamics/kinetics models based at least in part on the participant role data, and determine the participant location data based on comparing the tag location data and the sensor derived data to the participant dynamics/kinetics models.

In some embodiments, the sensor may comprise one or more of an accelerometer, a magnetometer, and a time-of-flight sensor. In some embodiments, the computer program product may further comprise the computer program instructions at least configured to receive field data, compare the participant location data to formation models based at least in part on the participant role data and the field data, and determine formation data based on the comparing the participant location data to the formation models.

In some embodiments, the computer program product may further comprise the computer program instructions at least configured to compare the formation data and participant location data to play models, and determine play data based on the comparing the formation data and participant location data to the play models.

In some embodiments, the computer program product may further comprise the computer program instructions at least configured to determine that the participant is a player, and receive the tag location data to a player dynamics engine, wherein the participant role data is player role data received to the player dynamics engine, wherein the participant dynamics/kinetics models are player dynamics/kinetics models, and wherein the player dynamics engine compares the tag location data to the player dynamics/kinetics models based at least in part on the player role data.

In some embodiments, the computer program product may further comprise the computer program instructions at least configured to determine that the participant is an official, and receive the tag location data to an official dynamics engine, wherein the participant role data is official role data received to the official dynamics engine, wherein the participant dynamics/kinetics models are official dynamics/kinetics models, and wherein the official dynamics engine compares the tag location data to the official dynamics/kinetics models based at least in part on the official role data.

In some embodiments, the computer program product may further comprise the computer program instructions at least configured to determine that the participant is a ball, and receive the tag location data to a ball engine, wherein the participant role data is ball role data received to the ball engine, wherein the participant dynamics/kinetics models are ball dynamics/kinetics models, and wherein the ball engine compares the tag location data to the ball dynamics/kinetics models based at least in part on the ball role data.

In some embodiments, the computer program product may further comprise the computer program instructions at least configured to determine that the participant is a field marker, and receive the tag data to a field marker engine, wherein the participant role data is field marker role data received to the field marker engine, wherein the participant dynamics/kinetics models are field marker dynamics/kinetics models, and wherein the field marker engine compares the tag location data to the field marker dynamics/kinetics models based at least in part on the field marker role data.

In some embodiments, the sensor derived data may comprise time-of-flight sensor data and the computer program product may further comprise the computer program instructions at least configured to correlate the time-of-flight sensor data to the participant. In some embodiments, the sensor derived data may comprise time-of-flight sensor data and the computer program product may further comprise the computer program instructions at least configured to assign a first weight to the tag location data and a second weight to the time-of-flight sensor data.

In another embodiment, a system is provided for monitoring a participant comprising one or more tags and an apparatus. The apparatus may comprise at least one processor and at least one memory including computer program instructions, the at least one memory and the computer program instructions configured to, in cooperation with the at least one processor, cause the apparatus to correlating at least one tag to the participant, receiving blink data transmitted by the at least one tag, determining tag location data based on the blink data, correlating a sensor to the participant, receiving sensor derived data, receiving participant role data, comparing the tag location data to participant dynamics/kinetics models based at least in part on the participant role data, and determining the participant location data based on comparing the tag location data and the sensor derived data to the participant dynamics/kinetics models.

In one embodiment, a method is provided for monitoring a participant that at least includes correlating at least one tag to the participant, receiving blink data transmitted by the at least one tag, and determining tag location data based on the blink data. The method further includes receiving participant role data, comparing the tag location data to participant dynamics/kinetics models based at least in part on the participant role data, and determining participant location data based on the comparing the tag location data to the participant dynamics/kinetics models.

In some embodiments, the method may further comprise receiving field data, comparing the participant location data to formation models based at least in part on the participant role data and the field data, and determining formation data based on the comparing the participant location data to the formation models, and determining a probable play based on comparing the formation data to play models. In some embodiments, determining the probable play is based on generating a probable play ranked list.

In another embodiment, a method is provided for monitoring a participant that at least includes correlating at least one tag to the participant, receiving blink data transmitted by the at least one tag, determining tag location data based on the blink data, receiving participant role data, receiving weather data, comparing the tag location data to participant dynamics/kinetics models based at least in part on the participant role data, determining participant location data based on the comparing the tag location data to the participant dynamics/kinetics models, and updating stored weather-adjusted participant location data based on the participant location data and the weather data.

In some embodiments, the method may further comprise determining participant performance information based on comparing the participant location data and the weather data to the stored weather-adjusted participant location data.

In another embodiment, a method is provided for evaluating a player, the method comprising correlating at least one tag to the player, receiving blink data transmitted by the at least one tag, determining tag location data based on the blink data, receiving player role data, receiving weather data, comparing the tag location data to player dynamics/kinetics models based at least in part on the player role data, determining player location data based on the comparing the tag location data to the player dynamics/kinetics models, and determining player performance information based on comparing the player location data and the weather data to stored weather-adjusted player location data.

In another embodiment, an apparatus is provided for monitoring a participant comprising at least one processor and at least one memory including computer program instructions, the at least one memory and the computer program instructions configured to, in cooperation with the at least one processor, cause the apparatus to correlate at least one tag to the participant, receive blink data transmitted by the at least one tag, determine tag location data based on the blink data, receive participant role data, compare the tag location data to participant dynamics/kinetics models based at least in part on the participant role data, and determine participant location data based on the comparing the tag location data to the participant dynamics/kinetics models.

In some embodiments, the apparatus may further comprise the at least one memory and the computer program instructions configured to, in cooperation with the at least one processor, cause the apparatus to receive field data, compare the participant location data to formation models based at least in part on the participant role data and the field data, determine formation data based on the comparing the participant location data to the formation models, and determine a probable play based on comparing the formation data to play models. In some embodiments, determining the probable play is based on generating a probable play ranked list.

In some embodiments, the apparatus may further comprise the at least one memory and the computer program instructions configured to, in cooperation with the at least one processor, cause the apparatus to receive field data, compare the participant location data to formation models based at least in part on the participant role data and the field data, and determine formation data based on the comparing the participant location data to the formation models.

In another embodiment, an apparatus is provided for monitoring a participant comprising at least one processor and at least one memory including computer program instructions, the at least one memory and the computer program instructions configured to, in cooperation with the at least one processor, cause the apparatus to correlate at least one tag to the participant, receive blink data transmitted by the at least one tag, determine tag location data based on the blink data, receive participant role data, receive weather data, compare the tag location data to participant dynamics/kinetics models based at least in part on the participant role data, determine participant location data based on the comparing the tag location data to the participant dynamics/kinetics models, and update stored weather-adjusted participant location data based on the participant location data and the weather data.

In some embodiments, the apparatus may further comprise the at least one memory and the computer program instructions configured to, in cooperation with the at least one processor, cause the apparatus to determine participant performance information based on comparing the participant location data and the weather data to the stored weather-adjusted participant location data.

In another embodiment, an apparatus is provided for evaluating a player comprising at least one processor and at least one memory including computer program instructions, the at least one memory and the computer program instructions configured to, in cooperation with the at least one processor, cause the apparatus to correlate at least one tag to the player, receive blink data transmitted by the at least one tag, determine tag location data based on the blink data, receive player role data, receive weather data, compare the tag location data to player dynamics/kinetics models based at least in part on the player role data, determine player location data based on the comparing the tag location data to the player dynamics/kinetics models, and determine player performance information based on comparing the player location data and the weather data to stored weather-adjusted player location data.

In another embodiment, a computer program product is provided for monitoring a participant, the computer program product comprising a non-transitory computer readable storage medium and computer program instructions stored therein, the computer program instructions comprising program instructions at least configured to correlate at least one tag to the participant, receive blink data transmitted by the at least one tag, determine tag location data based on the blink data, receive participant role data, compare the tag location data to participant dynamics/kinetics models based at least in part on the participant role data, and determine participant location data based on the comparing the tag location data to the participant dynamics/kinetics models.

In some embodiments, the computer program product may further comprise the computer program instructions at least configured to receive field data, compare the participant location data to formation models based at least in part on the participant role data and the field data, and determine formation data based on the comparing the participant location data to the formation models. In some embodiments, the computer program product may further comprise the computer program instructions at least configured to determine a probable play based on comparing the formation data to play models. In some embodiments, determining the probable play is based on generating a probable play ranked list.

In another embodiment, a computer program product is provided for monitoring a participant, the computer program product comprising a non-transitory computer readable storage medium and computer program instructions stored therein, the computer program instructions comprising program instructions at least configured to correlate at least one tag to the participant, receive blink data transmitted by the at least one tag, determine tag location data based on the blink data, receive participant role data, receive weather data, compare the tag location data to participant dynamics/kinetics models based at least in part on the participant role data, determine participant location data based on the comparing the tag location data to the participant dynamics/kinetics models, and update stored weather-adjusted participant location data based on the participant location data and the weather data.

In some embodiments, the computer program product may further comprise the computer program instructions at least configured to determine participant performance information based on comparing the participant location data and the weather data to the stored weather-adjusted participant location data.

In another embodiment, a computer program product is provided for evaluating a player, the computer program product comprising a non-transitory computer readable storage medium and computer program instructions stored therein, the computer program instructions comprising program instructions at least configured to correlate at least one tag to the player, receive blink data transmitted by the at least one tag, determine tag location data based on the blink data, receive player role data, receive weather data, compare the tag location data to player dynamics/kinetics models based at least in part on the player role data, determine player location data based on the comparing the tag location data to the player dynamics/kinetics models, and determine player performance information based on comparing the player location data and the weather data to stored weather-adjusted player location data.

In one embodiment, a method is provided for generating formation data that at least includes receiving participant location data determined based on tag derived data and participant role data; receiving field data; comparing the participant location data to formation models based at least in part on the participant location data, the participant role data, and the field data; and determining formation data based on the comparing the participant location data to the formation models.

In some embodiments, the method may further include comparing the participant location data to play models based at least in part on the participant role data, the field data, and the formation data; and determining play data based on the comparing the participant location data and the formation data to the play models. In some embodiments, the method may further include updating the formation models based on the formation data.

In another embodiment, a method is provided for monitoring a participant that at least includes correlating at least one tag to the participant; correlating at least one sensor to the participant; receiving blink data associated with the at least one tag; receiving sensor derived data associated with the at least one sensor; determining tag location data based at least on the blink data; comparing the tag location data and the sensor derived data to participant dynamics/kinetics models; determining participant location data based on the comparing the tag location data and the sensor derived data to the participant dynamics/kinetics models; and determining participant role data based on the determining participant location data. In some embodiments, the method may further include updating the dynamics/kinetics models based on the participant location data.

In another embodiment, a method is provided for generating play data that at least includes receiving participant location data determined based on tag location data, sensor derived data, and participant role data; receiving formation data and field data; comparing the participant location data and formation data to play models based at least in part on the participant role data and the field data; and determining play data based on the comparing the participant location data and the formation data to the play models. In some embodiments, the method may further include updating the play models based on the play data.

In another embodiment, a method is provided for generating sporting event analytics comprising receiving participant location data; receiving participant role data; receiving formation data; receiving play data; determining output events based at least in part on the participant location data, the participant role data, the formation data, and the play data; storing the output events in a data store; and providing at least some of the output events to one or more analytics systems or control systems.

In another embodiment, an apparatus is provided for generating formation data comprising at least one processor and at least one memory including computer program instructions, the at least one memory and the computer program instructions configured to, in cooperation with the at least one processor, cause the apparatus to receive participant location data determined based on tag derived data and participant role data; receive field data; compare the participant location data to formation models based at least in part on the participant location data, the participant role data, and the field data; and determine formation data based on the comparing the participant location data to the formation models.

In some embodiments, the apparatus may further comprise the at least one memory and the computer program instructions configured to, in cooperation with the at least one processor, cause the apparatus to compare the participant location data to play models based at least in part on the participant role data, the field data, and the formation data; and determine play data based on the comparing the participant location data and the formation data to the play models.

In another embodiment, an apparatus is provided for monitoring a participant comprising at least one processor and at least one memory including computer program instructions, the at least one memory and the computer program instructions configured to, in cooperation with the at least one processor, cause the apparatus to correlate at least one tag to the participant; correlate at least one sensor to the participant; receive blink data associated with the at least one tag; receive sensor derived data associated with the at least one sensor; determine tag location data based at least on the blink data; compare the tag location data and the sensor derived data to participant dynamics/kinetics models; determine participant location data based on the comparing the tag location data and the sensor derived data to the participant dynamics/kinetics models; and determine participant role data based on the determining participant location data.

In another embodiment, an apparatus is provided for generating play data comprising at least one processor and at least one memory including computer program instructions, the at least one memory and the computer program instructions configured to, in cooperation with the at least one processor, cause the apparatus to receive participant location data determined based on tag location data, sensor derived data, and participant role data; receive formation data and field data; compare the participant location data and formation data to play models based at least in part on the participant role data and the field data; and determine play data based on the comparing the participant location data and the formation data to the play models.

In another embodiment, an apparatus is provided for generating sporting event analytics comprising at least one processor and at least one memory including computer program instructions, the at least one memory and the computer program instructions configured to, in cooperation with the at least one processor, cause the apparatus to receive participant location data; receive participant role data; receive formation data; receive play data; determine output events based at least in part on the participant location data, the participant role data, the formation data, and the play data; store the output events in a data store; and provide at least some of the output events to one or more analytics systems or control systems.

In another embodiment, a computer program product is provided for generating formation data, the computer program product comprising a non-transitory computer readable storage medium and computer program instructions stored therein, the computer program instructions comprising program instructions at least configured to receive participant location data determined based on tag derived data and participant role data; receive field data; compare the participant location data to formation models based at least in part on the participant location data, the participant role data, and the field data; and determine formation data based on the comparing the participant location data to the formation models.

In some embodiments, the computer program product may further comprise the computer program instructions at least configured to compare the participant location data to play models based at least in part on the participant role data, the field data, and the formation data; and determine play data based on the comparing the participant location data and the formation data to the play models.

In another embodiment, a computer program product is provided for monitoring a participant, the computer program product comprising a non-transitory computer readable storage medium and computer program instructions stored therein, the computer program instructions comprising program instructions at least configured to correlate at least one tag to the participant; correlate at least one sensor to the participant; receive blink data associated with the at least one tag; receive sensor derived data associated with the at least one sensor; determine tag location data based at least on the blink data; compare the tag location data and the sensor derived data to participant dynamics/kinetics models; determine participant location data based on the comparing the tag location data and the sensor derived data to the participant dynamics/kinetics models; and determine participant role data based on the determining participant location data.

In another embodiment, a computer program product is provided for generating play data, the computer program product comprising a non-transitory computer readable storage medium and computer program instructions stored therein, the computer program instructions comprising program instructions at least configured to receive participant location data determined based on tag location data, sensor derived data, and participant role data; receive formation data and field data; compare the participant location data and formation data to play models based at least in part on the participant role data and the field data; and determine play data based on the comparing the participant location data and the formation data to the play models.

In another embodiment, a computer program product is provided for generating sporting event analytics, the computer program product comprising a non-transitory computer readable storage medium and computer program instructions stored therein, the computer program instructions comprising program instructions at least configured to receive participant location data; receive participant role data; receive formation data; receive play data; determine output events based at least in part on the participant location data, the participant role data, the formation data, and the play data; store the output events in a data store; and provide at least some of the output events to one or more analytics systems or control systems.

In one embodiment, a method is provided for evaluating a player that at least includes correlating at least one tag to the player, receiving blink data transmitted by the at least one tag, and determining tag location data based on the blink data. The method further includes receiving player role data, comparing the tag location data to player dynamics/kinetics models based at least in part on the player role data, determining player location data based on the comparing the tag location data to the player dynamics/kinetics models, and determining player performance information based on comparing the player location data to stored player location data.

In some embodiments, the stored player location data may be based on prior activity of the player. In some embodiments, the stored player location data may be based on prior activity of another player. In some embodiments, the stored player location data may be based on prior activity of the player and another player. In some embodiments, the stored player location data may be based on prior activity of the player and an adversary.

In some embodiments, determining player performance information may include determining a player health profile based, at least in part, on comparing the player location data to the stored player location data. In some embodiments, the method may further comprise receiving sensor derived data.

In another embodiment, a method is provided for evaluating an official that at least includes correlating at least one tag to the official, receiving blink data transmitted by the at least one tag, and determining tag location data based on the blink data. The method further includes receiving official role data, comparing the tag location data to official dynamics/kinetics models based at least in part on the official role data, determining official location data based on the comparing the tag location data to the official dynamics/kinetics models, and determining official performance information based on comparing the official location data to stored official location data.

In another embodiment, an apparatus for evaluating a player is provided that comprises at least one processor and at least one memory including computer program instructions, the at least one memory and the computer program instructions configured to, in cooperation with the at least one processor cause the apparatus to correlate at least one tag to the player, receive blink data transmitted by the at least one tag, and determine tag location data based on the blink data. The apparatus is further configured to receive player role data, compare the tag location data to player dynamics/kinetics models based at least in part on the player role data, determine player location data based on the comparing the tag location data to the player dynamics/kinetics models, and determine player performance information based on comparing the player location data to stored player location data. In some embodiments, the at least one memory and the computer program instructions configured to, in cooperation with the at least one processor, cause the apparatus to further receive environmental measurements transmitted by a sensor.

In another embodiment, an apparatus for evaluating an official is provided that comprises at least one processor and at least one memory including computer program instructions, the at least one memory and the computer program instructions configured to, in cooperation with the at least one processor, cause the apparatus to correlate at least one tag to the official, receive blink data transmitted by the at least one tag, and determine tag location data based on the blink data. The apparatus is further configured to receive official role data, compare the tag location data to official dynamics/kinetics models based at least in part on the official role data, determine official location data based on the comparing the tag location data to the official dynamics/kinetics models, and determine official performance information based on comparing the official location data to stored official location data.

In a further embodiment, a computer program product for evaluating a player is provided, the computer program product comprising a non-transitory computer readable storage medium and computer program instructions stored therein, the computer program instructions comprising program instructions at least configured to correlate at least one tag to the player, receive blink data transmitted by the at least one tag, and determine tag location data based on the blink data. The computer program instructions further configured to receive player role data, compare the tag location data to player dynamics/kinetics models based at least in part on the player role data, determine player location data based on the comparing the tag location data to the player dynamics/kinetics models, and determine player performance information based on comparing the player location data to stored player location data. The computer program instructions further configured to receive environmental measurements transmitted by a sensor.

In another embodiment, a computer program product for evaluating an official is provided, the computer program product comprising a non-transitory computer readable storage medium and computer program instructions stored therein, the computer program instructions comprising program instructions at least configured to correlate at least one tag to the official, receive blink data transmitted by the at least one tag, and determine tag location data based on the blink data. The computer program instructions further configured to receive official role data, compare the tag location data to official dynamics/kinetics models based at least in part on the official role data, determine official location data based on the comparing the tag location data to the official dynamics/kinetics models, and determine official performance information based on comparing the official location data to stored official location data.

In a further embodiment, a system for evaluating a player is provided which comprises one or more tags and an apparatus comprising at least one processor and at least one memory including computer program instructions, the at least one memory and the computer program instructions configured to, in cooperation with the at least one processor, cause the apparatus to correlate at least one tag to the player, receive blink data transmitted by the at least one tag, and determine tag location data based on the blink data. The apparatus is further configured to receive player role data, compare the tag location data to player dynamics/kinetics models based at least in part on the player role data, determine player location data based on the comparing the tag location data to the player dynamics/kinetics models, and determine player performance information based on comparing the player location data to stored player location data. In some embodiments, the system may further comprise one or more sensors.

In another embodiment, a system for evaluating an official is provided which comprises one or more tags and an apparatus comprising at least one processor and at least one memory including computer program instructions, the at least one memory and the computer program instructions configured to, in cooperation with the at least one processor, cause the apparatus to correlate at least one tag to the official, receive blink data transmitted by the at least one tag, and determine tag location data based on the blink data. The apparatus is further configured to receive official role data, compare the tag location data to official dynamics/kinetics models based at least in part on the official role data, determine official location data based on the comparing the tag location data to the official dynamics/kinetics models, and determine official performance information based on comparing the official location data to stored official location data.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 illustrates an exemplary environment using a radio frequency locating system for providing performance analytics in accordance with some embodiments of the present invention;

FIGS. 2A-C illustrate some exemplary participants carrying tags and sensors that may provide information to a performance analytics system in accordance with some embodiments of the present invention;

FIGS. 3A-3E are block diagrams showing the input and output of receivers and sensor receivers in accordance with an example embodiment;

Figure 11:
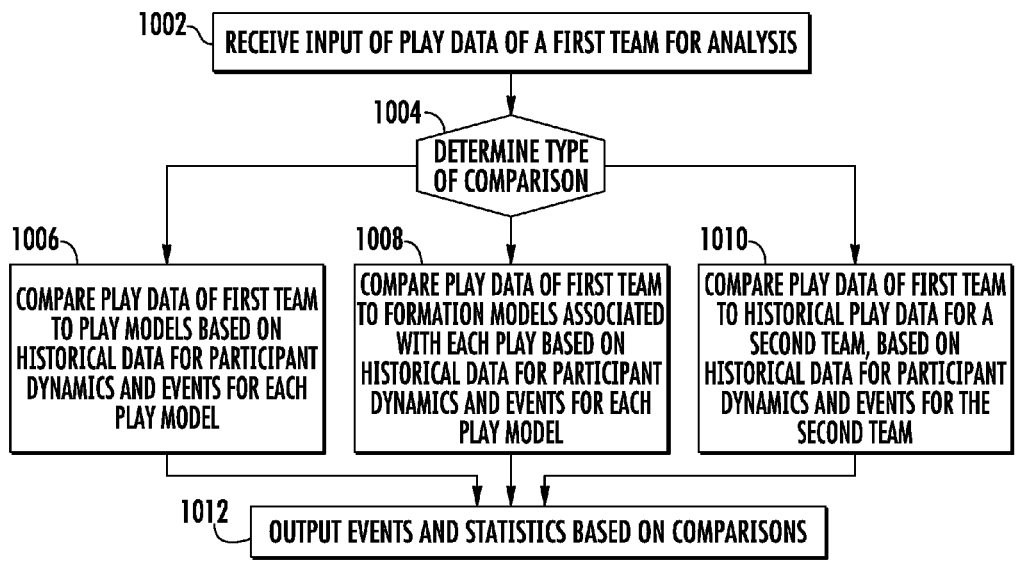
Figure 12:
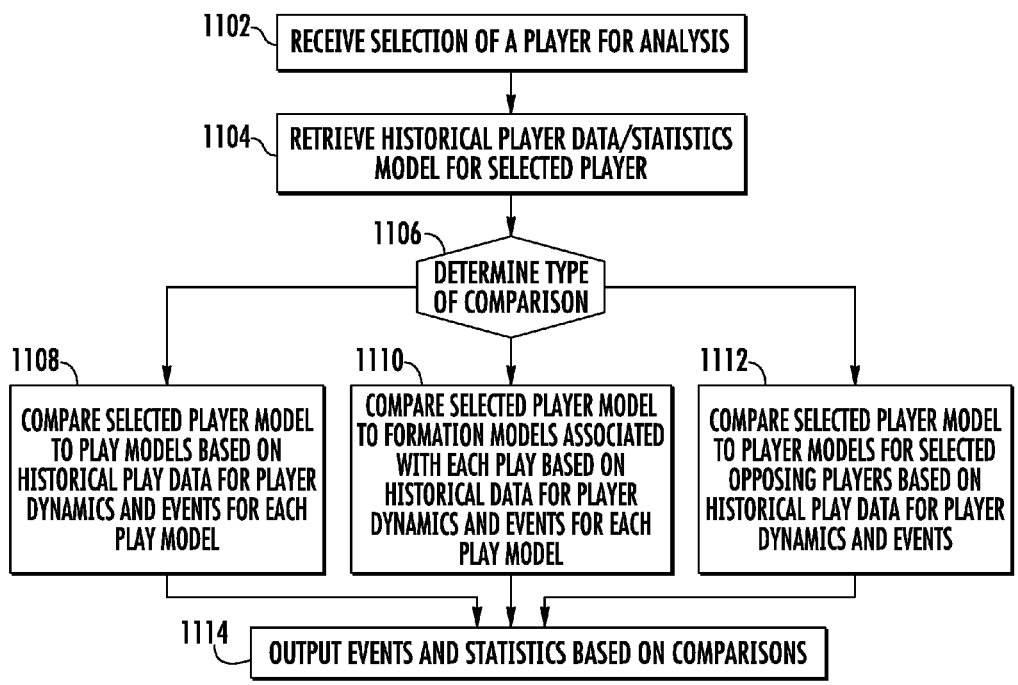
Figure 13:
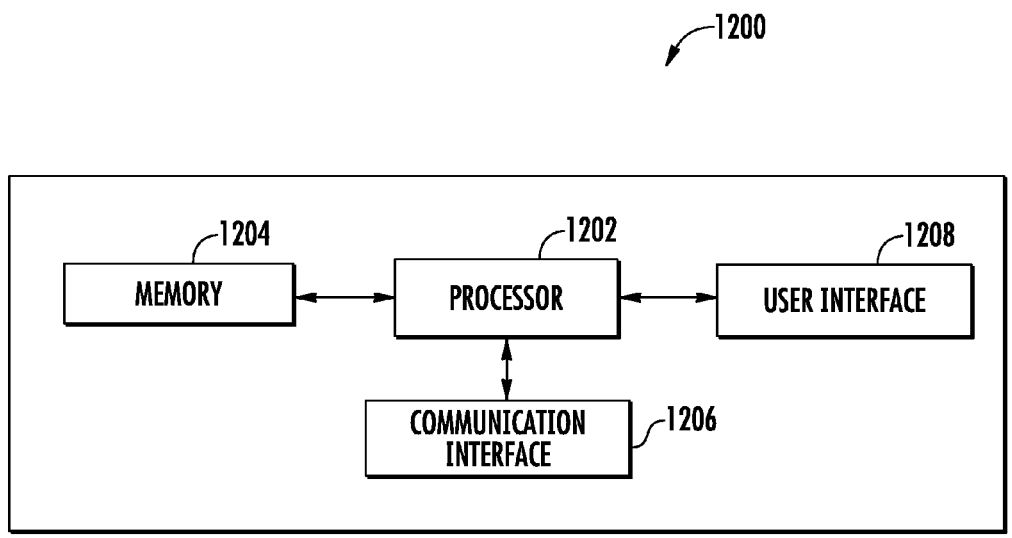

FIGS. 6A-12 provide flowcharts of some exemplary processes that may be used in providing performance analytics in accordance with some embodiments of the present invention; and FIG. 13 illustrates a block diagram of components that may be included in devices for performing operations in accordance with some embodiments of the present invention.

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Overview

Existing performance analytics of sporting events have drawbacks in providing accurate data about events and participant actions that occur during a game. Game day data is often manually collected by individuals documenting participant actions and play participation during a game. Performance review of a game often requires individuals to manually review game recordings over a number of hours after a game to compile player actions and events during play. This performance review is also often limited to statistics and data that can be identified or captured by the individuals watching or reviewing a game or game film. In addition, such review and any analytics data flowing therefrom is provided freely on a non-exclusive basis as anyone with access to game film can compile similar analytics data.

Embodiments of the present invention are directed to methods, systems, apparatuses, and computer readable storage media for providing real-time collection of data and analysis of participant performance and play statistics during a game such as by using radio frequency locating systems and radio frequency identification ("RFID").

Embodiments of the present invention may provide for automatic recognition of formations, plays, and events through the processing of real time data (or near real time data) regarding location, change in location, velocity, change in acceleration, orientation, or the like, for participants based on an analysis of relevant models and data as described in detail below. The term "participant" as used herein refers to players, officials, game related objects such as the ball, penalty markers, line of scrimmage and yard to gain markers, and any other movable object proximate a field of play.

In embodiments where participants are players, a group or plurality of participants may be grouped into squads (e.g., offense, defense, kickoff, punt, kick return, punt return, field goal, infield, outfield, bullpen, etc.) and/or teams (e.g., football team, baseball team, swim team, etc.). Participants on the same team are called team mates; participants on different teams are called adversaries.

Embodiments of the present invention may provide for automated data collection with reduced errors, as well as providing additional statistics that may not be available with current systems. Additionally, embodiments may provide for rapid (i.e., near instantaneous) production of game review documentation (e.g., playbooks). Embodiments of the present invention may also provide additional and exclusive data and analysis that may be securely licensed without concern that similar analytics may be readily reproduced without a system configured as set forth below.

Embodiments of the present invention may allow for the simultaneous tracking of a plurality of participants and may provide for indications of player statistics and/or potential play events in real time (or near real time). Such indications may be output to a variety of systems including, without limitation, a visualization system (e.g., an enhanced television broadcast system or computer graphics visualization system), a game operations system, a camera control system, a team analytics system, a league analytics system, and a statistics system.

Embodiments of the present invention are illustrated in the appended figures and description below in relation to the sport of American football. However, as will be apparent to one of ordinary skill in the art in view of this disclosure, the inventive concepts herein described are not limited to football and may be applied to various other applications including, without limitation, other sports or group events such as baseball, basketball, golf, hockey, soccer, racing or motorsports, competitive events, and the like.

Example RF Locating System Architecture

Figure 1:
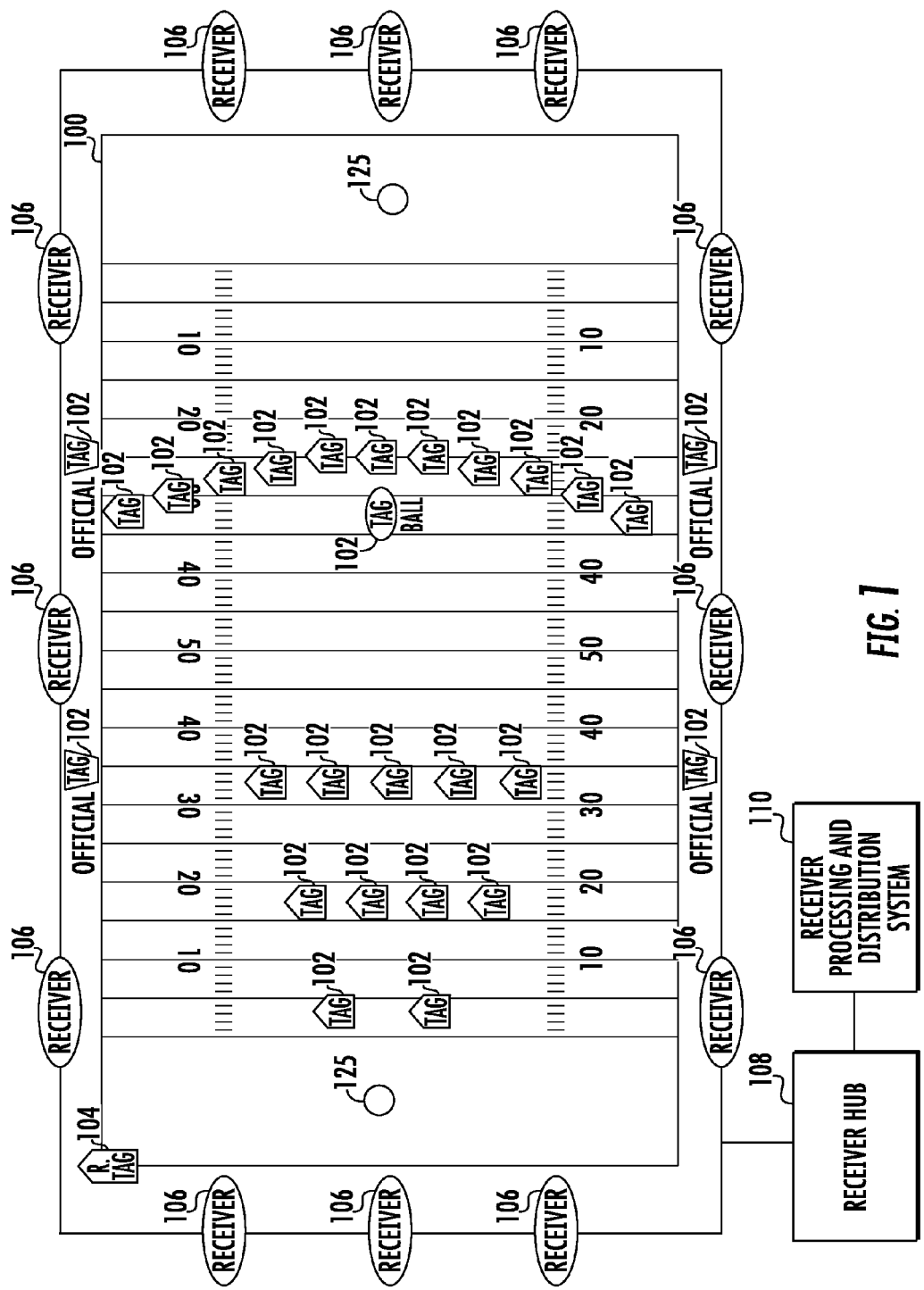

FIG. 1 illustrates a radio frequency locating system useful for determining the location of an object (e.g. a football player on a football field) by determining RF location tag 102 (e.g., a ultra-wide band (UWB) location tag) location information at each receiver 106 (e.g., UWB reader, etc.); a timing reference clock to synchronize the frequency of counters within each receiver 106; and, in some examples, a reference tag 104, preferably a UWB transmitter, positioned at known coordinates to enable phase offset between counters to be determined. The systems described herein may be referred to as either "multilateration" or "geolocation" systems; terms which refer to the process of locating a signal source by solving for the mathematical intersection of multiple hyperbolae determined by the difference of arrival times of a signal received at multiple receivers.

In some examples, the system comprising at least the tags 102 and the receivers 106 is configured to provide two dimensional and/or three dimensional precision localization (e.g., subfoot resolutions), even in the presence of multipath interference, due in part to the use of short nanosecond duration pulses whose time-of-flight can be accurately determined using detection circuitry, such as in the receivers 106, which can trigger on the leading edge of a received waveform. In some examples, this short pulse characteristic allows necessary data to be conveyed by the system at a higher peak power, but lower overall power levels, than a wireless system configured for high data rate communications, yet still operate within local regulatory requirements which may limit overall power levels.

In some examples, the tags 102 may operate with an instantaneous −3 dB bandwidth of approximately 400 MHz and an average transmission rate below a 187.5 kHz regulatory cutoff. In such examples, the predicted maximum range of the system, operating at 6.0 GHz, is roughly 311 meters. Such a configuration advantageously satisfies constraints applied by regulatory bodies related to peak and average power densities (e.g., effective isotropic radiated power density), while still optimizing system performance related to range and interference. In further examples, tag transmissions with a −3 dB bandwidth of approximately 400 MHz yields, in some examples, an instantaneous pulsewidth of roughly 2.5 nanoseconds which enables a resolution to better than 30 centimeters.

Referring again to FIG. 1, the object to be located has an attached RF location tag 102, preferably a tag having a UWB transmitter, that transmits a signal comprising a burst (e.g., 72 pulses at a burst rate of 1 Mb/s), and optionally, a burst having a tag data packet that may include tag data elements that may include, but are not limited to, a tag unique identification number (tag UID), other identification information, a sequential burst count, stored tag data, or other desired information for object or personnel identification, inventory control, etc. In some embodiments, the tag data packet may include a tag-individual correlator that can be used to associate a specific individual (e.g., participant) with a specific tag. In some examples, the sequential burst count (e.g., a packet sequence number) from each tag 102 may be advantageously provided in order to permit, at a receiver hub 108, correlation of time of arrival (TOA) measurement data from various receivers 106.

In some examples, the RF location tag 102 may employ UWB waveforms (e.g., low data rate waveforms) to achieve extremely fine resolution because of their extremely short pulse (i.e., sub-nanosecond to nanosecond, such as a 2 ns (1 ns up and 1 ns down)) durations. As such, the tag data packet may be of a short length (e.g., 72-112 bits in some example embodiments), that advantageously enables a higher throughput and higher transmission rates. In some examples, higher throughput and/or higher transmission rates may result in larger datasets for filtering to achieve a more accurate location estimate. In some examples, rates of up to approximately 2600 updates per second can be accommodated without exceeding regulatory requirements. Alternatively or additionally, in some examples, the length of the tag data packets, in conjunction with other system functionality, may also result in a longer battery life (e.g., a 3.0 v 1 A-hr lithium cell battery may result in a tag battery life in excess of 3.8 years).

In some examples, one or more other tags, such as a reference tag 104, may be positioned within and/or about a monitored area or zone, such as monitored area 100 illustrated herein as a football field. In some examples, the reference tag 104 may be configured to transmit a signal that is used to measure the relative phase (e.g., the count of free-running counters) of non-resettable counters within the receivers 106.

One or more (preferably four or more) receivers 106 are also at locations with predetermined coordinates within and/or around the monitored area 100. In some examples, the receivers 106 may be connected in a "daisy chain" fashion to advantageously allow for a large number of receivers 106 to be interconnected over a significant monitored area in order to reduce and simplify cabling, reduce latency, provide power and/or the like. Each of the receivers 106 includes a receiver for receiving transmissions, such as UWB transmissions, and preferably, a packet decoding circuit that extracts a time of arrival (TOA) timing pulse train, transmitter ID, packet number and/or other information that may have been encoded in the tag transmission signal (e.g., material description, personal information, etc.) and is configured to sense signals transmitted by the tags 102 and one or more reference tags 104 (if present).

Each receiver 106 includes a time measuring circuit that measures time differences of arrival (TDOA) of tag bursts. The time measuring circuit is phase-locked (e.g., phase differences do not change and therefore respective frequencies are identical) with a common digital reference clock signal distributed via cable connection from a receiver hub 108 having a central timing reference clock generator. The reference clock signal establishes a common timing reference for the receivers 106. Thus, multiple time measuring circuits of the respective receivers 106 are synchronized in frequency, but not necessarily in phase. While there typically may be a phase offset between any given pair of receivers in the receivers 106, the offset is readily determined through use of a reference tag 104. Alternatively or additionally, each receiver may be synchronized wirelessly via virtual synchronization without a dedicated physical timing channel.

In some example embodiments, the receivers 106 are configured to determine various attributes of the received signal. Since measurements are determined at each receiver 106, in a digital format, rather than analog, signals are transmittable to the receiver hub 108. Advantageously, because packet data and measurement results can be transferred at high speeds to a receiver memory, the receivers 106 can receive and process tag (and corresponding object) locating signals on a nearly continuous basis. As such, in some examples, the receiver memory allows for a high burst rate of tag events (i.e., tag data packets) to be captured.

Data cables or wireless transmissions may convey measurement data from the receivers 106 to the receiver hub 108 (e.g., the data cables may enable a transfer speed of 2 Mbps). In some examples, measurement data is transferred to the receiver hub at regular polling intervals.

As such, the receiver hub 108 determines or computes tag location (i.e., object location) by processing TDOA measurements related to multiple data packets detected by the receivers 106. In some example embodiments, the receiver hub 108 may be configured to resolve the coordinates of a tag using nonlinear optimization techniques. The receiver hub 108 may also be referred to herein as a locate engine or a receiver hub/locate engine.

In some examples, the system described herein may be referred to as an "over-specified" or "over-determined" system. As such, the receiver hub 108 may then calculate one or more valid (i.e., most likely) locations based on a set of measurements and/or one or more incorrect (i.e., less likely) locations. For example, a location may be calculated that is impossible due the laws of physics (e.g., a tag on a football player that travels more than 100 yards in 1 second) or may be an outlier when compared to other locations. As such one or more algorithms or heuristics may be applied to minimize such error.

One such algorithm for error minimization, which may be referred to as a time error minimization algorithm, may be described as:

$$\varepsilon = \sum_{j=1}^{N} \sum_{k=j+1}^{N} \left\{ (t_j - t_k) - \frac{1}{c}\left[ [(x-x_j)^2 + (y-y_j)^2 + (z-z_j)^2]^{\frac{1}{2}} - [(x-x_k)^2 + (y-y_k)^2 + (z-z_k)^2]^{\frac{1}{2}} \right] \right\}^2$$

where N is the number of receivers, c is the speed of light, $x_{j,k}$, $y_{j,k}$ and $z_{j,k}$ are the coordinates of the receivers and $t_{j,k}$ are the arrival times received at each of the receivers. Note that only time differences may be evaluated at hub 108 in some example embodiments. The starting point for the minimization may be obtained by first doing an area search on a coarse grid of x, y and z over an area defined by the user and followed by a localized steepest descent search.

Another or second algorithm for error minimization, which may be referred to as a distance error minimization algorithm, may be defined by:

$$\varepsilon = \sum_{j=1}^{N} \left[ [(x-x_j)^2 + (y-y_j)^2 + (z-z_j)^2]^{\frac{1}{2}} - c(t_j - t_0) \right]^2$$

where time and location differences are replaced by their non-differential values by incorporating an additional unknown dummy variable, $t_0$, which represents an absolute time epoch. The starting point for this algorithm is fixed at the geometric mean position of all active receivers. No initial area search is needed, and optimization proceeds through the use of a DavidonFletcher-Powell (DFP) quasi-Newton algorithm in some examples. In other examples, a steepest descent algorithm may be used.

In order to determine the coordinates of a tag (T), in some examples and for calibration purposes, a reference tag (e.g., reference tag 104) is positioned at a known coordinate position ($x_T$, $y_T$, $z_T$).

In further example embodiments, a number N of receivers $\{R_j: j=1, \ldots, N\}$ (e.g., receivers 106) are positioned at known coordinates ($x_{R_j}$, $y_{R_j}$, $z_{R_j}$), which are respectively located at distances, such as:

$$d_{Rj} = \sqrt{(x_{Rj} - x_T)^2 + (y_{Rj} - y_T)^2 + (z_{Rj} - z_T)^2}$$

from a reference tag.

Each receiver $R_j$ utilizes, for example, a synchronous clock signal derived from a common frequency time base, such as clock generator. Because the receivers are not synchronously reset, an unknown, but constant offset $O_j$ exists for each receiver's internal free running counter. The value of the offset $O_j$ is measured in terms of the number of fine resolution count increments (e.g., a number of nanoseconds for a one nanosecond resolution system).

The reference tag is used to calibrate the radio frequency locating system as follows:

The reference tag emits a signal burst at an unknown time $\tau_R$. Upon receiving the signal burst from the reference tag, a count $N_{R_j}$ as measured at receiver $R_j$ is given by $$N_{R_j} = \beta\tau_R + O_j + \beta d_{Rj}/c$$

where c is the speed of light and $\beta$ is the number of fine resolution count increments per unit time (e.g., one per nanosecond). Similarly, each object tag $T_i$ of each object to be located transmits a signal at an unknown time $\tau_i$ to produce a count $$N_{ij} = \beta\tau_i + O_j + \beta d_{ij}/c$$

at receiver $R_j$ where $d_{ij}$ is the distance between the object tag $T_i$ and the receiver at receiver $R_j$. Note that $\tau_i$ is unknown, but has the same constant value for receivers of all receivers $R_j$. Based on the equalities expressed above for receivers $R_j$ and $R_k$ and given the reference tag information, differential offsets expressed as differential count values are determined as follows:

$$N_{R_j} - N_{R_k} = (O_j - O_k) + \beta\left(\frac{d_{R_j}}{c} - \frac{d_{R_k}}{c}\right)$$

or $$(O_j - O_k) = (N_{R_j} - N_{R_k}) - \beta\left(\frac{d_{R_j}}{c} - \frac{d_{R_k}}{c}\right) = \Delta_{jk}$$

$\Delta_{jk}$ is constant as long as $d_{Rj} - d_{Rk}$ remains constant, (which means the receivers and tag are fixed and there is no multipath situation) and $\beta$ is the same for each receiver. Note that $\Delta_{jk}$ is a known quantity, since $N_{R_j}$, $N_{R_k}$, $\beta$, $d_{R_j}/c$, and $d_{R_k}/c$ are known. That is, the differential offsets between receivers $R_j$ and $R_k$ may be readily determined based on the reference tag transmissions. Thus, again from the above equations, for an object tag ($T_i$) transmission arriving at receivers $R_j$ and $R_k$:

$$N_{ij} - N_{ik} = (O_j - O_k) + \beta(d_{ij}/c - d_{ik}/c) = \Delta_{jk} + \beta(d_{ij}/c - d_{ik}/c)$$

or, $$d_{ij} - d_{ik} = (c/\beta)[N_{ij} - N_{ik} - \Delta_{jk}].$$

The process further includes determining a minimum error value $E_i$, for each object tag $T_i$, according to the functional relationship:

$$E_i = \min_{(x,y,z)} \sum_j \sum_{k>j} [(d_{i_j} - d_{i_k}) - (dist(T_{x,y,z}, R_j) - dist(T_{x,y,z}, R_k))]^2$$

where $$dist(T_{x,y,z}, R_j) = \sqrt{(x_{R_j} - x)^2 + (y_{R_j} - y)^2 + (z_{R_j} - z)^2}$$

is the Euclidean distance between point (x,y,z) and the coordinates of the $j^{th}$ receiver $R_j$. The minimization solution (x',y',z') is the estimated coordinate location for the $i^{th}$ tag at $t_0$.

In an example algorithm, this proceeds according to:

$$\varepsilon = \sum_{j=1}^{N} \left[ [(x-x_j)^2 + (y-y_j)^2 + (z-z_j)^2]^{\frac{1}{2}} - c(t_j - t_0) \right]^2$$

where each arrival time, $t_j$, is referenced to a particular receiver (receiver "1") as follows:

$$t_j = \frac{1}{\beta}(N_j - N_1 - \Delta_{j_k})$$

and the minimization is performed over variables (x, y, z, $t_0$) to reach a solution (x', y', z', $t_0$').

In some example embodiments, the location of a tag 102 may then be output to a receiver processing and distribution system 110 for further processing of the location data to advantageously provide visualizations, predictive analytics, statistics and/or the like.

The exemplary radio frequency locating system of FIG. 1 may be used in providing performance analytics in accordance with some embodiments of the present invention. In the environment of FIG. 1, data may be captured and analyzed, such as during a sporting event to identify events, statistics, and other data useful to a sports team, league, viewer, licensee, or the like. In some embodiments, data associated with a number of objects or participants (e.g., players, officials, balls, game equipment, etc.) on a playing field, such as monitored area 100, may be generated and provided to a performance analytics system. As such, as further discussed in connection with FIGS. 2A-C below, each object may have one or more attached tags 102 (such as to equipment worn by a player) to be used to track data such as location, change of location, speed, or the like of each object. In some embodiments, additional sensors, such as, without limitation, accelerometers, magnetometers, time-of-flight sensors, health sensors, temperature sensors, moisture sensors, light sensors, or the like, may be attached to each object to provide further data to the performance analytics system. Such additional sensors may provide data to the tag 102, either through a wired or wireless connection, to be transmitted to the receivers 106 or the sensors may be configured to transmit data to receivers (i.e., sensor receivers) separately from tags 102.

One or more of the receivers 106 may receive transmissions from tags 102 and transmit the blink data to a receiver hub 108. The receiver hub 108 may process the received data to determine tag location for the tags 102. The receiver hub 108 may transmit the tag location data to one or more processors, such as receiver processing and distribution system 110. Receiver processing and distribution system 110 may use one or more modules (e.g., processing engines) and one or more databases to identify the object each of the tags 102 is associated with, such as a player, official, ball, or the like.

In some embodiments, multiple tags 102 (as well as other sensors) may be attached to the equipment worn by an individual player, official, or other participant. The receiver processing and distribution system 110 may use one or more databases to associate the tag identifier (e.g., a tag UID) of each tag 102 with each player, official, object, or other participant and correlate the tag location data and/or other tag and sensor derived data for multiple tags 102 that are associated with a particular player, official, object, or other participant.

As discussed in greater detail below, the receiver processing and distribution system 110 may then use the tag location data and/or other tag and sensor derived data to determine player dynamics, such as a player's location, how the location is changing with time, orientation, velocity, acceleration, deceleration, total yardage, or the like. The receiver processing and distribution system 110 may also use the tag location data and/or other tag and sensor derived data to determine dynamics for other participants such as the officials, the ball, penalty markers, line of scrimmage or yards to gain markers, or the like, for use in generating data for performance analytics. The receiver processing and distribution system 110 may also use the data and one or more databases to determine team formations, play activity, events, statistics, or the like, such as by comparing the data to various models to determine the most likely formation or play or the events that have occurred during a game. The receiver processing and distribution system 110 may also use the data to provide statistics or other output data for the players, teams, and the game.

As will be apparent to one of ordinary skill in the art, the inventive concepts herein described are not limited to use with the UWB based RF locating system shown in FIG. 1. Rather, in various embodiments, the inventive concepts herein described may be applied to various other locating systems especially those that are configured to provide robust location resolution (i.e., subfoot location resolution).

Example Tag/Sensor Positioning and Participant Correlation

FIG. 1 shows a monitored area 100. The monitored area 100 comprises a plurality of positions at one or more time epochs. The plurality of positions may be divided into one or more regions, called zones. Each zone may be described by one or more coordinate systems, such as a local NED (North-East-Down) system, a latitude-longitude system, or even a yard line system as might be used for an American football game. A location is a description of a position, or a plurality of positions, within the monitored area. For example, a field marker at the intersection of the south goal line and west out of bounds line at Bank of America Stadium in Charlotte, N.C. could be described as {0,0,0} in a local NED system, or 35.225336 N 80.85273 W longitude 751 ft. altitude on a latitude-longitude system, or simply "Panthers Goal Line" in a yard line system. Because different types of locating systems or different zones within a single locating system may use different coordinate systems, a Geographical Information System or similar monitored area database may be used to associate location data. One type of Geographical Information System describing at least a field of play may be called Field Data.

Figure 2A:
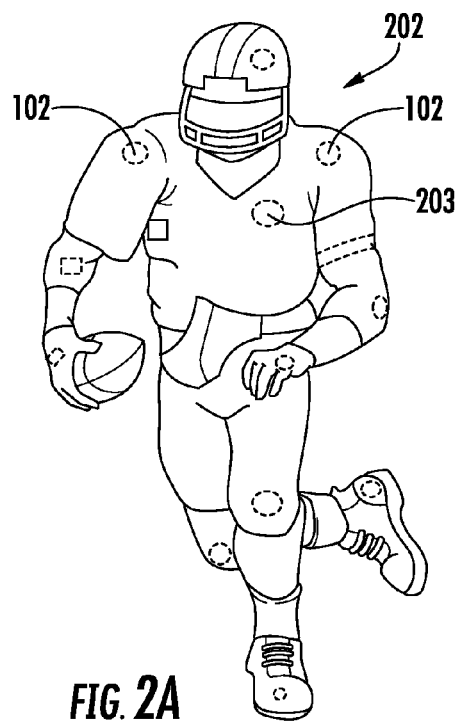
Figure 2B:
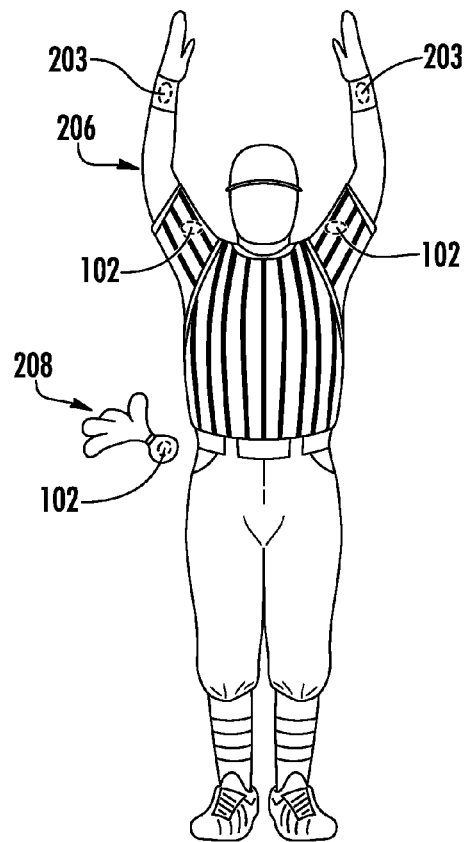
Figure 2C:
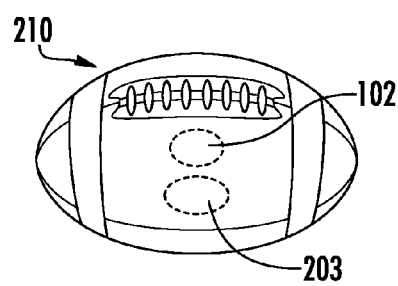

FIGS. 2A-C illustrate some exemplary participants that may provide information to a performance analytics system in accordance with some embodiments of the present invention. FIG. 2A illustrates a player 202 (e.g., a football player)

wearing equipment having attached tags 102 in accordance with some embodiments. In particular, the depicted player 202 is wearing shoulder pads having tags 102 affixed to opposite sides thereof. This positioning advantageously provides an elevated broadcast position for each tag 102 thereby increasing its communication effectiveness.

Additional sensors 203 may be attached to equipment worn by player 202, such as accelerometers, magnetometers, time-of-flight sensors, health monitoring sensors (e.g., blood pressure sensors, heart monitors, respiration sensors, moisture sensors, temperature sensors), light sensors, or the like. The additional sensors 203 may be affixed to shoulder pads, the helmet, the shoes, rib pads, elbow pads, the jersey, the pants, a bodysuit undergarment, gloves, arm bands, wristbands, and the like.

Sensors 203 may be configured to communicate with receivers (e.g., receivers 106 of FIG. 1) directly or indirectly through tags 102 or other transmitters. For example, in one embodiment, a sensor 203 may be connected, wired (e.g., perhaps through wires sewn into a jersey or bodysuit undergarment) or wirelessly, to tags 102 to provide sensor data to tags 102, which is then transmitted to the receivers 106. In another embodiment, a plurality of sensors (not shown) may be connected to a dedicated antenna or transmitter, perhaps positioned in the helmet, which may transmit sensor data to one or more receivers.

FIG. 2B illustrates a game official 206 wearing equipment having attached tags 102 and sensors 203 in accordance with some embodiments. In the depicted embodiment, tags 102 are attached to the official's jersey proximate opposite shoulders. Sensors 203 are positioned in wristbands worn on the official's wrists as shown. Sensors 203 may be configured to communicate with receivers (e.g., receivers 106 of FIG. 1) directly or indirectly through tags 102 or other transmitters as discussed above in connection with FIG. 2A.

As discussed in greater detail below, the positioning of sensors 203 (here, accelerometers) proximate the wrists of the official may allow the receiver processing and distribution system 110 to determine particular motions, movements, or activities of the official 206 for use in determining events (e.g., winding of the game clock, first down, touchdown, or the like). The official 206 may also carry other equipment, such as penalty flag 208, which may also have a tag 102 (and optionally one or more sensors) attached to provide additional data to the receiver processing and distribution system 110. For example, the receiver processing and distribution system 110 may use tag location data from the penalty flag 208 to determine when the official is merely carrying the penalty flag 208 versus when the official is using the penalty flag 208 to indicate an event, such as a penalty (e.g., by throwing the penalty flag 208).

FIG. 2C illustrates an example of a ball 210 having tags 102 attached or embedded in accordance with some embodiments. Additionally, sensors 203 may be attached to or embedded in the ball 210, such as accelerometers, time-of-flight sensors, or the like. In some embodiments, the sensor 203 may be connected, wired or wirelessly, to tag 102 to provide sensor data to tag 102 which is then transmitted to the receivers 106. In some embodiments, the sensor 203 may transmit sensor data to receivers separately from the tag 102, such as described above in connection with FIG. 2A.

As will be apparent to one of ordinary skill in the art in view of this disclosure, once the tags 102 and sensors 203 of FIGS. 2A-C are positioned on participants, they may be correlated to such participants. For example, in some embodiments, unique tag or sensor identifiers ("unique IDs") may be correlated to a participant profile (e.g., John Smith—running back, Fred Johnson—line judge official, or ID 027—one of several game balls, etc.) and stored to a remote database accessible to the performance analytics system as discussed in greater detail below. Each participant profile may further include or be correlated with a variety of data including, but not limited to, biometric data (e.g., height, weight, health data, etc.), role data, team ID, performance statistics, and other data that may be apparent to one of skill in the art in view of the foregoing description.

In some embodiments, such participant profile or role data may be pre-defined and stored in association with the unique tag or sensor identifiers. In other embodiments, the participant profile or role data may also be "learned" by the system as a result of received tag or sensor data, formation data, play data, event data, and/or the like. For example, in some embodiments the system may determine that a tag or sensor is not correlated to a participant profile and may analyze data received from the tag and/or sensor to determine possible participant roles, etc., which may be ranked and then selected/confirmed by the system or by a user after being displayed by the system. In some embodiments, the system may determine possible participant roles (i.e., participant role data) based on determined participant location data (e.g., movement patterns, alignment position, etc.).

In some embodiments, as described in greater detail below, the participant profile or role data may also be updated by the system (i.e., to produce a data set for the participant that is far more robust than that established at initial registration) as a result of received tag or sensor data, formation data, play data, event data, and/or the like. In some embodiments, the participant profile and/or role data may be used in a performance analytics system to weight the actions of the participants during analysis to assist in qualifying what is occurring, such as in determining formations, plays, events, etc.

Tag ID and Sensor Data Transmission Architecture

FIGS. 3A, 3B, 3C, 3D, and 3E show block diagrams of various different architectures that may be utilized in transmitting signals from one or more tags and sensors to one or more receivers of a receiver processing and analytics system in accordance with embodiments of the invention. In some embodiments, the depicted architectures may be used in connection with the receiver processing and analytics system 110 of FIG. 1. More than one of these architectures may be used together in a single system.

FIG. 3A shows a RF location tag 102, such as that shown in FIG. 1, which may be configured to transmit a tag signal to one or more receivers 106. The one or more receivers 106 may transmit a receiver signal to the receiver hub/locate engine 108.

The depicted RF location tag 102 may generate or store a tag unique identifier ("tag UID") and/or tag data as shown. The tag data may include useful information such as the installed firmware version, last tag maintenance date, configuration information, and/or a tag-individual correlator. The tag-individual correlator may comprise data that indicates that a monitored individual (e.g., participant) is associated with the RF location tag 102 (e.g. name, uniform number and team, biometric data, tag position on individual, i.e., right wrist). As will be apparent to one of skill in the art in view of this disclosure, the tag-individual correlator may be stored to the RF location tag 102 when the tag is registered or otherwise associated with an individual. While shown as a separate field for illustration purposes, one of ordinary skill in the art may readily appreciate that the tag-individual correlator may be part of any tag data or even omitted from the tag.

The tag signal transmitted from RF location tag 102 to receiver 106 may include "blink data" as it is transmitted at selected intervals. This "blink rate" may be set by the tag designer or the system designer to meet application requirements. In some embodiments it is consistent for one or all tags; in some embodiments it may be data dependent. Blink data includes characteristics of the tag signal that allow the tag signal to be recognized by the receiver 106 so the location of the RF location tag 102 may be determined by the locating system. Blink data may also comprise one or more tag data packets. Such tag data packets may include any data from the tag 102 that is intended for transmission such as, for example in the depicted embodiment, a tag UID, tag data, and a tag-individual correlator. In the case of TDOA systems, the blink data may be or include a specific pattern, code, or trigger that the receiver 106 (or downstream receiver processing and analytics system) detects to identify that the transmission is from a RF location tag 102 (e.g., a UWB tag).

The depicted receiver 106 receives the tag signal, which includes blink data and tag data packets as discussed above. In one embodiment, the receiver 106 may pass the received tag signal directly to the receive hub/locate engine 108 as part of its receiver signal. In another embodiment, the receiver 106 could perform some basic processing on the received tag signal. For instance, the receiver could extract blink data from the tag signal and transmit the blink data to the receive hub/locate engine 108. The receiver could transmit a time measurement to the receive hub/locate engine 108 such as a TOA measurement and/or a TDOA measurement. The time measurement could be based on a clock time generated or calculated in the receiver, it could be based on a receiver offset value as explained above, it could be based on a system time, and/or it could be based on the time difference of arrival between the tag signal of the RF location tag 102 and the tag signal of a RF reference tag (e.g., tag 104 of FIG. 1). The receiver 106 could additionally or alternatively determine a signal measurement from the tag signal (such as a received signal strength indication (RSSI), a direction of signal, signal polarity, or signal phase) and transmit the signal measurement to the receive hub/locate engine 108.

FIG. 3B shows a RF location tag 202 and sensor 203, such as those worn on an individual's person as shown in FIG. 2, which may be configured to transmit tag signals and sensor signals, respectively, to one or more receivers 106, 166. The one or more receivers 106, 166 may then transmit receiver signals to the receiver hub/locate engine 108. One or more receivers 106, 166 may share physical components, such as a housing or antenna.

The depicted RF location tag 202 may comprise a tag UID and tag data (such as a tag-individual correlator) and transmit a tag signal comprising blink data as discussed in connection with FIG. 3A above. The depicted sensor 203 may generate and/or store a sensor UID, additional stored sensor data (e.g. a sensor-individual correlator, sensor type, sensor firmware version, last maintenance date, the units in which environmental measurements are transmitted, etc.), and environmental measurements. The "additional stored sensor data" of the sensor 203 may include any data that is intended for transmission, including but not limited to a RF location tag 202, a reference tag (e.g., 104 of FIG. 1), a sensor receiver, a receiver 106, and/or the receiver/hub locate engine 108.

The sensor-individual correlator may comprise data that indicates that a monitored individual is associated with the sensor 203 (e.g., name, uniform number and team, biometric data, sensor position on individual, i.e., right wrist). As will be apparent to one of skill in the art in view of this disclosure, the sensor-individual correlator may be stored to the sensor 203 when the sensor is registered or otherwise associated with an individual. While shown as a separate field for illustration purposes, one of ordinary skill in the art may readily appreciate that the sensor-individual correlator may be part of any additional stored sensor data or omitted from the sensor altogether.

Sensors such as sensor 203 that are structured according to embodiments of the invention may sense or determine one or more environmental conditions (e.g. temperature, pressure, pulse, heartbeat, rotation, velocity, acceleration, radiation, position, chemical concentration, voltage) and store or transmit "environmental measurements" that are indicative of such conditions. To clarify, the term "environmental measurements" includes measurements concerning the environment proximate the sensor including, without limitation, ambient information (e.g., temperature, position, humidity, etc.) and information concerning an individual's health, fitness, operation, and/or performance. Environmental measurements may be stored or transmitted in either analog or digital form and may be transmitted as individual measurements, as a set of individual measurements, and/or as summary statistics. For example, temperature in degrees Celsius may be transmitted as {31}, or as {33, 32, 27, 22, 20, 23, 27, 30, 34, 31}, or as {27.9}. In some embodiments, the sensor-individual correlator could be determined at least in part from the environmental measurements.

In the depicted embodiment, RF location tag 202 transmits a tag signal to receiver 106 and sensor 203 transmits a sensor signal to sensor receiver 166. The sensor signal may comprise one or more sensor information packets. Such sensor information packets may include any data or information from the sensor 203 that is intended for transmission such as, for example in the depicted embodiment, sensor UID, additional stored sensor data, sensor-individual correlator, and environmental measurements. A receiver signal from receiver 106 and a sensor receiver signal from sensor receiver 166 may be transmitted via wired or wireless communication to receiver hub/locate engine 108 as shown.

FIG. 3C depicts a sensor 203 communicating through a RF location tag 202 in accordance with various embodiments. In one embodiment, the sensor 203 may be part of (i.e., reside in the same housing or assembly structure) of the RF location tag 202. In another embodiment, the sensor 203 may be distinct from (i.e., not resident in the same housing or assembly structure) the RF location tag 202 but configured to communicate wirelessly or via wired communication with the RF location tag 202.

In one embodiment, the RF location tag 202, the sensor 203, or both, may generate and/or store a tag-sensor correlator that indicates an association between a RF location tag 202 and a sensor 203 (e.g., tag UID/sensor UID, distance from tag to sensor in a particular stance, set of sensors associated with a set of tags, sensor types associated with a tag, etc.). In the depicted embodiment, both the RF location tag 202 and the sensor 203 store the tag-sensor correlator.

In the depicted embodiment, sensor 203 transmits a sensor signal to RF location tag 202. The sensor signal may comprise one or more sensor information packets as discussed above. The sensor information packets may comprise the sensor UID, a sensor-individual correlator, additional stored sensor data, the tag-sensor correlator, and/or the environmental measurements. The RF location tag 202 may store some portion of, or all of, the sensor information packets locally and may package the sensor information packets into one or more tag data packets for transmission to receiver 106 as part of a tag signal or simply pass them along as part of its tag signal.

FIG. 3D illustrates an example communication structure for a reference tag 104 (e.g., reference tag 104 of FIG. 1), an RF location tag 202, a sensor 203, and two receivers 106 in accordance with one embodiment. The depicted reference tag 104 is a RF location tag and thus may include tag data, a tag UID, and is capable of transmitting tag data packets. In some embodiments, the reference tag 104 may form part of a sensor and may thus be capable of transmitting sensor information packets.

The depicted sensor 203 transmits a sensor signal to RF reference tag 104. The RF reference tag 104 may store some portion or some or all of the sensor information packets locally and may package the sensor information packets into one or more tag data packets for transmission to receiver 106 as part of a tag signal, or simply pass them along as part of its tag signal.

As was described above in connection with FIG. 1, the receivers 106 of FIG. 3D are configured to receive tag signals from the RF location tag 202 and the reference tag 104. Each of these tag signals may include blink data, which may comprise tag UIDs, tag data packets, and/or sensor information packets. The receivers 106 each transmit receiver signals via wired or wireless communication to the receiver hub/locate engine 108 as shown.

FIG. 3E illustrates an example communication structure between an RF location tag 202, a plurality of receivers 106, and a variety of sensor types including, without limitation, a sensor 203, a diagnostic device 233, a triangulation positioner 243, a proximity positioner 253, and a proximity label 263 in accordance with various embodiments. In the depicted embodiment, none of the sensors 203, 233, 243, 253 form part of an RF location tag 202 or reference tag 104. However, each may comprise a sensor UID and additional stored sensor data. Each of the depicted sensors 203, 233, 243, 253 transmits sensor signals comprising sensor information packets.

In the depicted embodiment, receiver 106 is configured to receive a tag signal from RF location tag 202 and a sensor signal directly from sensor 203. In such embodiments, sensor 203 may be configured to communicate in a communication protocol that is common to RF location tag 202 as will be apparent to one of ordinary skill in the art in view of this disclosure.

FIG. 3E depicts one type of sensor referred to herein as a "proximity interrogator". The proximity interrogator 223 can include circuitry operative to generate a magnetic, electromagnetic, or other field that is detectable by a RF location tag 202. While not shown in FIG. 3E, a proximity interrogator 223 may include a sensor UID and other tag and sensor derived data or information as discussed above.

In some embodiments, the proximity interrogator 223 is operative as a proximity communication device that can trigger a RF location tag 202 (e.g., when the RF location tag 202 detects the field produced by the proximity interrogator 223) to transmit blink data under an alternate blink pattern or blink rate. The RF location tag can initiate a preprogrammed (and typically faster) blink rate to allow more location points for tracking an individual. In some embodiments, the RF location tag may not transmit a tag signal until triggered by the proximity interrogator 223. In some embodiments the RF location tag 202 may be triggered when the RF location tag 202 moves near (e.g., within communication proximity to) a proximity interrogator 223. In some embodiments, the RF location tag may be triggered when the proximity interrogator 223 moves near to the RF location tag 202.

In other embodiments, the RF location tag 202 may be triggered when a button is pressed or a switch is activated on the proximity interrogator 223 or on the RF location tag itself.

For example, a proximity interrogator 223 could be placed at the start line of a racetrack. Every time a car passes the start line, a car-mounted RF location tag 202 senses the signal from the proximity interrogator and is triggered to transmit a tag signal indicating that a lap has been completed. As another example, a proximity interrogator 223 could be placed at a Gatorade cooler. Each time a player or other participant fills a cup from the cooler a participant-mounted RF location tag 202 senses the signal from the proximity interrogator and is triggered to transmit a tag signal indicating that Gatorade has been consumed. As another example, a proximity interrogator 223 could be placed on a medical cart. When paramedics use the medical cart to pick up a participant (e.g., a player) and move him/her to the locker room, a participant-mounted RF location tag 202 senses the signal from the proximity interrogator and is triggered to transmit a tag signal indicating that they have been removed from the game. As explained, any of these post-triggered tag signals may differ from pre-triggered tag signals in terms of any aspect of the analog and/or digital attributes of the transmitted tag signal.

FIG. 3E depicts another type of sensor that is generally not worn by an individual but is referred to herein as a "diagnostic device". However, like other sensors, diagnostic devices may measure one or more environmental conditions and store corresponding environmental measurements in analog or digital form.

While the depicted diagnostic device 233 is not worn by an individual, it may generate and store a sensor-individual correlator for association with environmental measurements taken in connection with a specific individual. For example, in one embodiment, the diagnostic device 233 may be a blood pressure meter that is configured to store as environmental measurements blood pressure data for various individuals. Each set of environmental measurements (e.g., blood pressure data) may be stored and associated with a sensor-individual correlator.

The depicted diagnostic device 233 is configured to transmit a sensor signal comprising sensor information packets to a sensor receiver 166. The sensor information packets may comprise one or more of the sensor UID, the additional stored data, the environmental measurements, and/or the sensor-individual correlator as discussed above. The sensor receiver 166 may associate some or all of the data from the sensor information packets with other stored data in the sensor receiver 166 or with data stored or received from other sensors, diagnostic devices, RF location tags 102, or reference tags. The sensor receiver 166 transmits a sensor receiver signal to a receiver hub/locate engine 108.

Another type of sensor shown in FIG. 3E is a triangulation positioner 243. A "triangulation positioner" is a type of sensor that senses position. The depicted triangulation positioner 243 includes a sensor UID, additional stored sensor data, and environmental measurements as discussed above.

In some embodiments, a triangulation positioner (also known as a global positioning system (GPS) receiver) receives clock data transmitted by one or more geostationary satellites (a satellite in a known or knowable position) and/or one or more ground based transmitters (also in known or knowable positions), compares the received clock data, and computes a "position calculation". The position calculation may be included in one or more sensor information packets as environmental measurements.

In another embodiment, a triangulation positioner comprises one or more cameras or image-analyzers that receive emitted or reflected light or heat, and then analyzes the received images to determine the location of an individual or sensor. Although a triangulation positioner may transmit data wirelessly, it is not a RF location tag because it does not transmit blink data or a tag signal that can be used by a receiver hub/locate engine 108 to calculate location. In contrast, a triangulation positioner senses position and computes a position calculation that may then be used as environmental measurements by the receiver hub/locate engine 108.

In one embodiment, a triangulation positioner could be combined with a RF location tag or reference tag (not shown). In such embodiments, the triangulation positioner could compute and transmit its position calculation via the RF location tag to one or more receivers. However, the receiver hub/locate engine would calculate tag location based on the blink data received as part of the tag signal and not based solely on the position calculation. The position calculation would be considered as environmental measurements and may be included in associated sensor information packets.

As will be apparent to one of ordinary skill in the art, position calculations (e.g., GPS receiver position calculations) are not as accurate as the location calculations (e.g., UWB waveform based location calculations) performed by receiver hub/locate engines structured in accordance with various embodiments of the invention. That is not to say that position calculations may not be improved using known techniques. For example, a number of influences, including atmospheric conditions, can cause GPS accuracy to vary over time. One way to control this is to use a differential global positioning system (DGPS) comprising one or a network of stationary triangulation positioners that are placed in a known position, and the coordinates of the known position are stored in memory as additional stored sensor data. These triangulation positioners receive clock data from geostationary satellites, determine a position calculation, and broadcast a difference between the position calculation and the stored coordinates. This DGPS correction signal can be used to correct for these influences and significantly reduce location estimate error.

Another type of sensor shown in FIG. 3E is a proximity detector 253. A "proximity detector" is a type of sensor that senses identity within an area (e.g., a local area) that is small with respect to the monitored area 100 of FIG. 1. Many different ways of sensing identity (e.g., a unique ID or other identifier for a sensed object or individual) would be apparent to one of ordinary skill in the art in view of this disclosure including, without limitation, reading a linear bar code, reading a two-dimensional bar code, reading a near field communication (NFC) tag, reading a RFD tag such as a UHF tag, HF tag, or low frequency tag, an optical character recognition device, a biometric scanner, or a facial recognition system.

In some embodiments, a proximity detector senses an attribute of an individual (or an individual's wristband, tag, label, card, badge, clothing, uniform, costume, phone, ticket, etc.). The identity sensed by a proximity detector may be stored locally at the proximity detector 253 as shown and transmitted as environmental measurements via one or more sensor information packets to a sensor receiver 166.

In some embodiments, a proximity detector 253 may have a defined position, which is often stationary, and may be associated with a location in the monitored area 100 of FIG. 1. For example, a proximity detector 253 could be located at a finish line of a race track, an entrance gate of a stadium, with a diagnostic device, at a goal line or goal post of a football field, at a base or home plate of a baseball diamond, or a similar fixed location. In such embodiments where the proximity detector is stationary, the position coordinates of the proximity detector and a sensor UID could be stored to a monitored area database (not shown) that is accessible by one or more of the receivers 106, 166, the receiver hub/locate engine 108, and/or other components of the receiver processing and analytics system 110. In embodiments where the proximity detector is movable, a position calculation could be determined with a triangulation positioner, or the proximity detector could be combined with a RF location tag and located by the receiver hub/locate engine 108. While shown as separate fields for illustration purposes in FIG. 3E, identify information and position calculation could comprise part of the additional stored sensor data, the environmental measurements, or both.

In one embodiment, the proximity detector could be associated with a reference tag (e.g., tag 104 of FIG. 1) whose position is recorded in the monitored area database. In other embodiments, the proximity detector is movable, such that it may be transported to where it is needed. For example, a proximity detector 253 could be located on a medical cart, first down marker, a diagnostic device, goal post, or carried by a paramedic or security guard. In an embodiment where the proximity detector 253 is movable it would typically be associated with a RF location tag or triangulation positioner so that location (for a RF location tag) or position (for a triangulation positioner) can be determined at the time identity is sensed.

In the embodiment where the proximity detector includes a RF location tag, the receiver hub/locate engine 108 would locate the associated RF location tag, and the tag data/sensor data filter 112 would associate the tag location data for the associated RF location tag as the position of the proximity detector, while determining the identity of an associated individual from any received sensor information packets. In the alternate embodiment where the proximity detector includes a triangulation positioner, the triangulation positioner would compute a position calculation that could be stored as additional stored sensor data and/or environmental measurements, and transmitted as one or more sensor information packets. In one embodiment, sensor information packets for a proximity detector may include both sensed identity information and a position calculation.

Another type of sensor shown in FIG. 3E is a proximity label 263. A proximity label has a fixed position and an identification code (e.g., a sensor UID). The proximity label 263 may further comprise additional stored sensor data as shown. The depicted proximity label 263 is configured to be read by proximity detector 253. In some embodiments, proximity detector 253 may be further configured to write information to proximity label 263.

A proximity label 263 may be a sticker, card, tag, passive RFID tag, active RFID tag, NFC tag, ticket, metal plate, electronic display, electronic paper, inked surface, sundial, or otherwise visible or machine readable identification device as is known in the art. The coordinates of the position of the proximity label 263 are stored such that they are accessible to the receive hub/locate engine 108. For example, in one embodiment, the position coordinates of a proximity label 263 could be stored in a field database or monitored area database accessible via a network, or stored locally as additional stored data in the proximity detector 253.

In some embodiments, a position of the proximity label 263 is encoded into the proximity label 263 itself. For example, coordinates of a position of the proximity label 263 could be encoded into a passive RFID tag that is placed in that position. As another example, the coordinates of a position of the proximity label 263 could be encoded into a printed barcode that is placed in that position. As another example, a proximity label 263 comprising a NFC tag could be encoded with the location "end zone", and the NFC tag could be placed at or near an end zone at Bank of America stadium. In some embodiments, the stored coordinates of the proximity label 263 may be offset from the actual coordinates of the proximity label 263 by a known or determinable amount.

In one embodiment, a proximity label 263 such as an NFC tag may be encoded with a position. When a sensor such as a proximity detector approaches the NFC tag it may read the position, then transmit the position in a sensor information packet to the sensor receiver 166' and eventually to the receiver hub/locate engine 108. In another embodiment, a proximity label 263 such as a barcode label may be encoded with an identification code. When a smartphone with a proximity detector (such as a barcode imager) and a triangulation positioner (such as a GPS chip, GPS application, or similar device) approaches the barcode label it may read the identification code from the barcode, determine a position calculation from received clock data, then transmit the identity and the position calculation to sensor receiver 166' and eventually to the receiver hub/locate engine 106 as part of one or more sensor information packets.

In the depicted embodiment, triangulation positioner 243 and proximity detector 253 are each configured to transmit sensor signals carrying sensor information packets to sensor receiver 166'. The depicted sensors 243, 253, like any sensor discussed herein, may transmit sensor signals via wired or wireless communication protocols. For example, any proprietary or standard wireless protocol (e.g., 802.11, Zigbee, ISO/IEC 802.15.4, ISO/IEC 18000, IrDA, Bluetooth, CDMA, or any other protocol) could be used for the sensor signals. Alternatively or additionally, any standard or proprietary wired communication protocol (e.g., Ethernet, Parallel, Serial, RS-232, RS-422, USB, Firewire, I$^2$C, etc.) may be used. Similarly, sensor receiver 166', and any receiver discussed herein, may use similar wired and wireless protocols to transmit receiver signals to the receiver hub/locate engine.

In one embodiment, upon receiving sensor signals from the triangulation positioner 243 and the proximity detector 253, the sensor receiver 166' may associate some or all of the data from the received sensor information packets with other data stored to the sensor receiver 166', or with data stored or received from other sensors (e.g., sensor 203), diagnostic devices 233, RF location tags 102, or RF reference tags 104. Such associated data is referred to herein as "associated sensor data". In the depicted embodiment, the sensor receiver 166' is configured to transmit some or all of the received sensor information packets and any associated sensor data to the receiver hub/locate engine 108 at part of a sensor receiver signal.

In one embodiment, a smartphone comprising a proximity detector (such as a barcode imager) and a triangulation positioner (such as a GPS chip) may associate an identification code determined from a barcode with a position calculation from received clock data as associated sensor data and transmit a sensor information packet that includes such associated sensor data to the receiver hub/locate engine 108. In another embodiment, the smartphone could transmit a first sensor information packet including the identification code and the smartphone's unique identifier to another sensor receiver, the smartphone could transmit a second sensor information packet including the position calculation and the smartphone's unique identifier to the sensor receiver, and the sensor receiver could associate the position calculation with the identification code based on the common smartphone unique identifier and transmit such associated sensor data to the receiver hub/locate engine 108. In another embodiment, the sensor receiver could determine a first time measurement associated with the first sensor information packet and a second time measurement associated with the second sensor information packet that, in conjunction with the sensor UID, could be used, by the receiver hub/locate engine 108, to associate the first sensor information packet with the second sensor information packet.

In one embodiment, the receiver hub/locate engine 108 receives receiver signals from the receiver 106 and sensor receiver signals from the sensor receivers 166, 166'. In the depicted embodiment, receiver 106 may receive blink data from the RF location tag 102 and transmits to the receiver hub/locate engine 108 some or all of the blink data, perhaps with additional time measurements or signal measurements. In some embodiments, time measurements or signal measurements may be based on a tag signal received from a RF reference tag (e.g., reference tag 104 of FIG. 1). The receiver hub/locate engine 108 collects the blink data, time measurements (e.g. time of arrival, time difference of arrival, phase), and/or signal measurements (e.g. signal strength, signal direction, signal polarization, signal phase) from the receivers 106 and computes tag location data for the tags 102 as discussed above in connection with FIG. 1. In some embodiments, the receivers 106 may be configured with appropriate RF filters, such as to filter out potentially interfering signals or reflections proximate the field of play or other area to be monitored.

The receiver hub/locate engine 108 may also access stored data or clock data from local storage and from a network location. The receiver hub/locate engine 108 uses this information to determine tag location data for each RF location tag. It may also associate data derived or extracted from tag signals transmitted from one or more RF location tags with information or data derived or extracted from sensor signals transmitted from one or more sensors.

In addition to the TOA or TDOA systems previously described, other real-time location systems (RTLS) such as received signal strength indication based systems could potentially be implemented by a receiver hub/locate engine 108. Any RTLS system using RF location tags, including those described herein, could require considerable processing by the receiver hub/locate engine 108 to determine the tag location data from the blink data received from the tags. These may require time measurement and/or signal measurement in addition to blink data, which preferably includes a tag UID. In contrast, in other systems, such as global position systems (GPS) systems, location data is determined based upon the position calculation transmitted from a GPS transmitter (also referred to as a GPS receiver or GPS tag) which includes calculated information about the location where the tag was positioned (i.e., coordinates determined at the tag via satellite signal triangulation, etc.) when the position calculation was determined or stored. Thus, GPS information typically refers to additional information that is transmitted along with a GPS transmitter ID before the transmission is received by a sensor receiver.

A GPS host device or back-end server may receive the GPS information and simply parse the position calculation (as opposed to calculating the position information at the host device) and the GPS transmitter ID into a data record. This data record may be used as a GPS position calculation, or it could be converted to a different coordinate system to be used as a GPS position calculation, or it could be processed further with DGPS information to be used as a GPS position calculation.

Returning to FIG. 3C, the depicted RF location tag 202 is used to convey (sometimes called backhaul) sensor information packets to a receiver 106. In some embodiments, while not shown, multiple sensors 203 may transmit sensor signals carrying sensor information packets to RF location tag 202.

Such received sensor information packets may be associated with blink data that is transmitted to receiver 106.

In one embodiment, the receiver hub/locate engine 108 may parse sensor information packets from received tag data packets and associate such sensor information packets with the RF location tag 202 that transmitted the sensor information packet. Thus, the receiver hub/locate engine 108 may be able to determine tag location data, which may comprise a location and other data (e.g., tag data, tag UID, tag-individual correlator, sensor-individual correlator, additional stored sensor data, environmental measurements, tag-sensor correlator, identity information, position calculation, etc.) from one or more tags or sensors. Such data and information may be transmitted to the receiver processing and analytics system 110.

In some embodiments, once the receiver hub/locate engine 108 determines a location estimate of a RF location tag 102 at the time epoch of the tag signal, the receiver hub/locate engine 108 can also associate a location estimate with the tag data packet included in the blink data of such tag signal. In some embodiments, the location estimate of the tag signal may be used as tag location data for the tag data packet. In some embodiments a Geographical Information System (GIS) may be used by the receive hub/locate engine 108 to refine a location estimate, or to map a location estimate in one coordinate system to a location estimate in a different coordinate system, to provide a location estimate for the tag data packet.

In one embodiment, the location estimated for the tag data packet may be associated with any data in the tag data packet, including a tag UID, other tag data, and, if included, one or more sensor information packets, including sensor UID, additional stored sensor data, and environmental measurements. Since environmental measurements may include a position calculation from a triangulation positioner (e.g., a GPS device), the receiver hub/locate engine 108 could parse the position calculation and use it to refine a location estimate for the tag data packet.

Preferably, the receiver hub/locate engine 108 may access an individual database to determine tag-individual correlators or sensor-individual correlators. Individual data (e.g., an individual profile) may be stored in a server, in tag memory, in sensor memory, or in other storage accessible via a network or communication system, including tag data or additional stored sensor data as explained previously.

In some embodiments, by comparing data accessed using a sensor-individual correlator, the receiver hub/locate engine 108 may associate an individual with a sensor information packet received from a sensor, and/or may associate an individual with such sensor. Because the receiver hub/locate engine 108 may associate a sensor position estimate with a sensor information packet, the receiver hub/locate engine 108 may also estimate an individual position for the associated individual.

In another embodiment, by comparing data accessed using a tag-sensor correlator, the receiver hub/locate engine 108 may associate a sensor with a tag data packet received from a RF location tag 102. Because the receiver hub/locate engine 108 may associate a location estimate with a tag data packet, the receiver hub/locate engine 108 may also create a sensor location estimate for the associated sensor. By comparing a location estimate for a RF location tag with a sensor location estimate or a sensor position estimate, the receiver hub/locate engine 108 may associate a RF location tag with a sensor, or may associate a tag data packet with a sensor information packet. The receiver hub/locate engine 108 could also determine a new or refined tag-sensor correlator based on this association.

In still another embodiment, by comparing a location estimate for a RF location tag with an individual location estimate or an individual position estimate, the receiver hub/locate engine 108 may associate a RF location tag with an individual, or may associate a tag data packet with an individual. The receiver hub/locate engine 108 could also determine a new or refined tag-individual correlator based on this association.

In one embodiment, by comparing a location estimate for a sensor with an individual location estimate or an individual position estimate, the receiver hub/locate engine 108 may associate a sensor with an individual, or may associate a sensor information packet with an individual. The receiver hub/locate engine 108 could also determine a new or refined sensor-individual correlator based on this association.

Data derived or extracted from tag signals transmitted from one or more RF location tags is referred to herein as "tag derived data" and shall include, without limitation, tag data, tag UID, tag-individual correlator, tag-sensor correlator, tag data packets, blink data, time measurements (e.g. time of arrival, time difference of arrival, phase), signal measurements (e.g., signal strength, signal direction, signal polarization, signal phase) and tag location data (e.g., including tag location estimates). Tag derived data is not derived by the RF location tag, but rather, is derived from information transmitted by the RF location tag. Information or data derived or extracted from sensor signals transmitted from one or more sensors is referred to herein as "sensor derived data" and shall include, without limitation, sensor UID, additional stored sensor data, sensor-individual correlator, environmental measurements, sensor information packets, position calculations (including sensor position estimates), position information, identity information, tag-sensor correlator, and associated sensor data. Data derived or extracted from stored individual data is referred to herein as "individual profile information", "participant profile information", or simply "profile information" and shall include, without limitation tag-individual correlator, sensor-individual correlator, identity information, name, uniform number and team, biometric data, tag position on individual. In various embodiments, the receiver hub/locate engine 108 may transmit tag derived data, sensor derived data, individual profile information, various combinations thereof, and/or any information from the GIS, the field database, the monitored area database, and the individual database to the receiver processing and analytics system 110.

Example Receiver Hub and Receiver Processing and Distribution System

Figure 4:
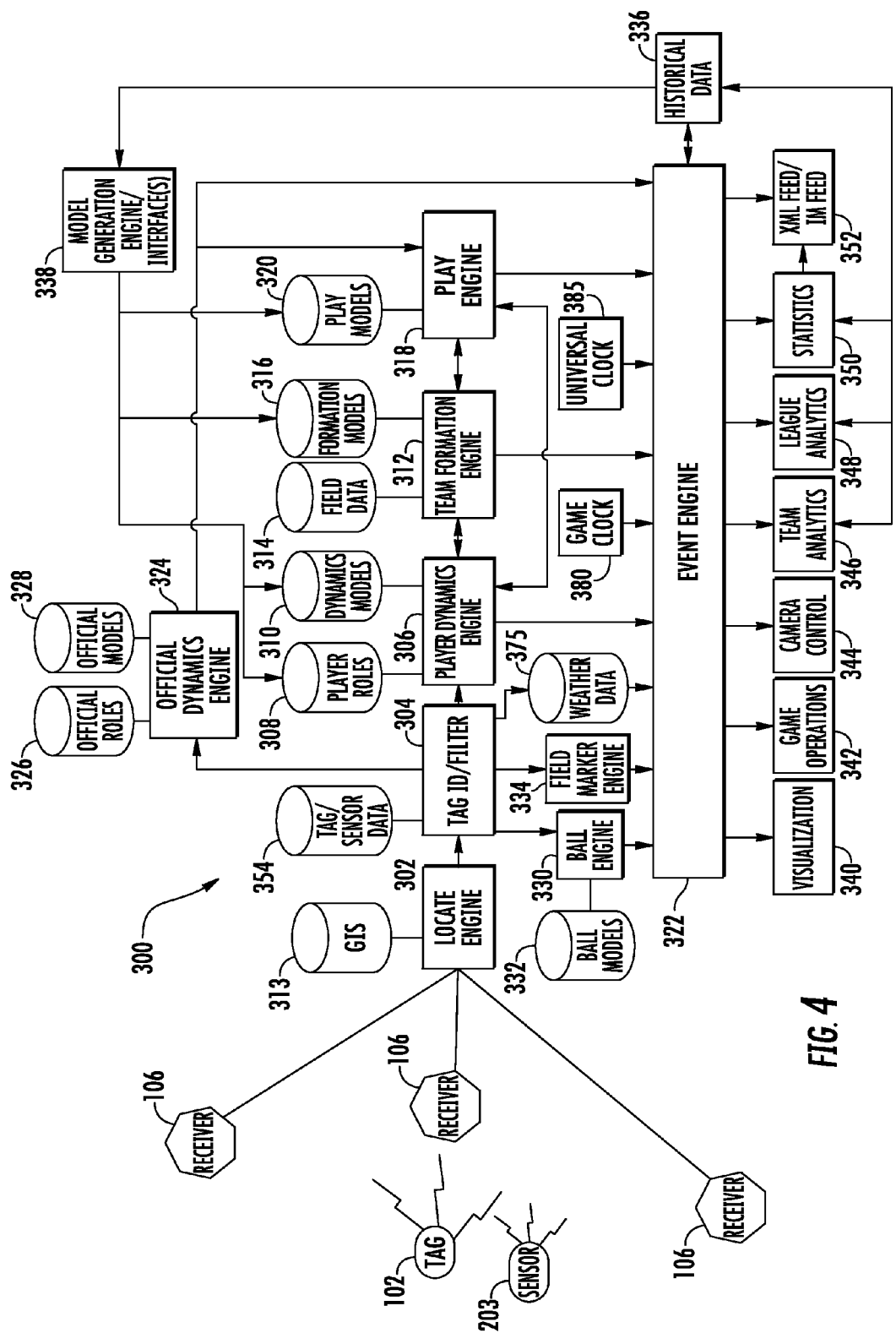
FIG. 4 illustrates an exemplary system for providing performance analytics in accordance with some embodiments of the present invention.

FIG. 4 illustrates an exemplary system 300 for providing performance analytics in accordance with some embodiments of the present invention. The depicted performance analytics system 300 may be distributed in a receiver hub 108 and a receiver processing and distribution system 110 of the type depicted in FIG. 1. For example, locate engine 302 may be part of the receiver hub 108 with the tag ID/Filter 304 through event engine 322 forming part of the receiver processing and distribution system 110. In alternative embodiments, the performance analytics system 300 may be housed or located in a single housing or unit. In still other embodiments, the performance analytics system 300 may be distributed among multiple additional housings or units depending upon the application and other design parameters that will be apparent to one of ordinary skill in the art in view of this disclosure.

The performance analytics system 300 of FIG. 4 may include a plurality of tags 102, and optional sensors 203, associated with participants (e.g., players, officials, balls, field markers, etc.), a plurality of receivers 106 positioned within a monitored environment, a receiver hub/locate engine 302, one or more filters 304, a plurality of databases, a plurality of processing engines, and a plurality of output systems. While only one type of receiver 106, other types of receivers, e.g., sensor receivers 166, 166' of FIG. 3E, may be used in accordance with the embodiments illustrated by FIG. 4. The one or more databases may include databases for tag identifiers 354, player roles 308, player dynamics or kinetics models 310, GIS data or a GIS database 313, field data or a field knowledge database 314, formation models 316, play models 320, official roles 326, official models 328, ball models 332, weather data 375, and the like. The plurality of processing engines may include a player dynamics engine 306, a team formation engine 312, a play engine 318, an event engine 322, an official dynamics engine 324, a field marker engine 334, a ball engine 330, and a model generation engine 338, or the like. The system 300 may further include a game clock 380 and a universal clock 385.

In an exemplary performance analytics system 300, such as illustrated in FIG. 4, the plurality of tags 102 (and sensors 203) may be attached to a participant as discussed in connection with FIGS. 2A-C. In some embodiments, the plurality of tags 102 and/or sensors 203 may be activated and deactivated as needed, such as before and after a game or when damaged or to replace batteries, power suppliers, local memory, etc. Each of the tags 102 may transmit a tag signal, which may include tag derived data, which is received by one or more of the receivers 106. In some embodiments, the receivers 106 may be configured with appropriate RF filters, such as to filter out potentially interfering signals or reflections proximate the field of play or other environment to be monitored.

Each of the receivers 106 may receive tag derived data from the tags 102 and transmit the tag derived data to the receiver hub/locate engine 302. The receiver hub/locate engine 302 collects the tag derived data from the receivers 106 and computes tag location data (based on the blink data) for the tags 102 as discussed above in connection with FIG. 1.

In the depicted embodiment, each of the receivers 106 receives sensor derived data from sensor signals transmitted by sensors 203. In other embodiments, sensor receivers (e.g., sensor receivers 166, 166' of FIG. 3E) may transmit sensor signals comprising sensor derived data to the receiver hub/locate engine 302.

The tag location data, tag derived data, and sensor derived data may be provided from the receiver hub/locate engine 302 to a tag ID/filter 304 that determines the type of participant associated with each received unique tag ID (and/or sensor ID) and routes the associated tag derived data (and optionally, other received tag/sensor derived data) to one or more engines associated with such participant type (e.g., player, ball, official, field marker, etc.). In one embodiment, the tag ID/filter 304 performs this routing, at least in part, by correlating the received unique tag ID (and/or sensor ID) to profile data or prior correlations (i.e., tag ID No. 0047 is correlated to participant John Smith—quarterback, sensor ID No. 12459 is correlated to Marcus Henderson—official, etc.) that may be stored to a tag/sensor identification database 354 (i.e., tag-individual correlators, sensor-individual correlators, tag-sensor correlators, etc.). In some embodiments, the receivers 106 may also receive sensor derived data for other sensors 203, such as through the tags 102 or through separate transmission means.

In one embodiment, perhaps in connection with the player illustration of FIG. 2A, the tag ID/filter 304 identifies tag location data associated with a player and thus routes such data to a player dynamics engine 306 for further processing. The player dynamics engine 306 is disposed in communication with a player role database 308, which comprises player role data correlating tag and sensor UIDs to player profiles (e.g., individual profile information) including, without limitation, which roles (e.g., quarterback, running back, flanker, slot receiver, tight end, left tackle, left guard, center, right guard, right tackle, defensive end, defensive tackle, nose tackle, inside linebacker, outside linebacker, free safety, strong safety, cornerback kicker, punter, etc.) the players perform during a game.

The player dynamics engine 306 may also be disposed in communication with a dynamics/kinetics model database 310. The player dynamics engine 306 may compare the tag location data, other tag and sensor derived data, and player role data to player dynamics/kinetics models to determine aspects of the player dynamics or movement kinetics. The dynamics/kinetics model database 310 may comprise models of different aspects or dimensions that may be based on past player location data or other data generated by the model generation engine 338 as discussed below. The models may include, without limitation, models for a particular player profile (e.g., John Smith), a player type (e.g., quarterback), a player type for a particular team (e.g., a quarterback from the Chicago Wizards), a player type for a particular formation (e.g., a quarterback in a spread offense), and the like. Such models may consider all three dimensions (x, y, z) of the tag location data for each tag (e.g., 102 of FIG. 2A) and may further consider different tag position arrays (e.g., two tag implementations—one proximate each shoulder as in FIG. 2A, eleven tag implementations—one proximate each shoulder, one proximate each elbow, one proximate each hand, one proximate each knee, one proximate each foot, and one proximate the head).

In one embodiment, the player dynamics engine 306 determines a multi-dimensional player location per unit time (e.g., participant location data) for each player based on the tag location data, other tag and sensor derived data, the player role data, and the player dynamics/kinetics models. Such multi-dimensional player location may include relative location of the player relative to the field of play, and/or general orientation of the player (e.g., standing, squatting, laying the ground, sitting, etc.) such as by correlating location data and other tag and sensor derived data.

The player dynamics engine 306 uses the real time tag location data stream from the locate engine 302, as well as the player role database 308 to provide accurate information about what a particular player is doing in real time (or near real time). The player dynamics engine 306 may further use other tag and sensor derived data, received from the locate engine 302 in the depicted embodiment, to aid in determining not only where the player is, but also how that player's location is changing with time, velocity, acceleration, deceleration, orientation, or the like. The player dynamics engine 306 outputs multi-dimensional player location information per unit time (e.g., participant location data).

In one embodiment, sensor derived data may comprise accelerometer data that may indicate that a player (or portion of a player) is accelerating or decelerating. In addition to the variety of other uses that will be apparent to one of ordinary skill in the art in view of this disclosure, the accelerometer data may be used to improve location accuracy for the system. For example, in circumstances where the real time tag location data stream erroneously suggests (perhaps due to interference, multipath effects, signal reflections, signal losses due to line-of-sight blockages, etc.) that one of the possible locations for the player is 10 feet away from a prior location, the accelerometer data could be used to confirm that the player (or accelerometer affixed portion of the player) did not experience an acceleration sufficient to move that distance in the amount of time provided.

In some embodiments, sensor derived data may comprise time-of-flight sensor data, which may indicate distances between participants (e.g., distance of a player to other players, officials, the ball, etc.) or other objects. In applications involving complex tagged object movements such as, the example football application discussed herein, time-of-flight sensor data may be used to enhance the location accuracy of the system especially in circumstances where one or more tags or sensors are temporally unable to effectively transmit their data to one or more receivers. For example, in one embodiment, a tag positioned within the ball may appear to the system as not moving because the running back carrying the ball has run into a group of other players and the bodies of such other players are actually blocking the line-of-sight transmissions of the ball tag. In this embodiment, time-of-flight sensors positioned on the group of other players may be repeatedly determining and transmitting to one or more receivers the relative distance between such time-of-flight sensors and the ball or ball carrier. In this regard, the system may determine that the ball is no longer at the ten yard line (i.e., the point where the system last received a transmission directly from the ball tag) but rather has advanced toward the opponent's end zone to the six yard line. This and other similar techniques may be used alone or in combination with other tag and sensor derived data (e.g., accelerometer data, etc.) to create a type of mesh network that may adapt to temporary or sustained line-of-sight blockages and improve the accuracy of location determinations, formation determinations, play determinations, etc.

In some embodiments, the player dynamics engine 306 outputs multi-dimensional player location information per unit time to an event engine 322. In some embodiments, the multi-dimensional player location information may include a ranked or weighted list of probable player locations while, in other embodiments, the multi-dimensional player location information includes only a top, or most probable, player location. This information may be used by the event engine 322 to determine a number of important player events. For example, the multi-dimensional player location information may be used to indicate that a player was tackled (i.e., experienced a rapid deceleration and transited from a standing to a laying position) and is subsequently limping (e.g., tag and/or sensor data from tags/sensors proximate the players feet indicate a change in the gait of the player). In such example, the event engine 322 may be configured to transmit an alert (e.g., via text message, email, or the like) to an athletic trainer to have the player checked-out or treated.

The player dynamics engine 306 may further output the multi-dimensional player location information per unit time (e.g., participant location data) to a team formation engine 312. The team formation engine 312 is disposed in communication with a formation models database 316 that contains models of various formations (e.g., offensive formations, defensive formations, special teams formations, etc.) defined for the relevant sport or activity (e.g., football in the depicted embodiment). The models of various formations may be derived from multi-dimensional player location information collected during prior games, practices, etc., (e.g., learned by the system) or as input by one or more teams, such as by using model generation engine 338, historical data store 336, and/or team analytics engine 346.

The team formation engine 312 is further disposed in communication with a field data database 314 to assist in determining the likely team formations. The field data database 314 may comprise, without limitation, survey data for the field (e.g., various distances or coordinates from reference tag(s) or other marker to yard lines, end zones, goal posts, boundaries, benches, locker rooms, spectator areas, other zones of interest, etc.).

In one embodiment, the team formation engine 312 determines one or more formations (e.g., a probable formation or a ranked or weighted list of probable formations) based at least in part on the field data, the multi-dimensional player location information (which may include the tag derived data and/or sensor derived data), and the formation models. The team formation engine 312 may hypothesize the received multi-dimensional player location data against models of every known formation to determine a probable formation or a ranked or weighted list of probable formations. The team formation engine 312 is thus configured to determine and output a data stream of formations versus time, which considers how various formations change and may be used by downstream engines to determine various events including the occurrence of a play.

In one embodiment, the team formation engine 312 may assign weights to the received multi-dimensional player location data (i.e., participant location data), other types of tag derived data and/or sensor derived data, and/or to the formation models when determining a specific formation or ranked list of probable formations. For example, in one embodiment, the team formation engine 312 may be configured to assign a greater weight to the position of the ball (which should remain stationary for a period of time as formations are being established, i.e., at the beginning of a play) than to the position of an official (which may move to some degree as formations are forming). In another embodiment, the team formation engine 312 may be configured to assign a greater weight to the location of the tight-end (which may indicate the strong side of a formation) than to the location of a left guard (whose location seldom effects formation determination). In still another embodiment, the team formation engine 312 may be configured to assign a greater weight to sensor derived data associated with an accelerometer positioned proximate an official's wrist (which may indicate winding of the play clock that often triggers the period during which formations ought to be forming) than to the location of any player.

In one embodiment, the team formation engine 312 outputs the data stream of formations versus time (e.g., formation data) to the play engine 318. The play engine 318 may also receive the output data stream (e.g., multi-dimensional player location information versus time) from the player dynamics engine 306. The play engine 318 is disposed in communication with a play models database 320. The play models database 320 may include play models (e.g., known formation shifts or movements over time). Such play models may be programmatically learned by the system (e.g., based on actual movements of players tracked by the system) or manually entered through an interface or other tool (e.g., perhaps through the model generation engine 338). In this regard, the play models database 320 may include historical plays executed by teams, potential/future plays from a team game plan or playbook, or other historical data (e.g., from historical data store 336).

In one embodiment, the play engine 318 may take the formations versus time data stream from the formation engine 312, the play models, and the player dynamics data stream (which may include tag location data and/or other tag and sensor derived data) to determine whether a play is forming, a play has started, a play is in progress, or a play has ended. For example, the play engine 318 may determine that it is most likely that a pre-snap formation at the line of scrimmage has occurred (e.g., an offensive team has aligned in a "pro set" formation and a defensive team has aligned in a "3-4" formation) indicating a play is about to begin. The play engine 318 may thereafter determine that the offensive and defensive players have begun rapidly accelerating towards and across a line of scrimmage thereby indicating that a play has begun. The play engine may further determine that an offensive player has been tackled by a defensive player thereby indicating that a play has concluded.

In some embodiments, the play engine 318 may use assigned weights (or assign weights) to the received data (e.g., the tag derived data, the sensor derived data, the multi-dimensional player location data, the formations data, officials data, etc.) for use in analyzing the data and determining the most probable play events. For example, the play engine 318 may determine that data for particular participants (e.g., a left guard) has a lower relevance for a particular formation (e.g., a pro set offensive formation) and assign a lower weight to that data during the analysis than to another participant (e.g., the ball, the quarterback, a wide receiver, etc.).

In some embodiments, the play engine 318 is disposed in communication with an official dynamics engine 324 to further improve the play determination accuracy of the system. The official dynamics engine 324 may provide data about the movements, actions, positions of an official, which the play engine 318 may use when determining a probable play and/or the status of a play. For example, as discussed in connection with FIG. 2B above, an official may be provided with wrist based accelerometers or other sensors (e.g., a whistle sensor), which may be used to flag the beginning or ending of a given play based on the movement or action of an official (e.g., rotating an arm to wind the play clock, indicate touchdown with two arms raised, blow a whistle, etc.).

The play engine 318 may analyze how the team formations occur and how they break up to determine both start and stop of a play (e.g., start of play event, end of play event, etc.). For example, the play engine 318 may determine that offensive and defensive formations coalesced proximate a line of scrimmage and then broke up with various receivers heading towards the defensive team's end zone, there was all kinds of activity around a quarterback which eventually dissipated, and that defense players were tracking one of the receivers downfield until the receiver crossed into the end zone and an official raised his arms. The play engine 318 may determine that this participant activity best fits a play model whereby a ball was thrown and caught by a receiver who then scored a touchdown thereby ending the play.

In some embodiments, the play engine 318 may hypothesize the received multi-dimensional player location data (e.g., participant location data) and the data stream of formations versus time against models of every known play to determine a probable play or a ranked list of probable plays. The play engine 318 is thus configured to determine and output a data stream of plays versus time, which may be communicated to the event engine 322.

In some embodiments, the tag ID/filter 304 may determine that received tag derived data and/or sensor derived data corresponds to one or more officials. Such official correlated tag/sensor derived data is routed to the official dynamics engine 324. The official dynamics engine 324 is disposed in communication with an official roles database 326, which comprises official roles data correlating tag and sensor IDs (or other tag/sensor individual correlators) to official profiles including, without limitation, which roles (e.g., referee, umpire, head linesman, line judge, back judge, field judge, side judge, etc.) the officials perform during a game.

The official dynamics engine 324 may also be disposed in communication with a dynamics/kinetics model database 328. The official dynamics engine 324 may compare the tag location data, other tag/sensor derived data, and official role data to official dynamics/kinetics models to determine aspects of the official dynamics or movement kinetics. The dynamics/kinetics model database 328 may comprise models of different aspects or dimensions that may be based on past official location data or other data generated by the model generation engine 338 as discussed below. The models may include, without limitation, models for a particular official profile (e.g., Ralph Stevens), an official type (e.g., referee), an official type for a particular formation (e.g., a referee positioned during a kickoff), and the like. Such models may consider all three dimensions (x, y, z) of the tag location data for each tag (e.g., 102 of FIG. 2B) and may further consider different tag position arrays (e.g., two tag implementations—one proximate each shoulder as in FIG. 2B, eleven tag implementations—one proximate each shoulder, one proximate each elbow, one proximate each hand, one proximate each knee, one proximate each foot, and one proximate the head).

In one embodiment, the official dynamics engine 324 determines a multi-dimensional official location per unit time for each official based on the tag location data, other tag and sensor derived data, the official role data, and the official dynamics/kinetics models. Such multi-dimensional official location may include (1) a relative location of the official relative to the field of play, (2) a general orientation of the official (e.g., standing, squatting, laying the ground, sitting, etc.), and (3) a specific orientation of the official (e.g., arms raised, arms at hips, one hand grasping the wrist of the other arm, etc.).

The official dynamics engine 324 uses the real time tag location data stream from the locate engine 302, as well as the official role database 326 to provide accurate information about what a particular official is doing in real time (or near real time). The official dynamics engine 324 may further use tag and sensor derived data, received from the locate engine 302 in the depicted embodiment, to aid in determining not only where the official is, but also how that official's location is changing with time, velocity, acceleration, deceleration, orientation, or the like. For example, in one embodiment, the sensor derived data may comprise accelerometer data that may indicate that an official (or portion of an official) is accelerating or decelerating. The official dynamics engine 324 outputs multi-dimensional official location information per unit time. Such multi-dimensional official location information may include information regarding the official's location, how the location is changing with time, orientation of the official, motions or gestures of the official, or the like.

In some embodiments, the tag ID/filter 304 may determine that received tag and/or sensor derived data corresponds to the game ball (e.g., a ball such as the ball shown in FIG. 2C, which is used or capable of use in the field of play). Such ball correlated tag/sensor derived data is routed to the ball dynamics engine 330. While the ball engine 330 is not shown in communication with a "roles" database as in the case of some of the other processing engines, one of ordinary skill in the art will readily appreciate some ball role data may be used, such as a ball ID or the like, indicating that the received tag/sensor derived data is associated with a given ball.

The ball engine 330 may access a ball models database 332, which comprises data indicating how location data and other tag and sensor derived data correlates to particular ball events during play. The ball engine 330 may provide information regarding the ball's position/location (vertical and/or horizontal), how the location is changing with time, the velocity of the ball, the rotation of the ball, or the like for determining events during play. The ball engine 330 may output ball data streams to the event engine 322. In some embodiments, although not shown in FIG. 3, the ball engine may also output a data stream to other processing engines for analysis, such as to the play engine 318 for use in determining status of a play.

In some embodiments, the tag ID/filter 304 may determine that received tag and/or sensor derived data corresponds to a field marker (e.g., penalty flags, line of scrimmage markers, yards to gain markers, and the like). The tag ID/filter may then route such field marker correlated tag/sensor derived data to a field marker engine 334 for further processing. The field marker engine 334 may provide information regarding field marker location, how the location is changing with time, or the like, for determining events during play. The field marker engine 334 may output data streams to the event engine 322. In some embodiments, although not shown in FIG. 3, the field marker engine may also output a data stream to other processing engines for analysis, such as to the play engine 318 for use in determining the status of a play.

In some embodiments, a game clock 380 may be provided that is configured to keep an official time for a game or other tracked activity. In applications such as the depicted football application, the game clock is configured to count down from some standard period or quarter length (e.g., 15 minutes) and may be periodically stopped or started by one or more officials and/or the game operations system 342 as discussed in greater detailed below. While not separately illustrated in FIG. 3, the game clock 380 may further include a play clock, shot clock, pitch clock, or the like, which depending upon the application, may also be started and stopped by one or more officials and/or the game operations system 342.

The universal clock 385 provides a system time for the performance and analytics system 300. As will be apparent to one of ordinary skill in the art in view of this disclosure, the universal clock 385 is running clock for tracking, cataloging, and calibrating system actions, processes, and events. For illustrations purposes, the game clock 380 and the universal clock are shown as inputs for the event engine 322; however, in other embodiments, such clocks may provide inputs to any or all of the player dynamics engine 306, the team formation engine 312, the play engine 318, the event engine 322, the official dynamics engine 324, the field marker engine 334, the ball engine 330, and the model generation engine 338.

An event engine 322 may receive the outputs from the player dynamics engine 306, the team formation engine 312, the play engine 318, the official dynamics engine 324, the ball engine 330, the field marker engine 334, the weather data store 375, a game clock 380, and a universal clock 385 to determine events occurring during game play or to perform analytics, including predictive analytics, on game related data. In some embodiments, the event engine 322 determines such events and performs such analytics by comparing its received inputs to a historic data store 336 containing past events or analytics. In some embodiments, the event engine 322 outputs event data streams (e.g., one or more output events) to a number of systems including, without limitation, a visualization system 340, a game operations system 342, a camera control system 344, a team analytics system 346, a league analytics system 348, a statistics system 350, an XML feed and/or instant message feed 352, a historical data store/engine 336, or other systems as may be apparent to one of ordinary skill in the art in view of this disclosure.

In some embodiments, the event engine 322 may output event data streams that include the time delay between tag and/or sensor transmissions and the determination of the events such that other processes, such as a visualization system, game operations system, etc., may properly correlate to different inputs (e.g., video recording versus the determined events) so that the different inputs are synchronized. In other embodiments, the event data streams may include time stamps (game time stamp, universal time stamp, etc.) for determined events or other system processes. In this way, the performance and analytics system 300 or some downstream system can determine, inter alia, which events or processes occurred in-game (i.e., during a running game or play clock) or out-of-game (i.e., while the game or play clock were stopped).

In various embodiments, the event data streams or output events provided by the event engine may include tag events (e.g., battery low indication, error indication, etc.), sensor events (e.g., battery low indication, error indication, etc.), locate engine events (e.g., status indications, error indications), tag ID/Filter events (e.g., status indications, error indications), player dynamics engine events (e.g., status indications, error indications), player events (e.g., player tackled indication, player injured indication, etc.), official dynamics engine events (e.g., status indications, error indications), official events (e.g., official injured indication, etc.), ball engine events (e.g., status indications, error indications), ball events (e.g., new ball required indication, etc.), team formation engine events (e.g., status indications, error indications), team formation events (e.g., formation type indication, new formation indication, illegal formation indication, etc.), play engine events (e.g., status indications, error indications), play events (e.g., play type indications such as run, pass, punt, field goal, etc., play results, and in-play or sub-play events such as bootleg, 3 step drop, 5 step drop, 7 step drop, crossing pattern, hook pattern, fly pattern, drive block, pass block, spin move, swim move, press coverage, zone coverage, etc.), or any other events that may be apparent to one of ordinary skill in the art in view of this disclosure. A variety of additional event data streams or output events are described in connection with the analytics systems and control systems discussed below.

In one embodiment, the event engine 322 outputs an event data stream to the visualization system 340 that may be used by the visualization system to provide enhanced telecasts or game experiences for television broadcasts, streaming mobile device clients, and other media outlets, gaming systems, and other computer graphics visualization systems. Such event data streams may be used to provide enhanced graphics, displays, information, visualizations, and the like. For example, and without limitation, the visualization system 340 may receive real time (or near real time) data including, without limitation, player ID, official ID, team ID, formation identifiers, play identifiers, pre-snap play probabilities, play diagrams, player route data, player speed data, player acceleration data, ball route date, ball speed data, ball acceleration data, player trend information, offensive team trend information, defensive team trend information, special teams trend information, and other tag and/or sensor derived data. In some embodiments, the visualization system 340 may be configured to provide a dynamically configurable interface that may be engaged by a user to select graphics or areas of focus. For example, in one embodiment, a user may configure the system to display possible passing lanes for a quarterback to his eligible receivers. In still other embodiments, the visualization system 340 may output a data stream for use in gaming systems, such as plays, player actions, or the like.

In gaming systems examples, the visualization system 340 may provide output of event data that may be configured for display via a gaming console or handheld device. Such visualization system outputs may, for example, provide for incorporating actual or predicted actions of a "live" player into a gaming environment. In some embodiments, the visualization system may also access stored computer generated or user created avatars for use with the event data stream.

In one embodiment, the event engine 322 outputs an event data stream to the game operations system 342 that may be used by the game operations system to coordinate, manage, or assist in the coordination or managing of game operations including, without limitation, the game clock 380 (and optionally the play clock), down and distance determination, score board operations, penalty enforcement, and the like. For example, and without limitation, the game operations system 342 may receive real time (or near real time) data from the event engine 322 including, without limitation, a clock start indication, a clock stop indication, a play start indication, a play end indication, a reset play clock indication, a $1^{st}$ down indication, a $2^{nd}$ down indication, a $3^{rd}$ down indication, a $4^{th}$ down indication, a turnover indication, a yard to gain indication, a 5 yard penalty indication, a 10 yard penalty indication, a 15 yard penalty indication, an end of quarter indication, an end of half indication, and an end of game indication.

Said differently, the event engine 322 may determine a number of events that may be output to the game operations system or other devices. Such events may include, without limitation, a ready for play event (e.g., an official has spotted the ball at the line of scrimmage and started a play clock in a football example, a pitcher has received the ball from his catcher in a baseball example, or the pins have been set in a bowling example), a start of play event (e.g., the ball has been snapped in a football example, the pitcher has begun his pitching motion or wind-up in a baseball example, or a bowler has begun his bowling motion in a bowling example), and an end of play event (e.g., the official has blown a whistle in a football example, an umpire has called a third strike in a baseball example, or the nine pins have been knocked down in a bowling example). Such events may be used to determine plays, formations, and to output play diagrams (e.g., graphs or plots of participant location versus time from a start of play event to an end of play event).

The event engine 322 may be further configured to output a play result to the game operations system 342 or other device. Such play results may include, for example and without limitation, a gain of twelve yards, a loss of three yards, an interception, a touchdown, a first down, and the like in football embodiments; a ball, a strike, a fly-out, a single, a double, a home run, a run scored, and the like in baseball embodiments; and a gutter, a strike, a spare, and the like in bowling embodiments.

As would be apparent to one of skill in the art, the various engines and/or output systems may include security measures, such as encryption, access permissions, and the like, to secure system inputs and outputs. In some embodiments, the engines and/or output systems may comprise security measures to prevent hacking, jamming, transmission interception, etc. to prevent interference from outside parties, such as third parties attempting to gain information that may be advantageous in wagering, for example.

In one embodiment, the event engine 322 outputs an event data stream to the camera control system 344 that may be used by the camera control system to engage or transition engagement between one or more television, film, or other cameras to capture game events. For example, and without limitation, the camera control system 344 may receive real time (or near real time) data including, without limitation, an engage or disengage camera 1 indication, an engage or disengage camera 2 indication, an engage or disengage camera 3, . . . and an engage or disengage camera n indication. In some embodiments, the event engine 322 may output camera control indications (e.g., event data) based on real time (or near real time) game activity (e.g., ball location data suggests that the ball is closest to a known field of view for camera 4 and, thus, an engage camera 4 indication is transmitted to the camera control system 344). In other embodiments, the event engine 322 may output camera control indications (e.g., event data) based in part on a prediction of game activity (e.g., ball position, acceleration, and direction data suggests that the ball has just left the quarterback's hand and is being passed along a direction and at a velocity indicative of being caught in the field of view of camera 4 and, thus, an engage camera 3 indication is transmitted to the camera control system 344). In other embodiments, the camera control system 344 may provide indications such as to tilt, pan, or zoom in connection with a particular camera based on event data or predicted actions, or set a location or point of view based on where a player, formation, or play may be best viewed.

In one embodiment, the event engine 322 outputs an event data stream to the team analytics engine 346 that may be used to generate real time (or near real time) analytics (e.g., player performance information, formation performance information, play performance information, and team performance information) concerning game activity that may be useful to individual teams. For example, in one embodiment, the team analytics engine 346 may use event data to determine actual game performance versus playbook design including, without limitation, an evaluation of player routes, offensive, defensive, and special teams formations, offensive blocking protection schemes, defensive blitzing schemes, and the like.

In another embodiment, the team analytics engine 346 may use event data to determine actual game performance versus historical game performance (such as by using historical data store 336) including, without limitation, an evaluation of game performance (e.g., player, team, offense, defense, special teams, etc.) versus prior year performance, prior game performance, prior quarter performance, prior possession performance, prior play performance, and the like. In this regard, as will be apparent to one of ordinary skill in the art, the team analytics engine 346 may be used to evaluate performance (e.g., the left tackle has missed three assignments), identify trends (e.g., the defensive team consistently sends a linebacker blitz against a spread offensive formation), make player substitutions (e.g., a second string left tackle has performed better historically against the right end of the defense and thus should be substituted for the starting left tackle), revise game plans, or provide alerts (e.g., the flanker has experienced significantly reduced speed, acceleration, and performance following being tackled and thus an alert should be generated to the training staff to ensure that such player is medically evaluated).

For example, in one embodiment, a trainer may have a device, such as a handheld device, tablet, etc., that may receive alerts regarding a particular player. The trainer may receive background information and/or past information on a player as well as what change the system has identified to cause the alert, such as a change in gait, slower route running, etc. The trainer may then be able to evaluate the player and provide input to the system regarding the player evaluation, such as if further attention is required or if the player can return to play. In some embodiments, such alert and evaluation results may also be provided to the league analysis system, such as for use in determining injury trends or the like.

In some embodiments, the team analytics engine 346 may be used to alert a team (e.g., coaches) to focus on specific players who are performing sub-par versus their normal (historical) performance, such as by plays or by teams. In some embodiments, the team analytics engine 346 may further output analysis results to the historical data store 336 or the like, for use in future analysis and/or the building or updating of various models.

In one embodiment, the performance and analytics system is configured to evaluate player performance by correlating at least one tag to the player; receiving blink data (and other tag derived data) transmitted by the at least one tag; determining tag location data based on the blink data; receiving player role data; comparing the tag location data to player dynamics/kinetics models based at least in part on the player role data; determining player location data based on the comparing the tag location data to the player dynamics/kinetics models; and determining player performance information based on comparing the player location data to stored player location data. In some embodiments, the stored player location data may be stored to the historical data store 336 and may include player location data for the actual player to be evaluated (e.g., Frank Smith, left tackle, #55) and/or player location data for another player (e.g., Fred Johnson, left tackle, #65) who plays a similar position to the actual player to be evaluated. In still other embodiments, the stored player location data may include competitive data based on the performance of the actual player against an opposing player (e.g., the left tackle blocked the right defense end successfully in five prior matchups, the defensive back caused a delay by the wide receiver of 2 seconds in running a passing route by applying press coverage, etc.).

In another embodiment, the performance and analytics system is configured to evaluate official performance by correlating at least one tag to the official; receiving blink data (and other tag derived data) transmitted by the at least one tag; determining tag location data based on the blink data; receiving official role data; comparing the tag location data to official dynamics/kinetics models based at least in part on the official role data; determining official location data based on the comparing the tag location data to the official dynamics/kinetics models; and determining official performance information based on comparing the official location data to stored official location data. In some embodiments, the stored official location data may be stored to the historical data store 336 and may include official location data for the actual official to be evaluated and/or official location data for another official who held a similar position (e.g., referee, umpire, etc.) to the actual official to be evaluated.

In one embodiment, the event engine 322 outputs an event data stream to the league analytics engine 348 that may be used to generate real time (or near real time) analytics concerning game activity that may be useful to a league (i.e., a collection of teams). For example, in one embodiment, the league analytics engine 348 may use event data to improve game safety by identifying injury trends (e.g., player concussions occur at a higher rate when an offensive team runs crossing passing routes from a spread formation against a 3-4 defense, etc.). In another embodiment, the league analytics engine 348 may use event data to evaluate rule changes (e.g., a rule change intended to speed up game play is or is not achieving its intended result). In still another embodiment, the league analytics engine 348 may use event data to improve officiating (e.g., determining the accuracy of official calls). In some embodiments, the league analytics engine 348 may further output analysis results to the historical data store 336 or the like, for use in future analysis and/or the building or updating of various models.

In one embodiment, the event engine 322 outputs an event data stream to the statistics engine 350 that may be used to generate real time (or near real time) statistics concerning game activity. Such statistics may include, without limitation, offensive statistics (e.g., passing, rushing, receiving, turnovers, touchdowns scored, etc.), defensive statistics (e.g., tackles, sacks, interceptions, turnovers generated, etc.), special teams statistics (e.g., punt length, punt hang time, average return, long return, field goal accuracy, etc.), play diagrams, length of play statistics (e.g., 4.8 second average play, 22 second average pre-snap formation period, etc.), player participation statistics (e.g., John Smith participation in 42 of 68 offensive plays, etc.), summary statistics (e.g., top scorers, fantasy points, minutes on offense, etc.), official statistics (e.g., penalties called, location tracking diagrams per play, etc.) and the like. In some embodiments, the statistics engine 350 may further output statistics and results to the historical data store 336 or the like, for use in future analysis and/or the building or updating of various models.

In one embodiment, the event engine 322 outputs an event data stream to the XML feed and/or instant messaging feed engine 352 that may be used to generate XML or instant messaging data streams that may include live data such as plays, scoring plays, other scoring info, results, top scorers, summary statistics, or the like.

In one embodiment, the event engine 322 may output an event stream that may be used to annotate or tag a game recording, for example, using visualization system 340, game operations system 342, or the like. For example, in one embodiment, the event engine 322 may flag, tag, or annotate certain events (e.g., plays, penalties, formations, clock start/stop, etc.) into a video recording or live data stream of a game for later playback or analysis. In some embodiments, any event identified by the event engine 322 may be flagged, tagged, or annotated to a video or other data stream to provide for ease of later identification. In this regard, various events may be readily searched, identified, stored to a database in an indexed way, and/or analyzed.

In some embodiments, the event engine 322 may determine events occurring proximate one or more play boundaries. For example, using outputs from the player dynamics engine 306, the ball engine 330, and the official dynamics engine 324 the event engine 322 may determine that a touchdown has been scored (i.e., a player has carried the ball across a goal boundary into the endzone). In particular, the event engine 322 may determine that a running back carried the ball (based on location data received from the ball engine and the player dynamics engine) across the goal boundary (based on field data), which was confirmed by the nearest official signaling touchdown by raising both arms (based on location data received from the official dynamics engine).

In some embodiments, the event engine 322 may output an event data stream to a historical data store/engine 336, which may store data generated by the various processing engines over time. The historical data store/engine 336 may be accessed by various systems, such as for use in providing analytics or generating new models. For example, historical data store/engine 336 may provide historical data to model generation engine 338, which the model generation engine 338 may use in learning (or developing) new play or formation models that should be added to the respective model databases. In some embodiments, the historical data store/ engine 336 may be accessed by the analytics and statistics systems to generate more in-depth analytics or statistics. In some embodiments, the historical data store 336 may comprise prior event and tag derived data received by the system for each individual player (e.g., John Smith) and may also comprise player data received from other sources, such as from manual input tools (i.e., such as using a form or template) or external data sources (e.g., other statistics databases, etc.).

In some embodiments, the event engine 322 may output an event data stream that may be used in conjunction with historical results, such as from historical data store 336, for determining odds for outcomes of various team matchups. For example, the event data stream and historical event data may be analyzed to generate and/or change predicted odds for outcomes of each play, etc., which may be used in a wagering system or the like.

In some embodiments, the team analytics system 346 may provide an interface tool (i.e., perhaps through the model generation engine 338) configured to allow a team to input future plays (i.e., a game plan). Such future plays may be tested against historical data stored to the historical data store 336 in order to determine a probability for success. For example, the team analytics system 346 may be configured to allow a team to virtually test an individual play intended to be run from a given offensive formation against defenses that were historically run against such offensive formation. As will be apparent to one of ordinary skill in the art in view of this disclosure, the team analytics system 346 may be configured to allow a team to virtually test its game plan against another team, specific players, specific formations, specific blocking protections, specific blitz packages, specific weather conditions, and the like.

In one embodiment, the team analytics system 346, or any other engine or system, may be configured with access security controls (e.g., password protection schemes, etc.) sufficient to limit access to team proprietary data (e.g., game plan information, player injury data, etc.) to individual teams. In this regard, game integrity may be preserved by ensuring that proprietary data of a first team is not obtained by a competing second team.

In some embodiments, the event engine 322 and its corresponding output systems (i.e., the visualization system 340, the game operations system 342, the camera control system 344, the team analytics system 346, the league analytics system 348, the statistics system 350, the XML feed/IM feed system 352, and the historical data store/engine 336) may be configured to provide different levels of specificity for the output data. For example, an individual team may receive output data breaking down the specific details for each play and the player dynamics for the play, such that the team may determine the performance of each player in executing the specifics of a play versus an intended design. In contrast, similar yet less detailed output may be provided to all teams such as basic play diagrams and standard statistics for the players.

In some embodiments, one or more of the engines shown in FIG. 3, such as, without limitation, the team formation engine, the play engine, the event engine, or the like, may output lists or ranked lists of probable output events (e.g., locations, formations, plays, events, etc.) for display to a user via a graphical user interface (e.g., PC, tablet, mobile device, etc.) and/or for use by downstream engines or systems. In other embodiments, the above described engines may select from the ranked list of probable events a most probable event, or more simply a "probable event" (e.g., probable location, probable formation, probable play, probable blocking technique, probable passing route, etc.), that either has the highest probability indicator among the ranked list or has a probability indicator above a pre-defined threshold.

In some embodiments, the user may validate or confirm an output event (e.g., a location, a formation, a play, or an event) to improve system operation. For example, in one embodiment, the event engine 322 may determine that the following events may have occurred each with a respective probability indicator shown in parenthesis: completed pass—12 yard gain for the offense (68%); completed pass—10 yard gain for the offense (21%); incomplete pass—0 yard gain for the offense (19%). This ranked list may be displayed to an official via a mobile device who may select and confirm the correct output event, which in this example is the completed pass for a 12 yard gain for the offense. In this regard, as will be apparent to one of ordinary skill in the art in view of this disclosure, the system may employ a user to break ties or close calls (e.g., probabilities within 10 percent, etc.) or to improve the accuracy of models, input weighting allocations, and the like.

In still other embodiments, the performance and analytics system may determine or predict participant locations, formations, plays, or other events despite temporary or sustained losses of blink data for one or more tags (e.g., due to transmission failures associated with multipath effects, line-of-sight blockages, etc.). For example, in one embodiment, the performance and analytics system: receives first tag location data for a first participant (e.g., a ball carrier) during a first time period (e.g., an in-play period representing the first 3 seconds of a play); receives subsequent first tag location data for the first participant during a second time period (e.g., a second in-play period representing the second 3 seconds of a play); receives second tag location data for a second participant (e.g., the ball carried by the ball carrier) during the first time period; and determines (or predicts) subsequent second tag location data for the second participant during the second time period based at least on: the first tag location data for the first participant during the first time period, the subsequent first tag location data for the first participant during the second time period, and the second tag location data for the second participant during the first time period.

The above determination or prediction may be further improved using tag derived data and sensor derived data. For example, the performance and analytics system may receive first sensor derived data (e.g., time-of-flight sensor data or other tag and sensor derived data suggestive of a relative proximity between the first participant and the second participant) for the first participant during the first time period; receive subsequent first sensor derived data for the first participant during the second time period; and determine the subsequent second tag location data for the second participant during the second time period further based at least on: the first sensor derived data for the first participant during the first time period, and the subsequent first sensor derived data for the first participant during the second time period.

In still other embodiments, the above determination or prediction of second participant location may be improved by comparing participant location at various times to formation and/or play models. Such comparisons may further include field data, and participant role data. For example, if we maintain the above example whereby the first participant is a ball carrier and the second participant is a ball, the performance and analytics system may determine or predict the location of the ball (i.e., in circumstances where tag or sensor transmissions from the ball are blocked) during a pre-snap period by determining that the ball carrier is aligned in a stationary location in the backfield. By comparing such ball carrier location data to formation models, the system may determine that the ball is most likely positioned at the line of scrimmage proximate the center.

Similarly, in another embodiment, perhaps where the first participant is a quarterback and the second participant is a left guard, the performance and analytics system may determine or predict the location of the left guard in any given play or time period based upon comparing movements of the quarterback to formation and play models. For example, quarterback movement from a snap position to a drop back passing position may be suggestive that the left guard is positioned in a pass blocking position proximate the line of scrimmage. Alternatively, quarterback movement from a snap position to a hand-off position may be suggestive that the left guard is positioned up field of the line of scrimmage in a run blocking position.

Figure 5:
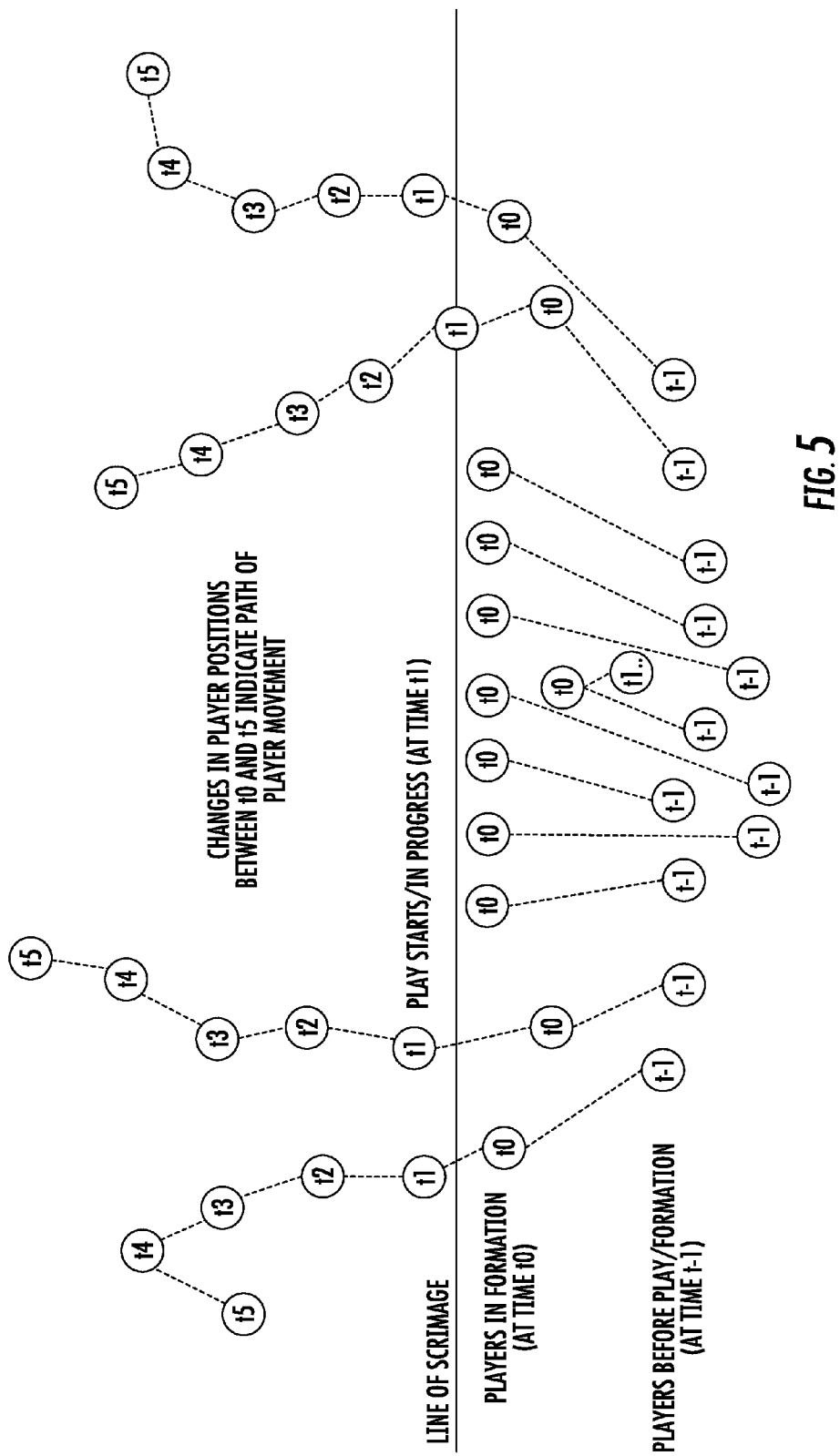
FIG. 5 illustrates example participant tracking over time in accordance with some embodiments of the present invention.

FIG. 5 illustrates example participant (e.g., player) tracking over time in accordance with some embodiments of the present invention. More specifically, FIG. 5 illustrates the changing position of an offensive team during game action. Such tracking of changing positions may be useful for various engines of the present system including, without limitation, the player dynamics engine, the formation engine, the play engine, and the event engine. For example, at a first time, t-1 (e.g., game clock: 12:26, play clock: 38 seconds, universal clock: 16:09:30), the tag location data may indicate that the tracked offensive players are positioned well behind the line of scrimmage, thus, suggesting a low probability of any present formation. However, at a second time, t0 (e.g., game clock: 12:01, play clock: 13 seconds, universal clock: 16:09: 55), certain of the tracked players (e.g., offensive linemen and receivers) appear to have positioned themselves proximate the line of scrimmage, thus, suggesting a higher probability of a pro set offensive formation. At a third time, t1 (e.g., game clock: 11:55, play clock: 07 seconds, universal clock: 16:10: 01), certain tracked players (e.g., the receivers and the quarterback) move away from the line of scrimmage, thus, suggesting that a play has begun. Additional times t2 through t5 may be similarly tracked as shown and used by the various engines to hypothesize the occurrence of particular events (formations, play start/stop, penalties, etc.). The tag location data recorded at times t-1 through t5 may provide for a data stream indicating the motions/paths of the various players throughout the duration of a play period. It is noted that FIG. 5 does not illustrate tracking of all the players after t0, or the defensive team players, in order to simplify the illustration.

The team formation engine 312 and/or play engine 318 may analyze player dynamics of multiple players, both offensive and defensive, simultaneously in hypothesizing the possible formations, plays, etc. For example, as discussed briefly above, the formation engine 312 and/or play engine 318 may apply different weights to the tag/sensor/location data received for each player based in part on the player's role versus the formation models or play models, as all the individual player dynamics may not fully correlate to a particular formation or play. The formation engine 312 and/or play engine 318 may then analyze the different models and choose the model, or set of models, that have the highest probability of being accurate based on the weights of all the combined inputs.

Example Dynamic Weighting by Various Engines

Various engines of the above described performance analytics system such as the player dynamics engine, the official dynamics engine, the ball engine, the field marker engine, the team formation engine, the play engine, and the event engine, may dynamically assign and adjust various weights to respective inputs (e.g., tag derived data, sensor derived data, participant location data, formation data, play data, etc.) in order to efficiently make their respective determinations or calculations. In some embodiments, as discussed in great detail below, one of the engines may use data or events output from one or more of the other engines when determining to assign or adjust the various weights to the respective inputs.

For example, in one embodiment, the player dynamics engine may receive a pre-snap or pre-play indication from the team formation engine indicating that the offensive and defensive players are aligned proximate the line-of-scrimmage and that a play is about to begin. The player dynamics engine may determine because the players are tightly packed in pre-snap or pre-play positions that some tags or sensors (e.g., those transmitting proximate the player's feet) may have a lower probability of communication effectiveness based on line-of-sight blockages due to player bodies. This determination may, in some embodiments, be confirmed by polling of the tags or sensors in question by one or more receivers.

If the default weight (i.e., a first weight) for data for all tags and sensors of the system is 1.0, the player dynamics engine may assign a weight of 0.1 (i.e., a second weight) to the lower communication effectiveness tags or sensors. In an alternative embodiment, other tags or sensors (e.g., time-of-flight sensors, accelerometers, etc.) that are deemed more important given the poor communication of the lower communication effectiveness tags or sensors may be assigned a weight of 1.5.

The weights of the various tags and sensors may be used by the player dynamics engine, or other downstream engines such as the team formation engine, the play engine, or the event engine, to reduce the impact of the lower communication effectiveness tags or sensors (or increase the impact of other tags or sensors) on the determinations or calculations of such engines. In some embodiments, such weights may be used to allow the performance analytics system to allocate resources (e.g., power, computational resources, etc.) away from lower communication effectiveness tags or sensors to enhance battery life or system performance.

In some embodiments, the low communication effectiveness of the tags or sensors may be short-lived, for example, once a play begins the players begin to spread out making communication with even foot attached tags easier. In one embodiment, the player dynamics engine may receive a snap or play start indication (e.g., indication a second time if the previously discussed pre-snap or pre-play indication indicated a first time) and, in response, may assign the default weight of 1.0 to the prior low communication effectiveness tags or sensors thereby causing the performance analytics system to consider equally the tag derived data or sensor derived data resulting from such tags or sensors.

In some embodiments, a receiver may derive data from a plurality of tags and thus may transmit tag derived data having a first tag derived data component (e.g., tag derived data based on blink data transmitted by a first tag) and a second tag derived data component (e.g., tag derived data based on blink data transmitted by a second tag). In some embodiments, a receiver may derive data from a plurality of sensors and may transmit sensor derived data having a first sensor derived data component (e.g., sensor derived data based on a sensor data packet transmitted by a first sensor) and a second sensor derived data component (e.g., sensor derived data based on a sensor data packet transmitted by a second sensor). As will be apparent to one of ordinary skill in the art in view of this disclosure, tag or sensor weight assignments may be applied to such tag derived data components or sensor derived data components.

In one embodiment, the player dynamics engine may determine participant location data by assigning a first weight to a first tag derived data component (e.g., blink data transmitted by feet placed tags) and a second weight to a second tag derived data component (e.g., blink data transmitted by shoulder pad placed tags) at a first time period (e.g., during a pre-snap or pre-play alignment period). The player dynamics engine may further assign a third weight to the first tag derived data component (e.g., tag derived data transmitted by feet placed tags) and a fourth weight to the second tag derived data component (e.g., tag derived data transmitted by shoulder pad placed tags) at a second time period (e.g., during a post-snap or in-play period).

In another embodiment, the team formation engine may again determine that offensive and defensive players are forming into pre-snap or pre-play positions. In some embodiments, the team formation engine may determine that the movement of certain players (e.g., a quarterback, wide receivers, runningbacks, etc.) is a better indication of pre-snap or pre-play formations than others (e.g., offensive linemen, etc.). For example, when analyzing player location data for comparison to formation models, the team formation engine may assign a first weight (e.g., 1.5) to a first participant component (e.g., location data associated with a quarterback) and a second weight (e.g., 0.1) to a second participant component (e.g., location data associated with a left guard). As discussed above, such weights may be assigned or adjusted by the performance analytics system at various system times (e.g., at initial participant registration, pre-snap, play start, play end, etc.).

In one embodiment, the team formation engine may determine formation data by assigning a first weight to a first participant component (e.g., location data associated with a quarterback) and a second weight to a second participant component (e.g., location data associated with a left guard) at a first time period (e.g., during a pre-snap or pre-play alignment period). The team formation engine may further assign a third weight to the first participant component (e.g., location data associated with a quarterback) and a fourth weight to the second participant component (e.g., location data associated with a left guard) at a second time period (e.g., during a post-snap or in-play period).

In another embodiment, the play engine may again determine that offensive and defensive players are forming into pre-snap or pre-play positions. In some embodiments, the play engine may determine that the movement of certain players (e.g., a quarterback, wide receivers, runningbacks, etc.) is a better indication of plays, or play related events such as play start or play stop, than others (e.g., offensive linemen, etc.). For example, when analyzing changes in formation data for comparison to play models, the play engine may assign a first weight (e.g., 1.5) to a first formation component (e.g., formation data associated with a quarterback) and a second weight (e.g., 0.1) to a second formation component (e.g., formation data associated with a left guard). As discussed above, such weights may be assigned or adjusted by the performance analytics system at various system times or during various periods (e.g., at initial participant registration, pre-snap, play start, play end, in-play, post-play, etc.).

As will be apparent to one of ordinary skill in the art in view of this disclosure, the weights of the various participant components and formation components may be used by the player dynamics engine, the team formation engine, the play engine, or the event engine to improve the performance analytics system. In some embodiments, such weights may be used to allow the performance analytics system to allocate resources (e.g., power, computational, etc.) away from tags, sensors, or participants to enhance battery life or system performance.

In another embodiment, as the team formation engine compares participant location data to the formation models and eliminates certain formations from the list of possible formations, the team formation engine may identify players whose dynamics have little impact on the decision among the remaining possible formations and lower the weights assigned to those particular players (e.g., tag derived data components, sensor derived data components, etc.) or may determine that the dynamics of some other players (e.g., tag derived data components, sensor derived data components, etc.) are highly relevant to certain formations and, thus, increase such other players' weights.

In another example, the official dynamics engine may receive data from the play engine or the formation engine and based on the type of formation or play and/or the location of the particular official in relation to the formation or play, may recognize that the participant location data, formation data, event data, etc., are likely not going to be determinative of one or more plays, formations, penalties, etc. The play engine or formation engine may thus assign lower weights to the participant location data, formation data, or event data associated with such official at least for a period of time (e.g., the length of one play, etc.).

In some embodiments, the performance and analytics system may work out relevance data (i.e., one or more relevance factors) for various participants as part of its play determination methods. For example, the performance and analytics system may receive participant location data determined based on tag location data, tag/sensor derived data, and participant role data, wherein the participant location data comprises a first participant component and a second participant component; receive formation data; determine a relevance factor for each of the first participant component and the second participant component based on the formation data; assign a first weighted participant component and a second weighted participant component based on the relevance factor for each of the first participant component and the second participant component; and determine play data based on comparing the first weighted participant component, the second weighted participant component, and the formation data to play models.

In one example embodiment, the location of the ball may be used to determine a play. In this regard, the performance and analytics system receives ball location data; receives tag derived data, such as blink data transmitted by a plurality of tags, correlated to a plurality of participants (e.g., players, officials, etc.); determines tag location data based on the blink data; receives participant role data; determines participant location data based on comparing the tag location data and participant role data to participant dynamics/kinetics models; and determines play data (e.g., a play or series of plays) based on the comparing the participant location data and the ball location data to play models.

In another example embodiment, the location of one or more officials may be used to determine a play. In this regard, the performance and analytics system receives official location data; receives tag derived data, such as blink data transmitted by a plurality of tags, correlated to a plurality of participants (e.g., players, other officials, etc.); determines tag location data based on the blink data; receives participant role data; determines participant location data based on comparing the tag location data and participant role data to participant dynamics/kinetics models; and determines play data (e.g., a play or series of plays) based on the comparing the participant location data and the official location data to play models.

Example Weather Integration Embodiments

In some embodiments, the various engines and/or output systems may incorporate real-time weather data into the performance analytics. Outdoor sporting events are often affected by weather conditions that may in turn affect decisions related to carrying out the sporting event or affect the analysis and/or prediction of a player's performance in the sporting event.

In such embodiments, the performance analytics system may further include weather sensors such as anemometers, temperature sensors, rain sensors, or the like. In some embodiments, returning for example to FIG. 1, the weather sensors may have location tags, such as location tags 102, attached or incorporated thereto, so as to provide location data for the weather sensors to the performance analytics system. In other embodiments, the weather sensors 125 may be mounted in a fixed weather exposed location. In the depicted embodiment, weather sensors 125 are mounted to an upper portion of the goal posts (not shown).

The weather sensors 125 may provide real-time weather data (i.e., sensor derived data from one or more weather sensors), such as wind speed, wind direction, barometric pressure, sunlight intensity, temperature, precipitation, or the like. In some embodiments where the weather sensors are integrated into tags 102, for example, location information for the weather sensors may be transmitted to the performance analytics system through wired connections or wireless connections (i.e., as tag derived data or sensor derived data, etc.), from the receivers 106. The performance analytics system may correlate the time and location of participants (e.g., player, ball, etc.) and the weather sensor derived data to create weather-adjusted participant location data. The performance analytics system may correlate time, formation, and the weather sensor derived data to create weather-adjusted formation data. The performance analytics system may correlate the time, play data, and the weather sensor derived data to create weather-adjusted play data. In this regard, the performance analytics system may determine weather related impacts on participant performance, formation performance, team performance, output events, the trajectory of the ball, etc.

In one embodiment, the performance and analytics system may determine player performance information based on comparing the player location data and the weather sensor derived data to stored weather-adjusted player location data. In another embodiment, the performance and analytics system may determine team performance information based on comparing the formation data and the weather sensor derived data to stored weather-adjusted formation data. In still another embodiment, the performance and analytics system may determine team performance information based on comparing the play data and the weather sensor derived data to stored weather-adjusted play data.

In some embodiments, a plurality of weather sensors may be located proximate a monitored area or zone (i.e., a field of play). Weather sensor derived data from such plurality of sensors may be used to determine weather conditions proximate such sensors. In this regard, the performance and analytics system configured as described herein may organize such weather sensor derived data into various weather zones (e.g., horizontal zones, vertical zones, etc.) within the monitored area to better analyze the impact of weather on participant performance (e.g., player performance), formation performance, team performance, output events, and the like.

The above zone-based weather data organization may be used when determining how a play should be executed or modified. For example, wind conditions may be different in different portions of a monitored area (e.g., a playing field) and by having knowledge of such different weather conditions (i.e., the conditions in various monitored zones), a passing play or field goal attempt may be modified to take advantage of conditions in each specific zone. For example, passing plays or kicking plays may be determined to be executed or not executed in certain zones of the field based on wind conditions in such zones.

Weather sensor derived data from various weather sensors 125 may be stored to a database such as weather data store 375 of FIG. 3. Such weather sensor derived data may be fed to event engine 322. In other embodiments, weather sensor derived data from the weather data store 375 may be accessed by the player dynamics engine 306, the official dynamics engine 324, the ball engine 330, the team formation engine 312, the play engine 318, and the event engine 322.

In various embodiments, output events generated by one or more of the above engines may account for, or filter out, uncontrollable weather events. For example, when evaluating participant performance, a "no wind" or steady-state wind trajectory for the ball may be calculated and used to determine if a kick or a pass would have been successful (i.e., reached its target) if not for a change in weather conditions (e.g., wind gusts, etc.). In another example, an interception or pass incompletion could be determined to have been aided by wind conditions (e.g., wind gusts, etc.). Alternatively, kicks or pass completions may be determined to have been aided by wind conditions.

Temperature, moisture, humidity, etc., can be correlated to participant, team, formation, and/or play performance (positive performance or negative performance) to assist in arriving at more accurate evaluations versus prior or predicted performance levels. In still another embodiment, such correlations may be helpful in creating more robust participant dynamics models, formation models, and play models.

Example Process or Method Embodiments

Figure 6A:
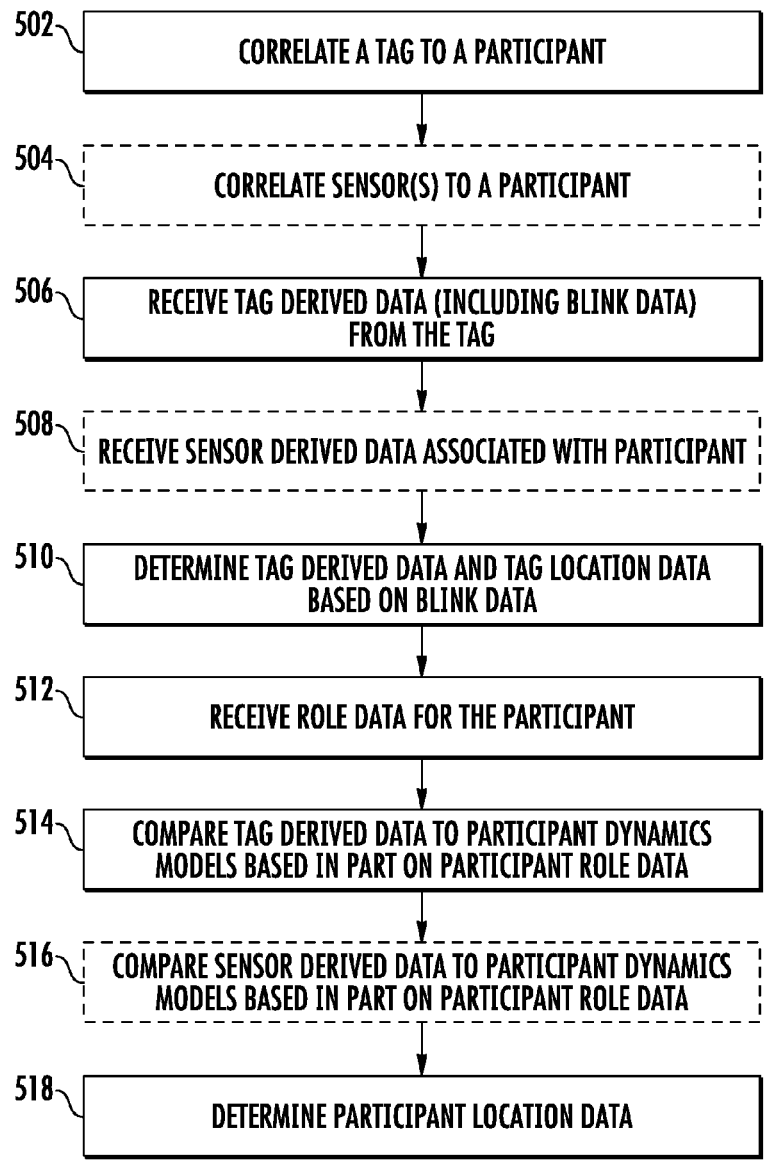

FIG. 6A illustrates a flowchart of an exemplary process for performance analytics using a locating system in accordance with some embodiments of the present invention. The process may start at 502, where one or more tags (e.g., tags 102 as shown in FIG. 1) may be correlated to a participant (e.g., a player, official, ball, etc.). Additionally, in some embodiments, one or more sensors (e.g., sensors 203 as shown in FIG. 2A-C) may be correlated to a participant at 504. The tags 102 (and optionally sensors 203) may be attached to participants, such as to players, officials, balls, field markers, penalty flags, other game equipment, and reference markers on a field of play (e.g., boundary defining reference markers). For example, in the case of players or officials, the tags and/or sensors may be attached to equipment, uniforms, etc., worn or carried by the players or officials.

At 506, blink data is received from the one or more tags 102. Additionally, in some embodiments, other tag derived data and sensor derived data, such as from sensors 203 associated with the participant, may be received with the blink data or separate from the blink data at 508.

At 510, tag location data is determined (e.g., perhaps by receiver hub/locate engine 302) from the blink data as discussed above. Role data for the participant is received at step 512.

In some embodiments, each participant may be associated with one or more tags 102 and/or one or more sensors 203 (e.g., multiple tags 102 and sensors 203 may be attached to an individual player's equipment, such as to provide more accurate location and multi-dimensional location or orientation data). A filter (e.g., tag ID/filter 304 of FIG. 3) may process the incoming stream of tag location data to identify tags 102 that are associated with a given participant (e.g., multiple tags attached to a player, a ball, an official, etc.). The filter may correlate the tag location data associated with multiple tags 102 where the multiple tags 102 are associated with the same participant (e.g., player or official), such as to provide more accurate data regarding the activities of a participant. Once the tag location data is correlated to a given participant, it may be routed to an appropriate engine (e.g., player dynamics engine, official dynamics engine, ball engine, field marker engine, etc.) based at least in part on the received role data and such correlation. Additionally, in some embodiments, sensor derived data from multiple sensors 203 that are associated with a given participant may be correlated in a similar fashion.

In embodiments where the tag location data is routed to the player dynamics engine, the player dynamics engine (e.g., player dynamics engine 306 of FIG. 3) may receive the stream of participant correlated tag derived data, and optionally, other tag/sensor derived data, from the filter. In other embodiments, depending on the type of participant, the below process may be performed by other appropriate engines such as the official dynamics engine, the ball engine, the field marker engine, etc.

At 514, the player dynamics engine may compare the tag derived data and the received player role data to a plurality of player dynamics/kinetics models to determine player dynamics (e.g., multi-dimensional player location information) for each participant (e.g., player). Additionally, in some embodiments, the received sensor derived data may be used in the comparison to a plurality of player dynamics/kinetics models to determine player dynamics at 516.

At 518, the player dynamics engine may determine player location data for each player (e.g., player dynamics or multi-dimensional player location information), such as location, change in location, orientation, velocity, acceleration, deceleration, or the like. The player dynamics engine may then provide an output stream of the player location data, such as to a team formation engine, a play engine, an event engine, or the like.

Figure 6B:
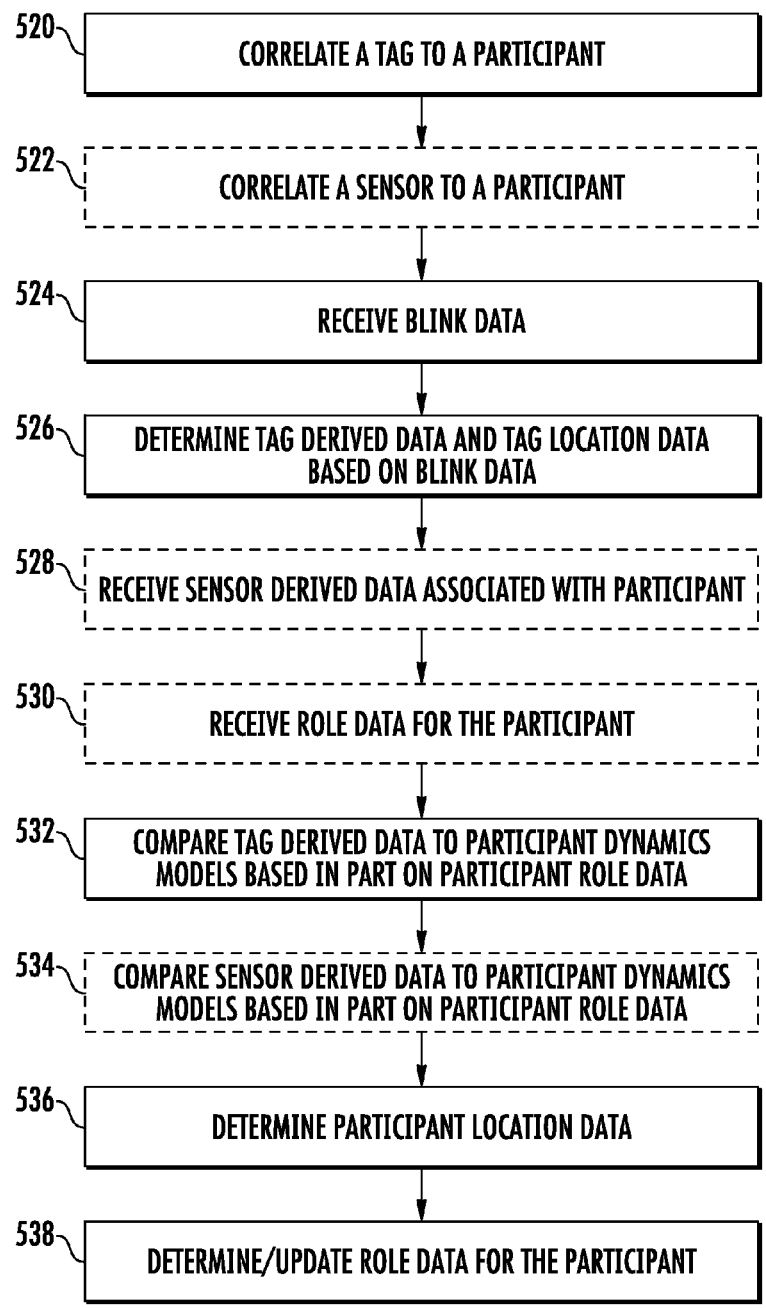

FIG. 6B illustrates a flowchart of another exemplary process for performance analytics using a locating system in accordance with some embodiments of the present invention. The process may start at 520, where one or more tags (e.g., tags 102) may be correlated to a participant (e.g., a player, official, ball, etc.). Additionally, in some embodiments, one or more sensors (e.g., sensors 203) may be correlated to a participant at 522.

At 524, blink data is received from the one or more tags 102. Additionally, in some embodiments, other tag derived data and sensor derived data, such as from sensors 203 associated with the participant, may be received with the blink data or separate from the blink data at 528. Tag location data is determined (e.g., perhaps by receiver hub/locate engine 302) from the blink data at step 526.

At 530, a player dynamics engine may receive tag derived data for the tags 102 where the tag derived data may be indicative of a player location (e.g., as opposed to an official location, a field marker location, etc.). Additionally, in some embodiments, other tag and sensor derived data, such as from sensors 203 associated with the player, may be received with the blink data or separate from the blink data at 528.

In some embodiments, at 530, the player dynamics engine may optionally receive player role data for the player, such as by comparing a tag identifier of the tag derived data to a database of player roles.

At 532, the player dynamics engine may then compare the tag derived data (and optionally the player role data) to a plurality of player dynamics/kinetics models to determine player dynamics (e.g., multi-dimensional player location information) for each player. Additionally, in some embodiments, the received sensor derived data may be used in the comparison to a plurality of player dynamics/kinetics models to determine player dynamics at 534.

At 536, the player dynamics engine may determine player location data for each player, such as location, change in location, orientation, velocity, acceleration, deceleration, or the like.

At 538, the player role data may be created or updated, such as in a player role database, based on the player location data. For example, if participant role data for the particular participant already exists in a participant role database, the participant role data may be updated or changed based on an analysis of the participant location data. If participant role data for a particular participant does not exist in the participant role database, a new participant role data entry may be created for that particular participant and stored to the database. As such, the performance analytics system may learn about participant roles as a result of analyzing the participant dynamics (participant location data).

In some embodiments, the participant role data (e.g., player role data) may comprise participant profile data such as the role of the participant in the game or sporting event (e.g., what position a player is assigned), biometric data, participant analysis data, team ID, performance statistics, and/or the like. For example, the player role data may additionally include data regarding a player's normal gait, the pattern a player typically runs, how long on average it takes a player to start from a line of scrimmage, etc. Some embodiments may learn and update one or more portions of the player role data based on the analysis of the participant location data. For example, the performance analytics system may identify that a player's assigned position may have changed based on the changes in the player location data and the player dynamics, or the system may identify a player's typical gait or typical running pattern by analyzing the player location data (and/or other tag/sensor derived data), and then update the player role data accordingly.

Figure 7:
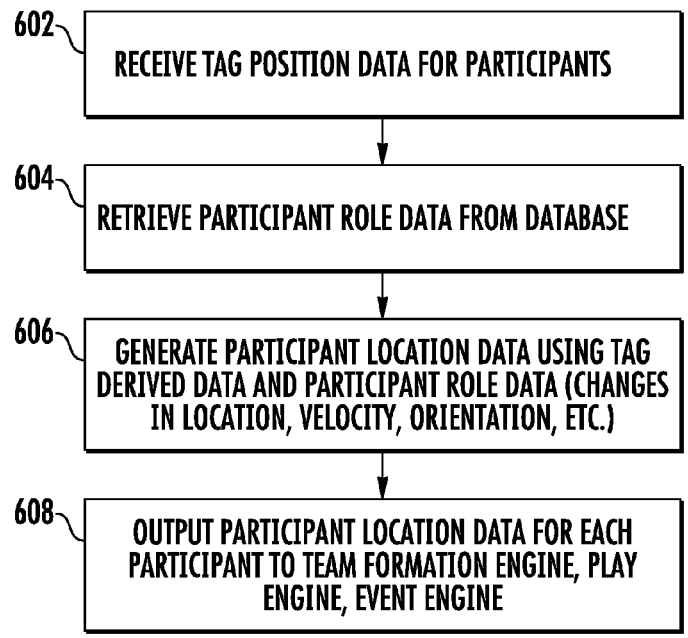

FIG. 7 illustrates a flowchart of an exemplary process for a player dynamics engine (e.g., player dynamics engine 306 of FIG. 3) in accordance with some embodiments of the present invention. The process may start at 602, where tag location data is received for tags 102. In some embodiments, such tag location data may be determined by a receiver hub/locate engine 302 based on blink data transmitted by the tags 102. Additionally, in some embodiments, other tag and sensor derived data, such as from sensors 203, may be received with the tag location data or separately from the tag location data. At 604, the player dynamics engine may retrieve player role data from a database based on the tag ID (or participant ID) of the tag derived data. At 606, the player dynamics engine may use the player role data, player dynamics/kinetics models (e.g., from one or more databases of player dynamics/kinetics models), the tag location data, and, optionally, the other tag derived data and/or sensor derived data to determine player dynamics (e.g., multi-dimensional player location information) for each particular player, such as location, change in location, velocity, acceleration, deceleration, orientation, or the like. At 608, the player dynamics engine may provide an output stream of the player dynamics over time (e.g., participant location data), such as to a team formation engine, a play engine, an event engine, or the like.

Figure 8:
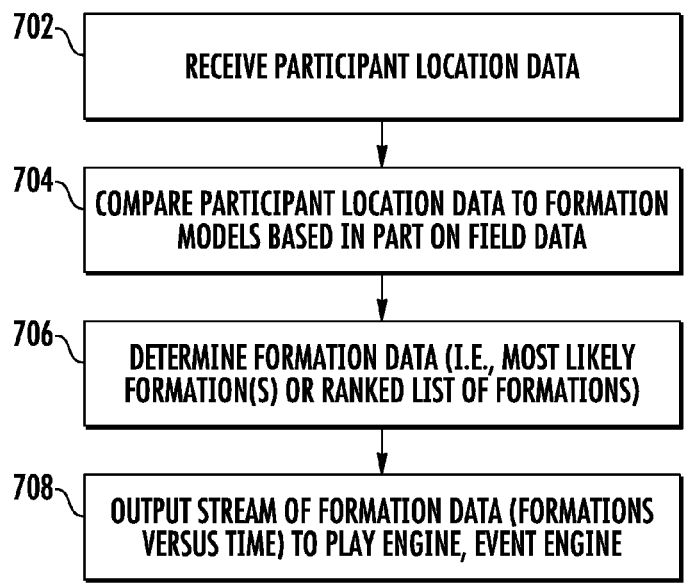

FIG. 8 illustrates a flowchart of an exemplary process for a team formation engine (e.g., team formation engine 312 of FIG. 3) in accordance with some embodiments of the present invention. The process may start at 702, where a player dynamics data stream (e.g., player location data) is received (e.g., from a player dynamics engine), which may comprise blink data, tag location data, sensor data, and other player dynamics data for a plurality of players. At 704, the team formation engine may retrieve field data and formation models from one or more databases and compare the player dynamics data stream, in conjunction with the field data, to the plurality of formation models. The team formation engine may analyze the data stream of player dynamics over time to determine a probable formation, or set of probable formations, (e.g., the likelihood that a particular formation is occurring or forming) at 706. For example, the team formation engine may determine the most probable team formation (or ranked list of probable formations) at a particular point in time. At 708, the team formation engine may provide an output stream of the formations versus time (e.g., formation data), such as to a play engine, an event engine, or the like.

Figure 9:
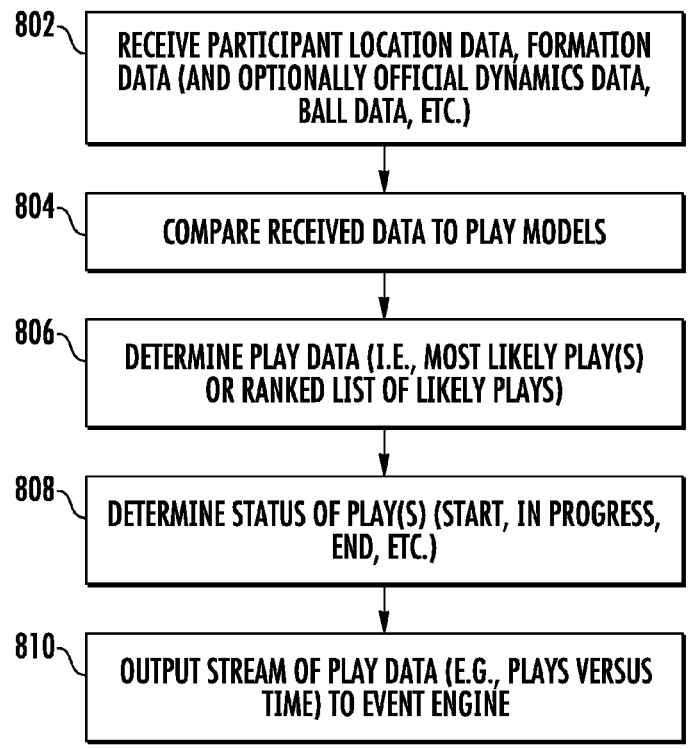

FIG. 9 illustrates a flowchart of an exemplary process for a play engine (e.g., play engine 318 of FIG. 3) in accordance with some embodiments of the present invention. The process may start at 802, where a player dynamics data stream (e.g. player location data) and team formations versus time data stream (e.g., formation data) are received (e.g., from a player dynamics engine and a team formation engine, respectively). In some embodiments, additional data may be received, such as an official dynamics data stream, a ball versus time data stream, a field marker data stream, and/or the like to further improve play determination accuracy or assist in generating play data. At 804, the play engine may retrieve play models from one or more databases and compare the received data streams to the plurality of play models. The play engine may analyze the data streams in conjunction with the play models to determine a probable play, or set of probable plays, at 806. At 808, the play engine may analyze the data stream to determine the status of the particular play, such as play start, in progress, play stop, or the like. In determining that a play has formed, started, ended, etc., the play engine may weigh and analyze the received data streams and compare to the play models to generate a ranked list of one or more probable play events and include an associated probability that the received data matches each particular model or pattern. At 810, the play engine may provide an output stream of the plays versus time (e.g., play data), such as to an event engine, or the like.

Figure 10:
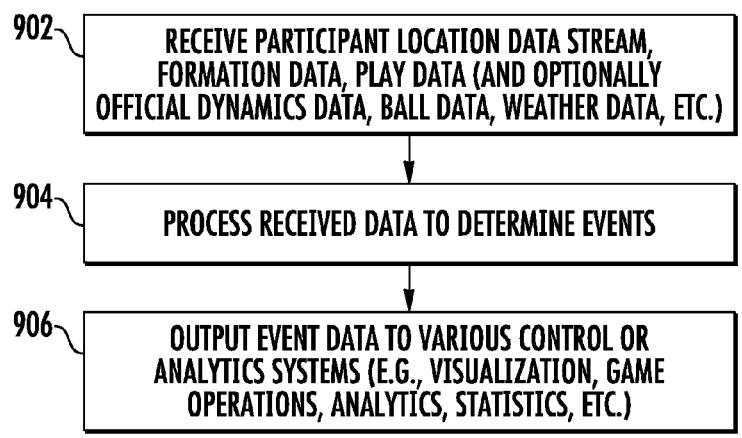

FIG. 10 illustrates a flowchart of an exemplary process for an event engine (e.g., event engine 322 of FIG. 3) in accordance with some embodiments of the present invention. The process may start at 902, where a player dynamics data stream (e.g., player location data), team formations versus time data stream (e.g., formation data), and a plays versus time data stream (e.g., play data) are received (e.g., from a player dynamics engine, a team formation engine, and a play engine, respectively). In some embodiments, additional data streams may be received, such as an official dynamics data stream, a ball versus time data stream, a field marker data stream, a weather data stream, and/or the like to assist in generating event data streams. At 904, the event engine may process the received data streams to determine and generate events during, or in conjunction with, a game. At 906, the event engine may provide output streams of the event data to various storage, analysis, and/or control systems, such as, without limitation, to a historical data store 336, a visualization system 340, a game operations system 342, a camera control system 344, a team analytics system 346, a league analytics system 348, a statistics system 350, an XML feed/IM feed system, and/or the like.

FIG. 11 illustrates a flowchart of an exemplary process for team analysis, such as by a team analytics system (e.g., team analytics system 346 of FIG. 3), in accordance with some embodiments of the present invention. The process may start at 1002, where input play data (e.g., future/potential play models) for a particular team may be received, such as through a model generation engine 338. At 1004, the team analytics system may determine a particular type of analysis to be performed using the input play data. If a selection is made to compare the input plays against the play models in the system (e.g., play model databases), at 1006, the team analytics system may compare the input plays against each of the appropriate play models (i.e., offensive plays, defensive plays, etc.) in the play model database, such as using performance data associated with the play models from historical data store 336. If a selection is made to compare the input plays against the formation models in the system, at 1008, the team analytics system may compare the input plays against each of the appropriate formations for each of the appropriate play models (i.e., offensive plays, defensive plays, etc.) in the formation and play model databases, such as using performance data associated with the formation and play models from historical data store 336. If a selection is made to compare the input plays against the historical play data of another team, at 1010, the team analytics system may compare the input plays against each of the appropriate play models used by the other team, such as using performance data associated with the play models from historical data store 336. At 1012, the team analytics system may output the results of the analysis.

FIG. 12 illustrates a flowchart of an exemplary process for player analysis, such as by a team analytics system, in accordance with some embodiments of the present invention. The process may start at 1102, where a user may input a selection of a player for analysis. At 1104, the team analytics system may retrieve historical player data and/or statistics for the selected player, such as from historical data store 336. At 1106, the team analytics system may determine the selection of a particular type of analysis to be performed for the selected player. If a selection is made to compare the player's performance against the play models in the system, at 1108, the team analytics system may compare the player performance against each of the appropriate play models (i.e., offensive plays, defensive plays, etc.) in the play model database, such as using performance data of the play models by the player's team from the historical data store 336. If a selection is made to compare player performance against the formation models in the system, at 1110, the team analytics system may compare the player performance against each of the appropriate formations for each of the appropriate play models (i.e., offensive plays, defensive plays, etc.) in the formation and play model databases, such as using historical performance data of the formation and play models by the player's team from the historical data store 336. If a selection is made to compare the player performance against the historical play data of another team, at 1012, the team analytics system may compare the player performance against each of the appropriate play models used by the other team, such as using historical performance data of the play models from the historical data store 336. At 1114, the team analytics system may output the results of the analysis.

Example Processing Apparatus

FIG. 13 shows a block diagram of components that may be included in an apparatus that may provide performance analytics in accordance with embodiments discussed herein. Apparatus 1200 may comprise one or more processors, such as processor 1202, one or more memories, such as memory 1204, communication circuitry 1206, and user interface 1208. Processor 1202 can be, for example, a microprocessor that is configured to execute software instructions and/or other types of code portions for carrying out defined steps, some of which are discussed herein. Processor 1202 may communicate internally using data bus, for example, which may be used to convey data, including program instructions, between processor 1202 and memory 1204.

Memory 1204 may include one or more non-transitory storage media such as, for example, volatile and/or non-volatile memory that may be either fixed or removable. Memory 1204 may be configured to store information, data, applications, instructions or the like for enabling apparatus 1200 to carry out various functions in accordance with example embodiments of the present invention. For example, the memory could be configured to buffer input data for processing by processor 1202. Additionally or alternatively, the memory could be configured to store instructions for execution by processor 1202. Memory 1204 can be considered primary memory and be included in, for example, RAM or other forms of volatile storage which retain its contents only during operation, and/or memory 1204 may be included in non-volatile storage, such as ROM, EPROM, EEPROM, FLASH, or other types of storage that retain the memory contents independent of the power state of the apparatus 1200. Memory 1204 could also be included in a secondary storage device, such as external disk storage, that stores large amounts of data. In some embodiments, the disk storage may communicate with processor 1202 using an input/output component via a data bus or other routing component. The secondary memory may include a hard disk, compact disk, DVD, memory card, or any other type of mass storage type known to those skilled in the art.

In some embodiments, processor 1202 may be configured to communicate with external communication networks and devices using communications circuitry 1206, and may use a variety of interfaces such as data communication oriented protocols, including X.25, ISDN, DSL, among others. Communications circuitry 1206 may also incorporate a modem for interfacing and communicating with a standard telephone line, an Ethernet interface, cable system, and/or any other type of communications system. Additionally, processor 1202 may communicate via a wireless interface that is operatively connected to communications circuitry 1206 for communicating wirelessly with other devices, using for example, one of the IEEE 802.11 protocols, 802.15 protocol (including Bluetooth, Zigbee, and others), a cellular protocol (Advanced Mobile Phone Service or "AMPS"), Personal Communication Services (PCS), or a standard 3G wireless telecommunications protocol, such as CDMA2000 1x EV-DO, GPRS, W-CDMA, LTE, and/or any other protocol.

The apparatus 1200 may include a user interface 1208 that may, in turn, be in communication with the processor 1202 to provide output to the user and to receive input. For example, the user interface may include a display and, in some embodiments, may also include a keyboard, a mouse, a joystick, a touch screen, touch areas, soft keys, a microphone, a speaker, or other input/output mechanisms. The processor may comprise user interface circuitry configured to control at least some functions of one or more user interface elements such as a display and, in some embodiments, a speaker, ringer, microphone and/or the like. The processor and/or user interface circuitry comprising the processor may be configured to control one or more functions of one or more user interface elements through computer program instructions (e.g., software and/or firmware) stored on a memory accessible to the processor (e.g., memory 1204, and/or the like).

In some embodiments, certain ones of the operations above may be modified or further amplified as described below. Moreover, in some embodiments additional optional operations may also be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for determining play data, the method comprising:
   correlating at least one tag to a participant;
   receiving blink data transmitted by the at least one tag;
   determining tag location data based on the blink data;
   receiving participant role data;
   comparing the tag location data to participant dynamics/kinetics models based at least in part on the participant role data;
   determining participant location data based on the comparing the tag location data to the participant dynamics/kinetics models
   receiving field data;
   comparing the participant location data to formation models based at least in part on the participant role data and the field data;
   determining formation data based on the comparing the participant location data to the formation models;
   comparing the formation data and participant location data to play models; and
   determining play data based on the comparing the formation data and participant location data to the play models.

2. The method of claim 1 further comprising:
   updating the play models based on the play data.

3. The method of claim 1 further comprising:
  determining output events based at least in part on the tag location data, the participant location data, the formation data, and the play data;
  storing the output events in a data store; and
  providing at least some of the output events to one or more analytics systems or control systems.

4. The method of claim 3 wherein the providing the output events to one or more analytics systems or control systems includes providing at least some of the output events to a visualization system, wherein the visualization system is configured to generate graphics, displays, or visualizations of the at least some of the output events.

5. The method of claim 3 wherein the providing the output events to one or more analytics systems or control systems includes providing at least some of the output events to a game operations system, wherein the game operations system is configured to update at least one of a game clock, a play clock, and a score board based on the at least some of the output events.

6. The method of claim 3 wherein the providing the output events to one or more analytics systems or control systems includes providing at least some of the output events to a camera control system, wherein the camera control system is configured to engage one or more cameras based on the at least some of the output events.

7. The method of claim 3 wherein the determining output events further includes determining output events based at least in part on weather data received from one or more weather sensors.

8. An apparatus for determining play data comprising at least one processor and at least one memory including computer program instructions, the at least one memory and the computer program instructions configured to, in cooperation with the at least one processor, cause the apparatus to:
  correlate at least one tag to a participant;
  receive blink data transmitted by the at least one tag;
  determine tag location data based on the blink data;
  receive participant role data;
  compare the tag location data to participant dynamics/kinetics models based at least in part on the participant role data;
  determine participant location data based on the comparing the tag location data to the participant dynamics/kinetics models
  receive field data;
  compare the participant location data to formation models based at least in part on the participant role data and the field data; and
  determine formation data based on the comparing the participant location data to the formation models;
  compare the formation data and participant location data to play models; and
  determine play data based on the comparing the formation data and participant location data to the play models.

9. The apparatus of claim 8 further comprising the at least one memory and the computer program instructions configured to, in cooperation with the at least one processor, cause the apparatus to:
  update the play models based on the play data.

10. The apparatus of claim 8 further comprising the at least one memory and the computer program instructions configured to, in cooperation with the at least one processor, cause the apparatus to:
  determine output events based at least in part on the tag location data, the participant location data, the formation data, and the play data;
  store the output events in a data store; and
  provide at least some of the output events to one or more analytics systems or control systems.

11. The apparatus of claim 10 wherein the providing the output events to one or more analytics systems or control systems includes providing at least some of the output events to a visualization system, wherein the visualization system is configured to generate graphics, displays, or visualizations of the at least some of the output events.

12. The apparatus of claim 10 wherein the providing the output events to one or more analytics systems or control systems includes providing at least some of the output events to a game operations system, wherein the game operations system is configured to update at least one of a game clock, a play clock, and a score board based on the at least some of the output events.

13. The apparatus of claim 10 wherein the providing the output events to one or more analytics systems or control systems includes providing at least some of the output events to a camera control system, wherein the camera control system is configured to engage one or more cameras based on the at least some of the output events.

14. A computer program product for determining play data, the computer program product comprising a non-transitory computer readable storage medium and computer program instructions stored therein, the computer program instructions comprising program instructions at least configured to:
  correlate at least one tag to a participant;
  receive blink data transmitted by the at least one tag;
  determine tag location data based on the blink data;
  receive participant role data;
  compare the tag location data to participant dynamics/kinetics models based at least in part on the participant role data;
  determine participant location data based on the comparing the tag location data to the participant dynamics/kinetics models
  receive field data;
  compare the participant location data to formation models based at least in part on the participant role data and the field data;
  determine formation data based on the comparing the participant location data to the formation models;
  compare the formation data and participant location data to play models; and
  determine play data based on the comparing the formation data and participant location data to the play models.

15. The computer program product of claim 14 further comprising computer program instructions at least configured to:
  update the play models based on the play data.

16. The computer program product of claim 14 further comprising computer program instructions at least configured to:
  determine output events based at least in part on the tag location data, the participant location data, the formation data, and the play data;
  store the output events in a data store; and
  provide at least some of the output events to one or more analytics systems or control systems.

17. The computer program product of claim 16 wherein the providing the output events to one or more analytics systems or control systems includes providing at least some of the output events to a visualization system, wherein the visualization system is configured to generate graphics, displays, or visualizations of the at least some of the output events.

18. The computer program product of claim 16 wherein the providing the output events to one or more analytics systems or control systems includes providing at least some of the output events to a game operations system, wherein the game operations system is configured to update at least one of a game clock, a play clock, and a score board based on the at least some of the output events.

19. The computer program product of claim 16 wherein the providing the output events to one or more analytics systems or control systems includes providing at least some of the output events to a camera control system, wherein the camera control system is configured to engage one or more cameras based on the at least some of the output events.

20. The computer program product of claim 16 wherein the determining output events further includes determining output events based at least in part on weather data received from one or more weather sensors.

* * * * *